US011332493B2

(12) United States Patent
Gracias et al.

(10) Patent No.: US 11,332,493 B2
(45) Date of Patent: May 17, 2022

(54) PROGRAMMABLE SOFT ROBOT

(71) Applicant: THE JOHNS HOPKINS UNIVERSITY, Baltimore, MD (US)

(72) Inventors: David H. Gracias, Baltimore, MD (US); Thao D. Nguyen, Baltimore, MD (US); ChangKyu Yoon, Timonium, MD (US); Rebecca B. Schulman, Baltimore, MD (US); Angelo Cangialosi, Baltimore, MD (US); Ruohong Shi, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 255 days.

(21) Appl. No.: 16/634,994

(22) PCT Filed: Aug. 31, 2018

(86) PCT No.: PCT/US2018/049005
§ 371 (c)(1),
(2) Date: Jan. 29, 2020

(87) PCT Pub. No.: WO2019/164548
PCT Pub. Date: Aug. 29, 2019

(65) Prior Publication Data
US 2020/0377544 A1 Dec. 3, 2020

Related U.S. Application Data

(60) Provisional application No. 62/553,751, filed on Sep. 1, 2017.

(51) Int. Cl.
| | |
|---|---|
| *C07H 19/00* | (2006.01) |
| *C07H 21/00* | (2006.01) |
| *A61K 9/70* | (2006.01) |
| *A61L 27/26* | (2006.01) |
| *A61L 27/52* | (2006.01) |
| *G03F 7/20* | (2006.01) |

(52) U.S. Cl.
CPC ............ *C07H 21/00* (2013.01); *A61K 9/7007* (2013.01); *A61L 27/26* (2013.01); *A61L 27/52* (2013.01); *G03F 7/20* (2013.01)

(58) Field of Classification Search
None
See application file for complete search history.

(56) References Cited

U.S. PATENT DOCUMENTS 6,511,803 B1  1/2003  Church et al.

OTHER PUBLICATIONS

Li, G., et al., "Design, preparation, and selection of DNA-encoded dynamic libraries" Chem. Sci., 2015, 6, 7097-7104.

Xiong, X., et al., "Responsive DNA-based hydrogels and their applications" Macromol Rapid Commun. Aug. 2013 ;34(16): 1271-1283. doi:10.1002/marc.201300411.
Wahl et al., Molecular hybridization of immobilized nucleic acids: Theoretical concepts and practical considerations., (1987) Methods Enzymol. 152:399.
Kimmel., Identification and characterization of specific clones: Strategy for confirming the validity of presumptive clones., (1987) Methods Enzymol. 152:507.
Benton et al., Screening lambdagt recombinant clones by hybridization to single plaques in situ., Science 196:180, 1977.
Grunstein et al.,Colony hybridization: A method for the isolation of clofied DNAs that contain a specific gene., Proc. Natl. Acad. Sci, USA 72:3961, 1975.
Hu et al., A Shape Memory Acrylamide/DNA Hydrogel Exhibiting Switchable Dual pH-Responsiveness., Adv. Funct. Mater., 2015, 25 (44), pp. 6867-6874.
Iiievski et al., Soft robotics for chemists. Angew. Chemie—Int. Ed. 50, 1890-1895 (2011).
Rus et al., Design, fabrication and control of soft robots. Nature 521, 467-475 (2015).
Douglas et al., A Logic-Gated Nanorobot for Targeted Transport of Molecular Payloads. Science. 335, 831 (2012).
Ionov., Biomimetic hydrogel-based actuating systems. Adv. Funct. Mater. 23, 4555-4570 (2013).
Jeon et al., Shape-Morphing Materials from Stimuli-Responsive Hydrogel Hybrids. Acc. Chem. Res. 50, 161-169 (2017).
Gracias., Stimuli responsive self-folding using thin polymer films. Curr. Opin. Chem. Eng. 2, 112-119 (2013).
Liu et al., Self-folding of polymer sheets using local light absorption. Soft Matter 8, 1764 (2012).
Zarzar et al., Stimuli-responsive chemomechanical actuation: A hybrid materials approach. Acc. Chem. Res. 47, 530-539 (2014).
Zhou et al., Aptamer-based biosensors for biomedical diagnostics. Analyst 139, 2627-2640 (2014).
Zhang et al., Dynamic DNA nanotechnology using strand-displacement reactions. Nat. Chem. 3, 103-113 (2011).
Hawkes et al., Programmable matter by folding. Proc. Natl. Acad. Sci. 107, 12441-12445 (2010).
Postma et al., Preprogramming Complex Hydrogel Responses using Enzymatic Reaction Networks. Angew. Chemie Int. Ed. 1-6 (2017).
Ikeda et al.. Installing logic-gate responses to a variety of biological substances in supramolecular hydrogel-enzyme hybrids. Nat. Chem. 6, 511-8 (2014).
Yan et al., A robust DNA mechanical device controlled by hybridization topology. Nature 415, 62-65 (2002).
Shim et al., Shape changing thin films powered by DNA hybridization. Nat. Nanotechnol. 1-8 (2016).
Maye et al., Switching binary states of nanoparticle superlattices and dimer clusters by DNA strands. Nat. Nanotechnol. 5, 116-120 (2010).
Nagahara et al., Hydrogel formation via hybridization of oligonucleotides derivatized in water-soluble vinyl polymers. Polym. Gels Networks 4, 111-127 (1996).

(Continued)

*Primary Examiner* — Patrick T Lewis
(74) *Attorney, Agent, or Firm* — Casimir Jones, S.C.; Kelly Barton

(57) ABSTRACT

Described are a combinatorial library of DNA molecules that can induce shape changes within specific regions of hydrogels up to centimeter scales. The DNA molecules include polymerizing hairpins, terminating hairpins, reversal strands, and crosslink nucleic acid sequences.

39 Claims, 73 Drawing Sheets

Specification includes a Sequence Listing.

(56) References Cited

OTHER PUBLICATIONS

Liedl et al.. Controlled trapping and release of quantum dots in a DNA-switchable hydrogel. Small 3, 1688-1693 (2007).
Wang et al., Bioresponsive DNA Hydrogels: Beyond the Conventional Stimuli Responsiveness. Acc. Chem. Res. acs. accounts. 6b00581 (2017).
Hu et al.. Reversible Modulation of DNA-Based Hydrogel Shapes by Internal Stress Interactions. J. Am. Chem. Soc. acs.6b10458 (2016).
Lin et al., Inducing Reversible Stiffness Changes in DNAcrosslinked Gels. J. Mater. Res. 20, 1456-1464 (2005).
Zhang et al., Applicability range of Stoney's formula and modified formulas for a film/substrate bilayer. J. Appl. Phys. 99, (2006).
Venkataraman et al., An autonomous polymerization motor powered by DNA hybridization. Nat. Nanotechnol. 2, 490-494 (2007).
Breger et al., Self-folding thermo-magnetically responsive soft microgrippers. ACS Appl. Mater. Interfaces 7, 3398-3405 (2015).
Flory et al., Statistical Mechanics of Cross-Linked Polymer Networks. J. Chem. Phys. 11, 512-520 (1943).
Freund et al., Extensions of the Stoney formula for substrate curvature to configurations with thin substrates or large deformations. Appl. Phys. Lett. 74, 1987-1989 (1999).
Qian et al., Scaling up digital circuit computation with DNA strand displacement cascades. Science 332, 1196-1201 (2011).
Schulman et al., Robust self-replication of combinatorial information via crystal growth and scission. Proc. Natl. Acad. Sci. 109, 6405-6410 (2012).
Linder et al., Water-soluble sacrificial layers for surface micromachining. Small 1, 730-736 (2005).
Kang et al., Photoresponsive DNA-cross-linked hydrogels for controllable release and cancer therapy. Langmuir 27, 399-408 (2011).

FIG. 5
(1) Polymerizing a poly(Am-co-BIS) hydrogel
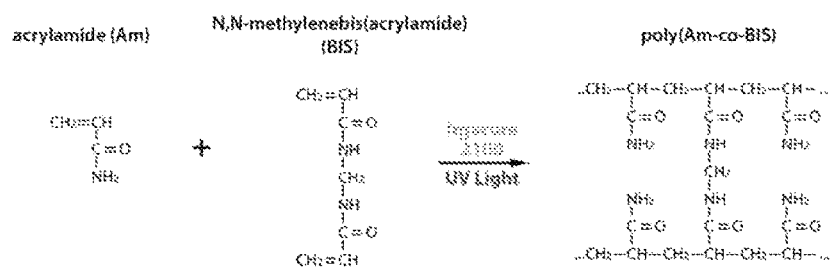
(2) Polymerizing a poly(Am-co-DNA) hydrogel
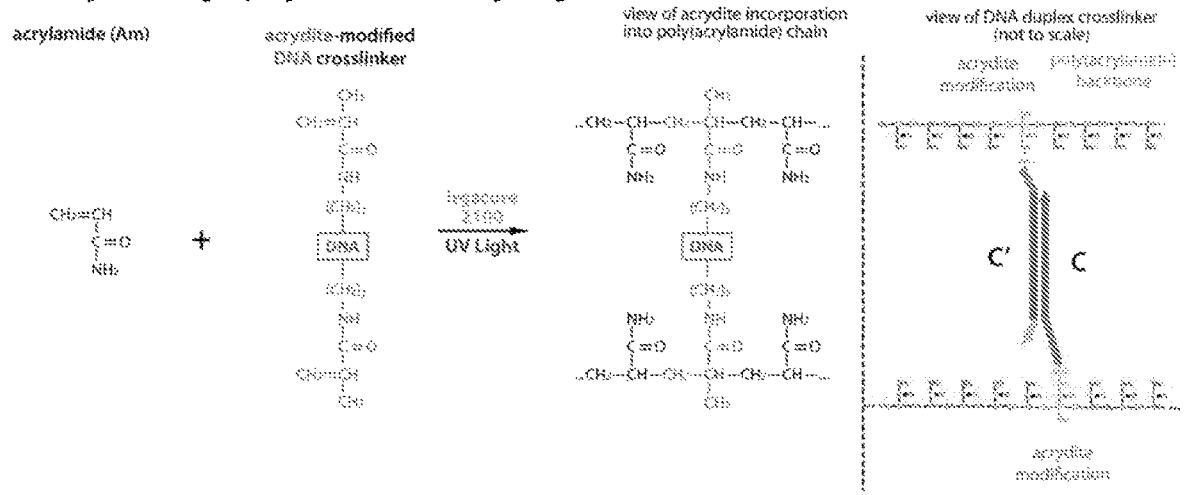

FIG. 25
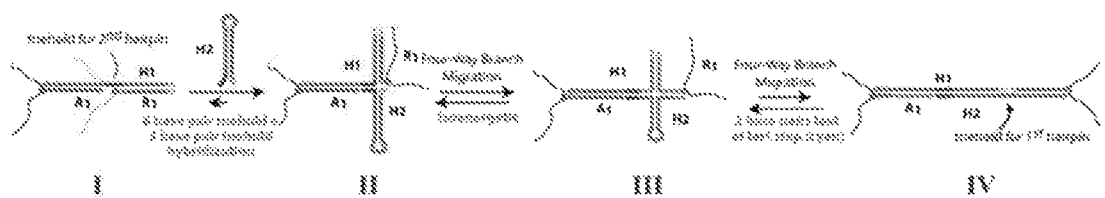
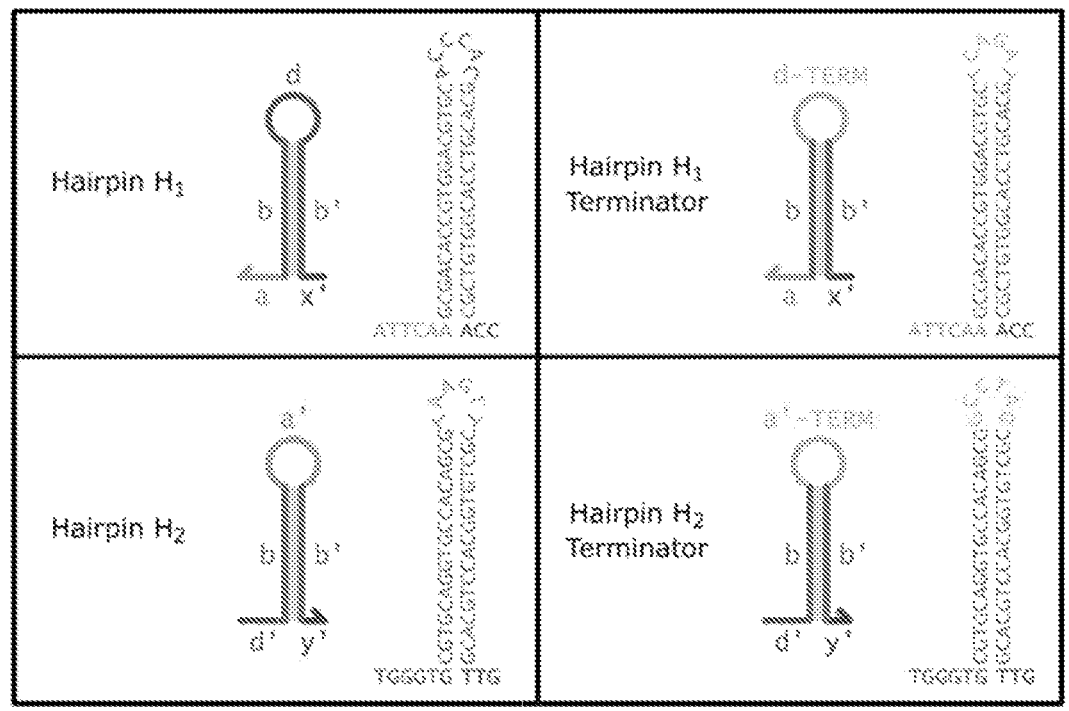

FIG. 26

System 1 Strands

| DNA Strand | Sequence |
|---|---|
| S1-C | /5ACryd/TAAGTTCGCTGTGGCACCTGCACG |
| S1-C' | /5ACryd/CAACGTGCAGGTGCCACAGCG |
| S1-H1 | CGCTGTGGCACCTGCACGCACCCACGTGCAGGTGCCACAGCGAACTTA |
| S1-H2 | TGGGTGCGTGCAGGTGCCACAGCGTAAGTTCGCTGTGGCACCTGCACGTTG |
| S1-H1$_T$ | CGCTGTGGCACCTGCACGTAGACTCGTGCAGGTGCCACAGCGAACTTA |
| S1-H2$_T$ | TGGGTGCGTGCAGGTGCCACAGCGGCCTAGCGCTGTGGCACCTGCACGTTG |
| S1-H1_FAM | /56-FAM/<br>CGCTGTGGCACCTGCACGCACCCACGTGCAGGTGCCACAGCGAACTTA |
| Control Hairpin | GCTATCTAGCATCGCACGCTCTTTTTTGAGCGTGCGATGCTAGATGCGTAC |

System 2 Strands

| DNA Strand | Sequence |
|---|---|
| S2-C | /5ACryd/CTGTCTGCCTACCACTCCGTTGCG |
| S2-C' | /5ACryd/ATTCGCAACGGAGTGGTAGGC |
| S2-H1 | GCCTACCACTCCGTTGCGGAACCTCGCAACGGAGTGGTAGGCAGACAG |
| S2-H2 | AGGTTCCGCAACGGAGTGGTAGGCCTGTCTGCCTACCACTCCGTTGCGTTG |
| S2-H1$_T$ | GCCTACCACTCCGTTGCGTCAAGCCGCAACGGAGTGGTAGGCAGACAG |
| S2-H2$_T$ | AGGTTCCGCAACGGAGTGGTAGGCAATCGTGCCTACCACTCCGTTGCGTTG |
| S2-H1_FAM | /56-FAM/<br>GCCTACCACTCCGTTGCGGAACCTCGCAACGGAGTGGTAGGCAGACAG |

System 3 Strands

| DNA Strand | Sequence |
|---|---|
| S3-C | /5ACryd/GGAACTCGGCAGTCGTCCAAGCGA |
| S3-C' | /5ACryd/ATCTCGCTTGGACGACTGCCG |
| S3-H1 | CGGCAGTCGTCCAAGCGATACGGTCGCTTGGACGACTGCCGAGTTCC |
| S3-H2 | GCCGTATCGCTTGGACGACTGCCGGGAACTCGGCAGTCGTCCAAGCGAGAT |
| S3-H1$_T$ | CGGCAGTCGTCCAAGCGACGAGTTCGCTTGGACGACTGCCGAGTTCC |
| S3-H2$_T$ | GCCGTATCGCTTGGACGACTGCCGAGATCCGGCAGTCGTCCAAGCGAGAT |

FIG. 26 continued

System 4 Strands

| DNA Strand | Sequence |
|---|---|
| S4-C | /5ACryd/ATCGGACCAGCACTTCGCCTACGG |
| S4-C' | /5ACryd/TGACCGTAGGCGAAGTGCTGGATG |
| S4-H1 | CATCCAGCACTTCGCCTACGGCTCTACCCGTAGGCGAAGTGCTGGTCCGAT |
| S4-H2 | GTAGAGCCGTAGGCGAAGTGCTGGATCGGACCAGCACTTCGCCTACGGTCA |
| S4-H1$_T$ | CATCCAGCACTTCGCCTACGGAAGGTGCCGTAGGCGAAGTGCTGGTCCGAT |
| S4-H2$_T$ | GTAGAGCCGTAGGCGAAGTGCTGGTGTATGCCAGCACTTCGCCTACGGTCA |

FIG. 34

Programmable Hydrogels

- a network of polymer chains that are hydrophilic forming that expand or contract in response to a specific nucleic acid stimulus may be use in the following applications:

- 3D matrix cell culture
  - Wound healing
  - Hydrogels
  - Contacts
  - Bio-sensor

FIG. 35

Stimuli used to expand and contract programmable hydrogels

- Chemical stimuli: pH, ions, oxidant
- Physical stimuli: light, temperature, ultrasound, magnetic field
- Biomolecular stimuli including nucleic acids such as DNA hairpins and reversal strands

FIG. 36

DNA as stimuli

- programmable at molecular level
- can be used to build hydrogel as biopolymer

- DNA hydrogels—build by polymer and DNA, respond to DNA signals

FIG. 37
- DNA Responsive Hydrogel
- Crosslink expansion enables more swelling with DNA hybridization chain reaction (HCR)
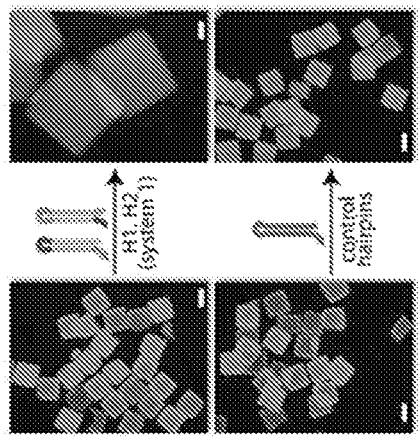
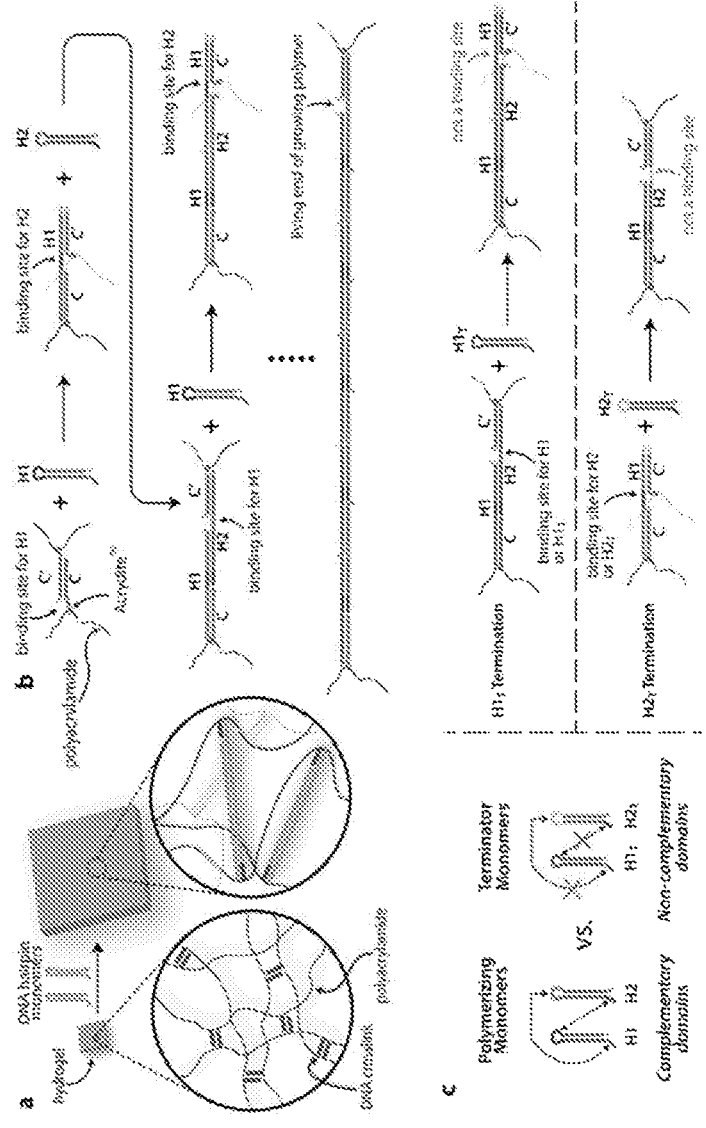

- DNA hydrogel robot
  - Senses DNA signals that lead to structure changes such as expansion and/or contraction
  - The gels reversibly move and/or change structure (contraction and/or expansion)

- Fabrication of hydrogels
  - Photopattern using Cr mask, bilayers or more

- Swelling Experiments
  - Conduct Characterization: microscope and gel imager
    - Use Matlab to create scripts for taking series of pics
    - Use Matlab to crop and sort pics, analyze the size change and create curves, make videos
    - Or use ImageJ to manually measure the sizes Olympus IX73 optical Syngene GBox EF2 gel imager ImageJ FIG. 44
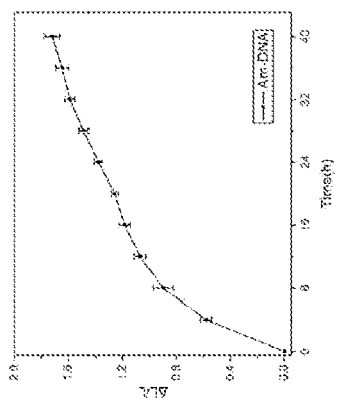
Am-1.154mMDNA Swelling
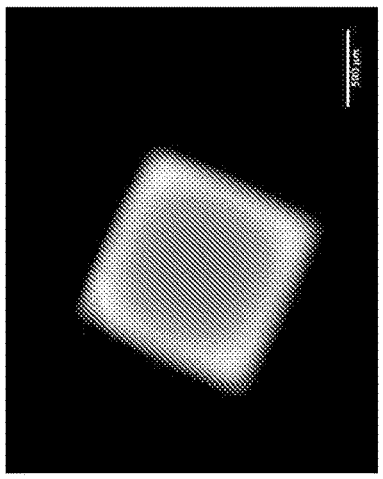
Am-co-BIS
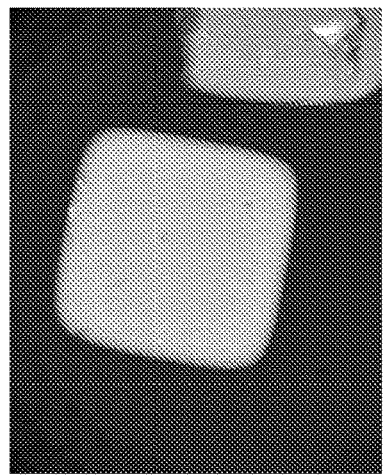
Am-co-DNA
- Repeat Am-co-DNA gels results
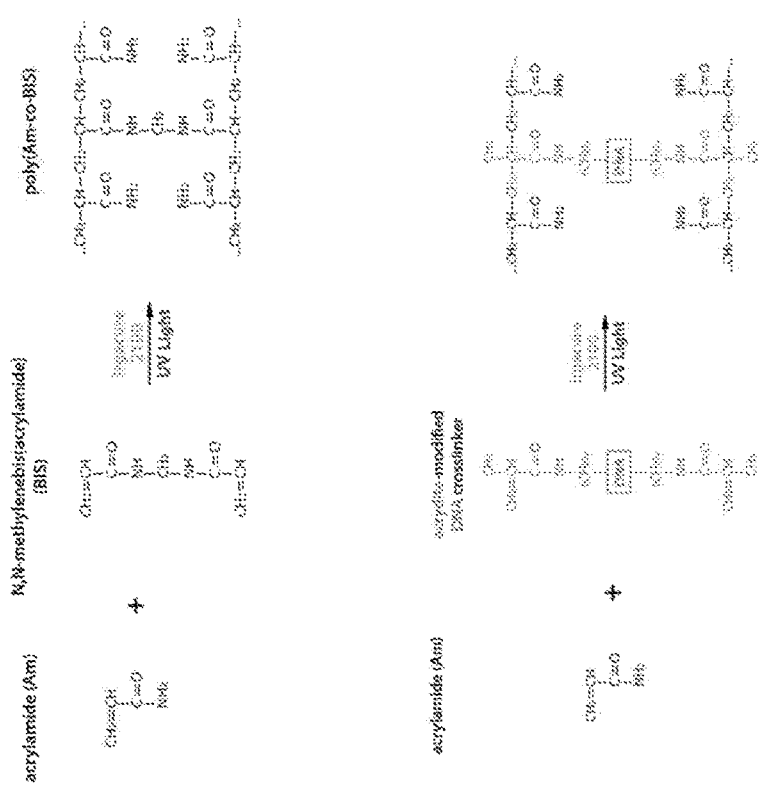

- Add BIS to an AM-DNA gel and making Am-co-BIS-co-DNA gels
  - Expect stiffer gel, less swelling Am-DNA | Am-2mMBIS-1.154mMDNA | Am-5mMBIS-1.154mMDNA FIG. 46
- Swelling of Am-co-DNA-co-BIS gels
- less swelling comparing to Am-DNA
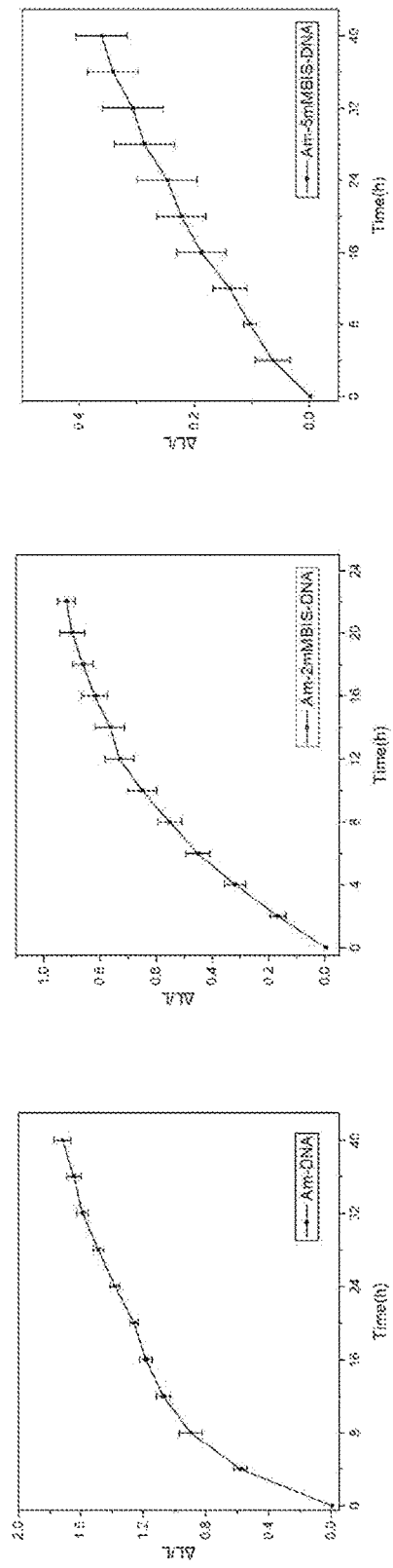
Am-1.154mMDNA   Am-1.154mMDNA Am-5mMBIS-1.154mMDNA
Am-2mMBIS-1.154mMDNA
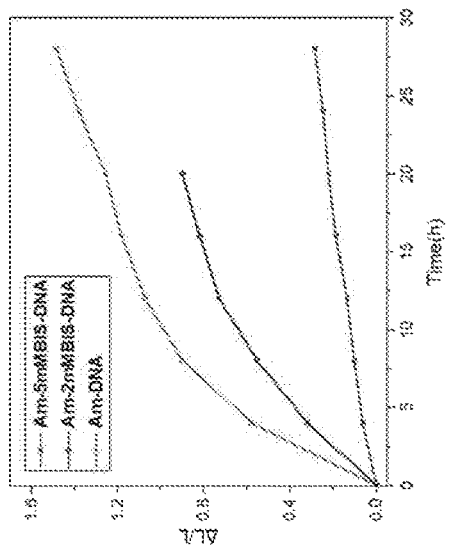
Comparison

FIG. 47
- PEGDA gels
  - Poly(ethylene glycol) diacrylate
  - Better biocompatibility, useful in biomedical applications
  - Self-crosslinking, forms a hydrogel without DNA crosslinks
  - Different MW → different solvent swollen, modulus
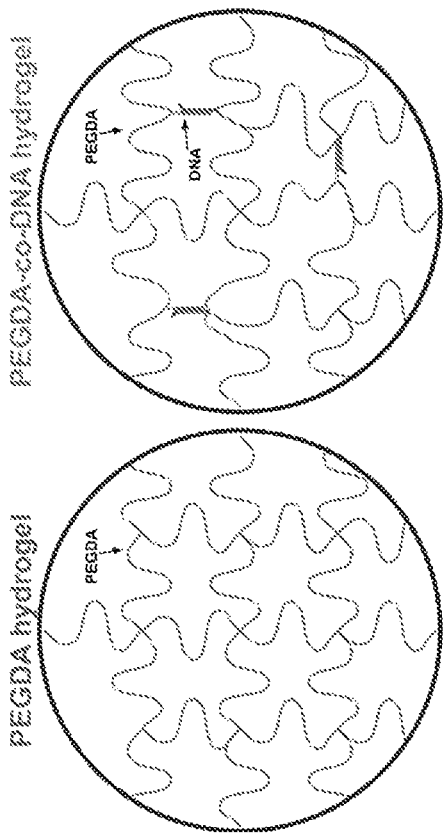
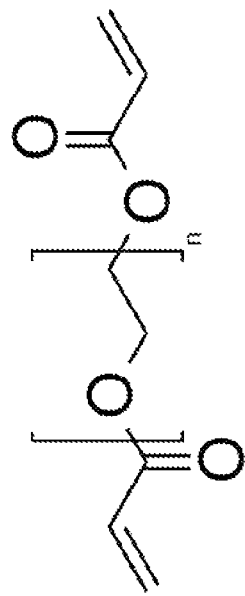

FIG. 48
- PEGDA gels, *optimize recipe* for photopattern
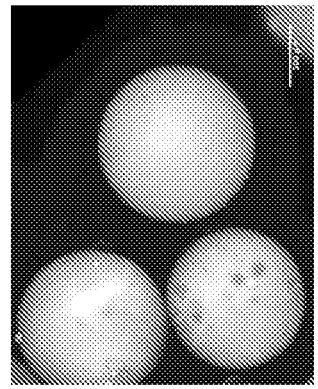
PEGDA10k particles
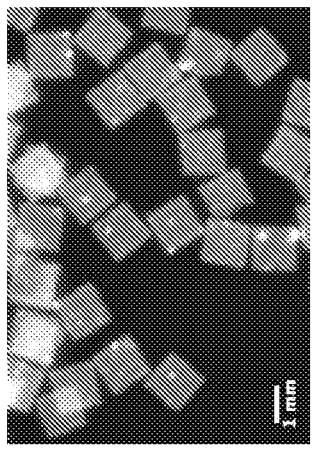
PEGDA575 squares
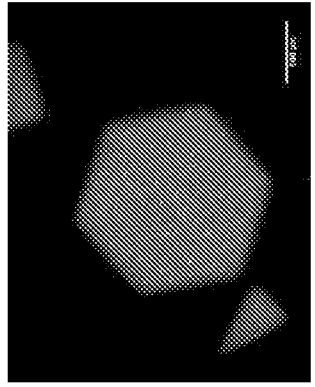
PEGDA10k
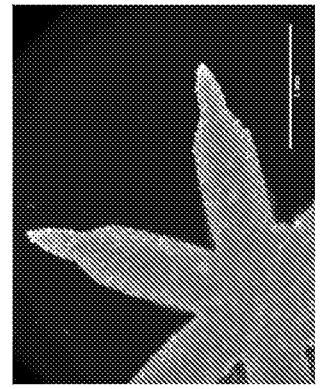
PEGDA10k
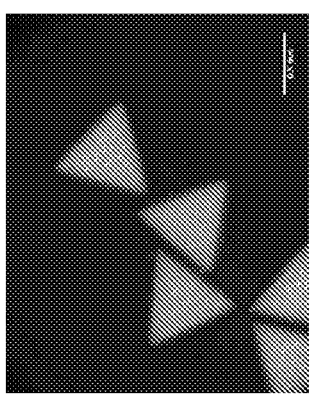
PEGDA10k-DNA
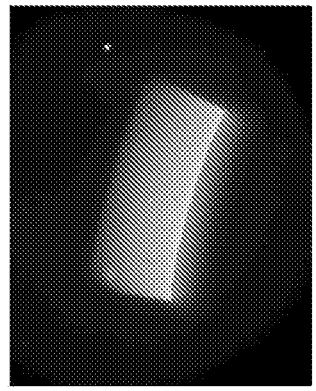
PEGDA10k-DNA cubes, side view

FIG. 49
- PEGDA575-DNA gel doesn't swell
  - DNA crosslink/PEGDA crosslink is about 0.6%
  - If change to PEGDA10K: 11.54%
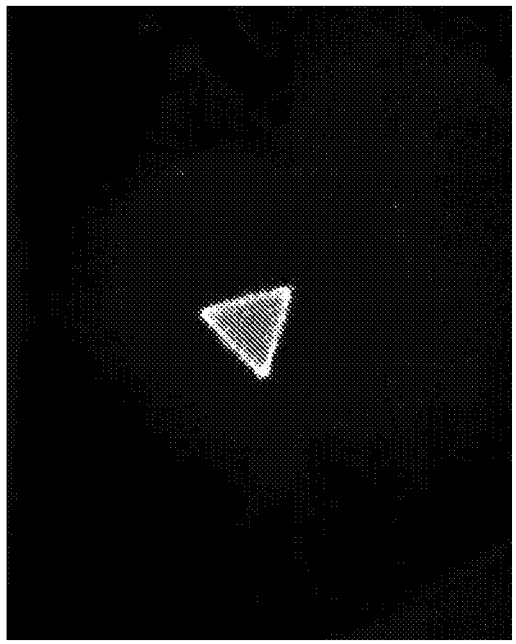
72h
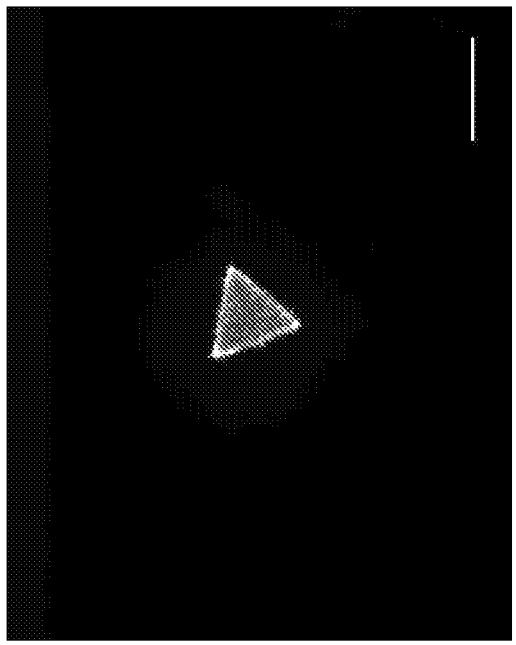
0h FIG. 51
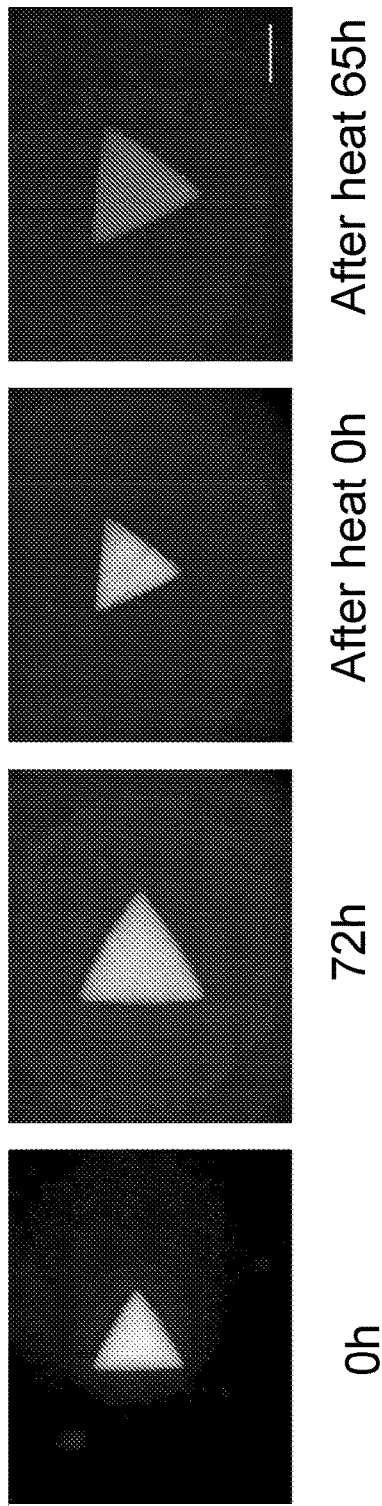
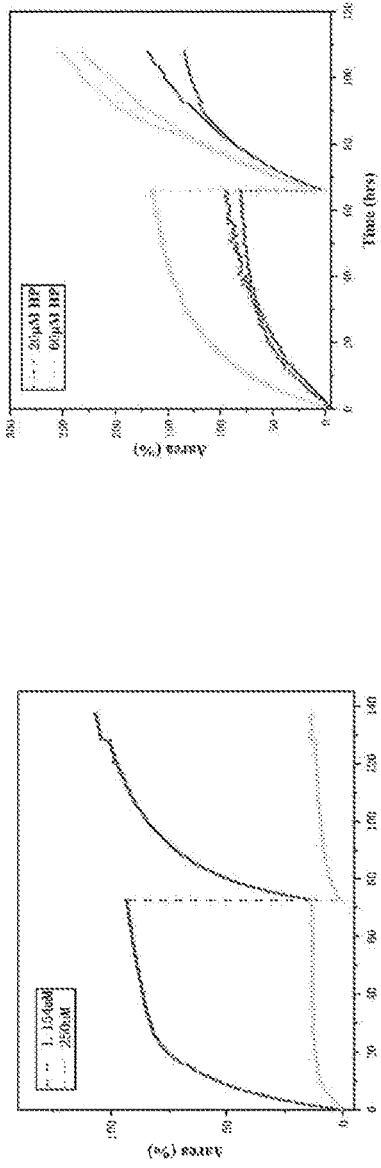

- GelMA gels
- Gelatin methacrylate
- Biocompatible, perfect for cells!
- Different 'bloom', methacrylate ratio changes the gel FIG. 54
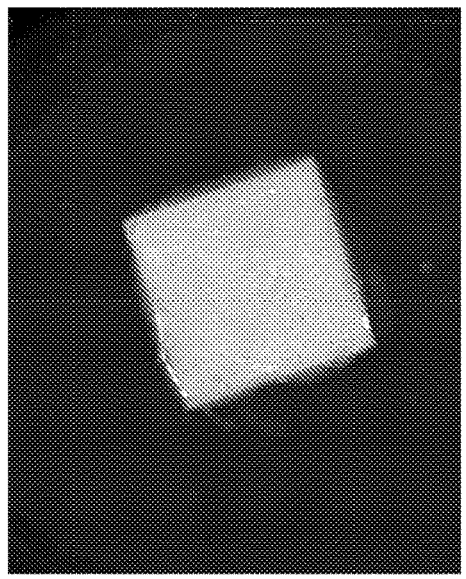
5%GelMA-1.154mM DNA
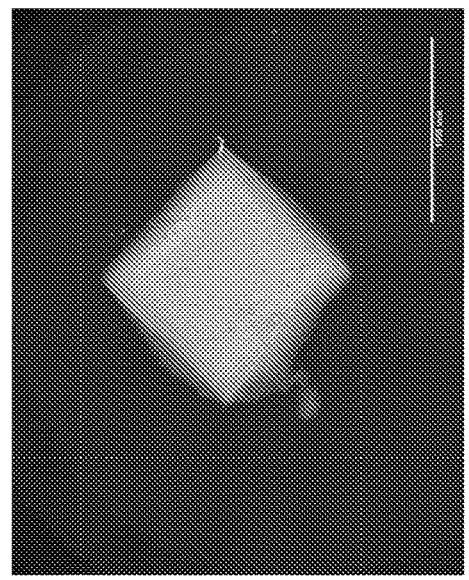
5%GelMA-no DNA
• Expandable GelMA gels
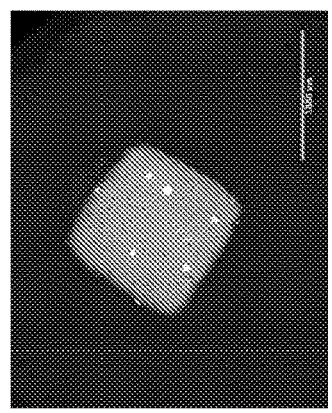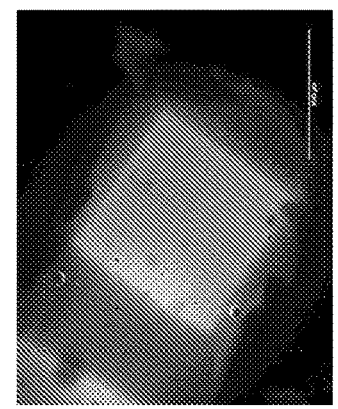

FIG. 58
Am-DNA-Alginate gels
- Fabrication process: 3 times crosslinking, complex
- Photopattern→ Mg$^{2+}$ buffer wash& release the gels→ soak in Ca$^{2+}$/Mg$^{2+}$ buffer for 1day, heat to 50° C in the first 1h
- Swelling: disappear quickly
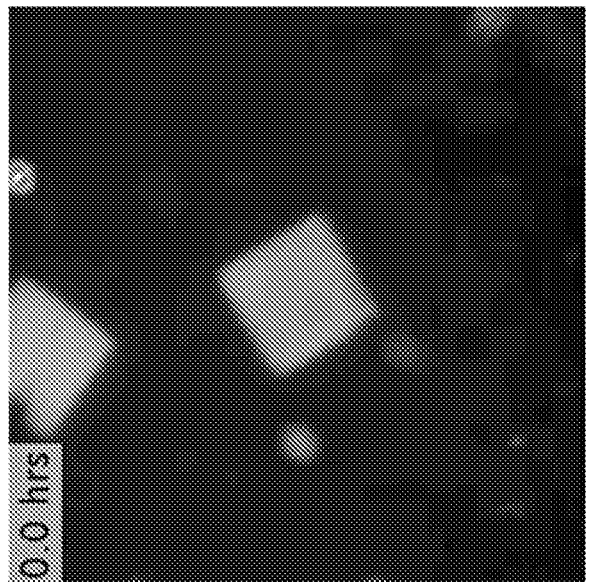
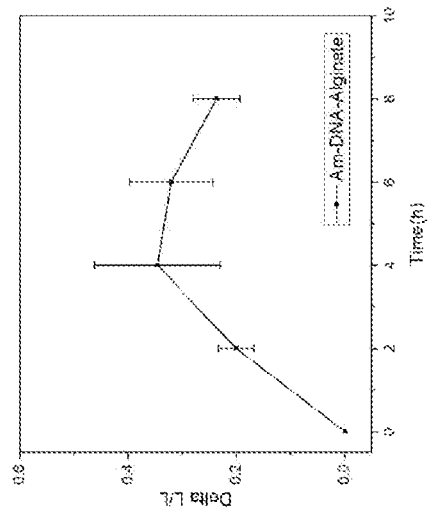

FIG. 59
- Am-DNA-Alginate gel
- Heat to 37° C instead of 50° C for 12 hrs
Before heat
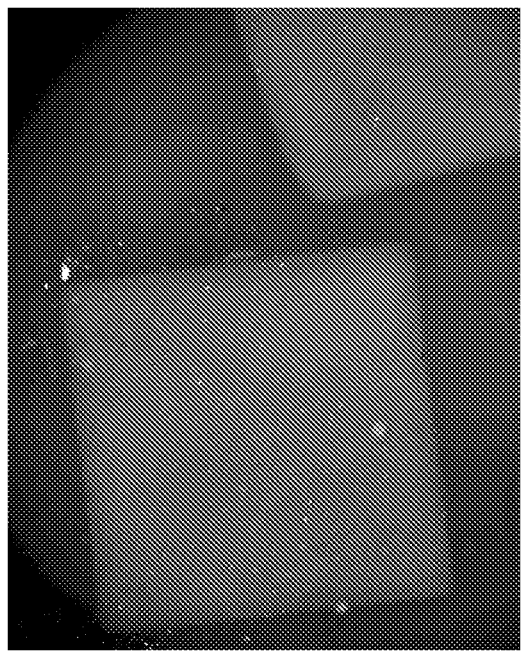
After heat, ~100um larger, pores FIG. 60
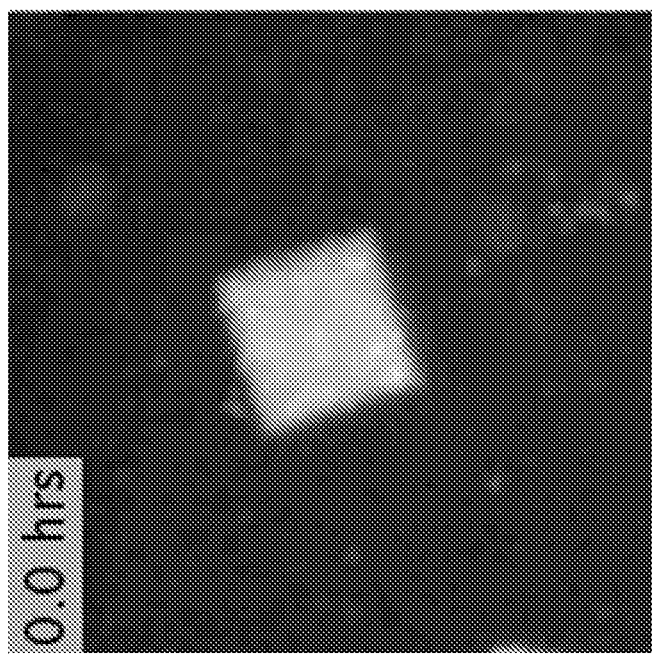
37° C 12hr
• Am-DNA-Alginate gel swelling
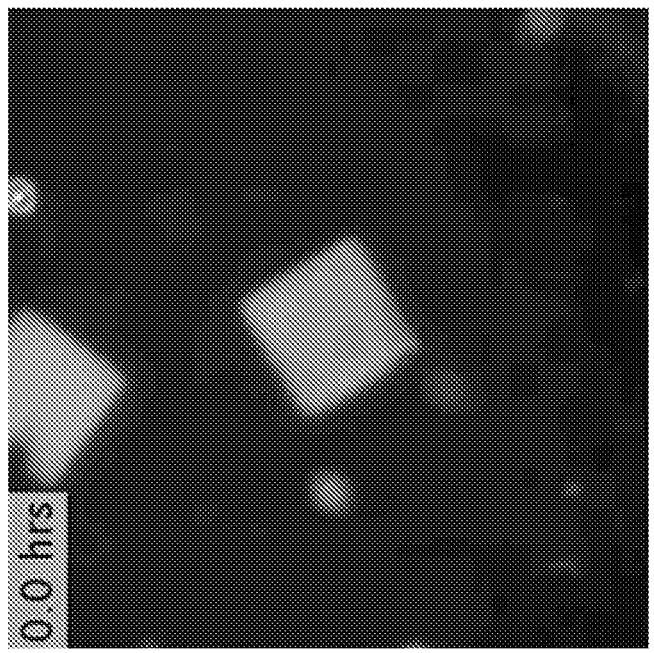
50° C 1hr FIG. 61
- Am-DNA-Alginate gel swelling
  - 37° C one similar to Am-DNA
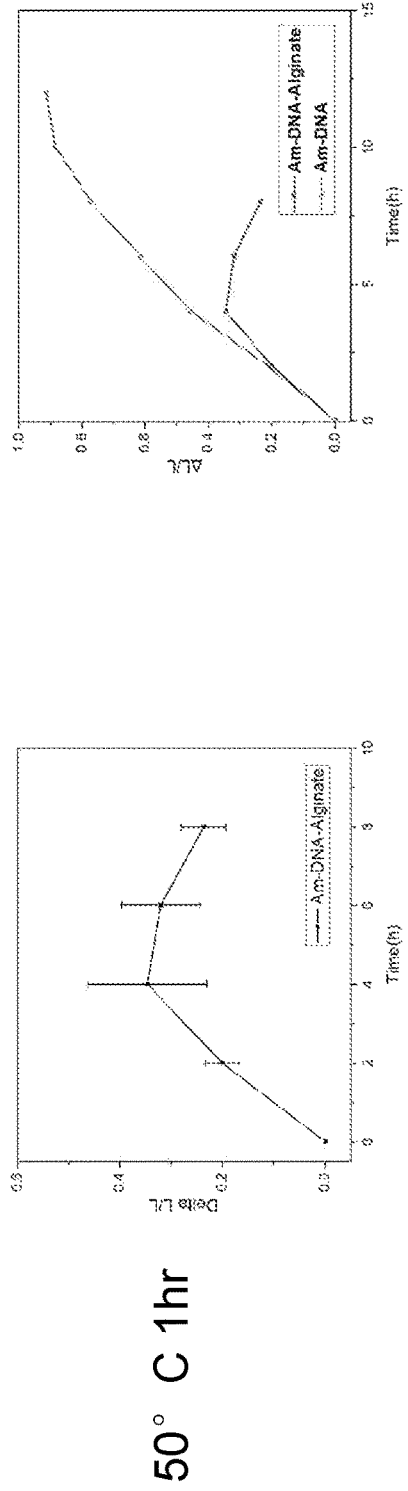
50° C 1hr
37° C 12hr
Compare with Am-DNA
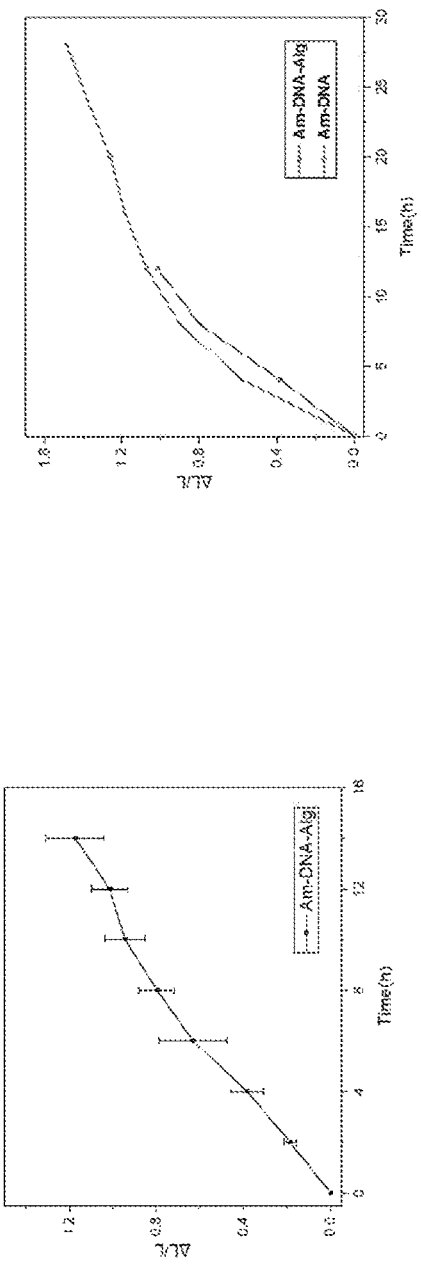

FIG. 62
- Am-DNA-Alginate gel stability
- Preserved for ~2 weeks
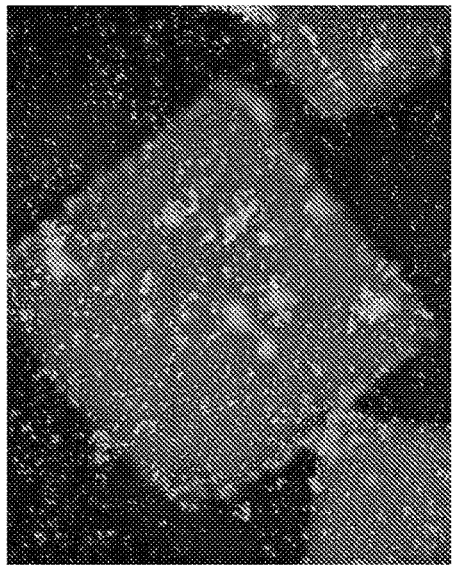
Red chanel: rhod
Green chanel: bright field
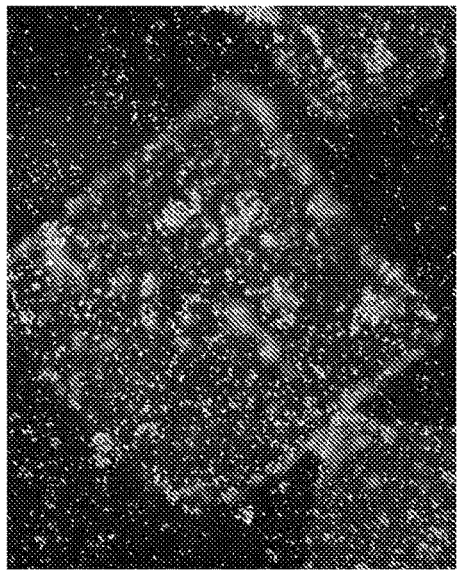
Bright field
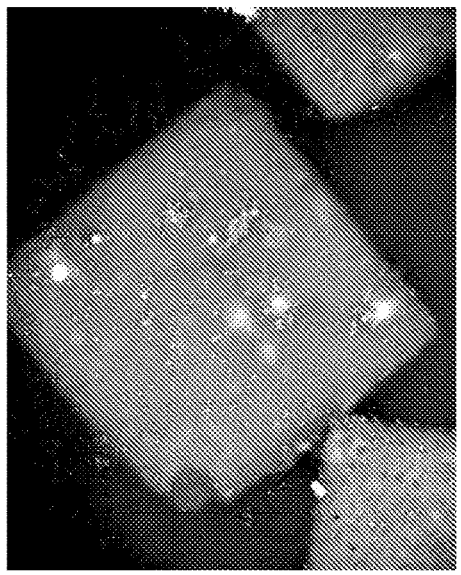
Rhod

SEQUENCE LISTING

<160> NUMBER OF SEQ ID NOS: 71

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 1
taagttcgct gtggcacctg cacg                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 2
caacgtgcag gtgccacagc gtgg                                          24

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccacgctgtg gcacctgcac gcacccacgt gcaggtgcca cagcgaactt a        51

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgggtgcgtg caggtgccac agcgtaagtt cgctgtggca cctgcacgtt g        51

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccacgctgtg gcacctgcac gtagactcgt gcaggtgcca cagcgaactt a        51

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgggtgcgtg caggtgccac agcggcctag cgctgtggca cctgcacgtt g        51

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' 6-FAM-modified

<400> SEQUENCE: 7
ccacgctgtg gcacctgcac gcacccacgt gcaggtgcca cagcgaactt a        51

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctatctagc atcgcacgct cttttttgag cgtgcgatgc tagatgcgta c        51

<210> SEQ ID NO 9
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 9
ctgtctgcct accactccgt tgcg                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 10
attcgcaacg gagtggtagg cttt                                          24

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaagcctacc actccgttgc ggaacctcgc aacggagtgg taggcagaca g            51

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aggttccgca acggagtggt aggcctgtct gcctaccact ccgttgcgtt g            51

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaagcctacc actccgttgc gtcaagccgc aacggagtgg taggcagaca g            51

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aggttccgca acggagtggt aggcaatcgt gcctaccact ccgttgcgtt g            51

<210> SEQ ID NO 15
```

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' 6-FAM-modified

<400> SEQUENCE: 15
aaagcctacc actccgttgc ggaacctcgc aacggagtgg taggcagaca g          51

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 16
ggaactcggc agtcgtccaa gcga                                         24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 17
atctcgcttg gacgactgcc gtat                                         24

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atacggcagt cgtccaagcg atacggctcg cttggacgac tgccgagttc c           51

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gccgtatcgc ttggacgact gccgggaact cggcagtcgt ccaagcgaga t           51

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 20
atacggcagt cgtccaagcg actgagttcg cttggacgac tgccgagttc c         51

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gccgtatcgc ttggacgact gccgcagatc cggcagtcgt ccaagcgaga t         51

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 22
atcggaccag cacttcgcct acgg                                       24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 23
tgaccgtagg cgaagtgctg gatg                                       24

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
catccagcac ttcgcctacg gctctacccg taggcgaagt gctggtccga t         51

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtagagccgt aggcgaagtg ctggatcgga ccagcacttc gcctacggtc a         51

<210> SEQ ID NO 26
<211> LENGTH: 51
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 26
catccagcac ttcgcctacg gaaggtgccg taggcgaagt gctggtccga t              51

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtagagccgt aggcgaagtg ctggtgtatg ccagcacttc gcctacggtc a              51

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 28
acaacgtgca ggtgccacag cgtgga                                          26

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tccgcgctgt ggcacctgca cgcacccacg tgcaggtgcc acagcgaact ta             52

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tgggtgcgtg caggtgccac agcgtaagtt cgctgtggca cctgcacgtt gt             52

<210> SEQ ID NO 31
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tccgcgctgt ggcacctgca cgaaacggcg tgcaggtgcc acagcgaact ta             52

<210> SEQ ID NO 32
<211> LENGTH: 52
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 32
tgggtgcgtg caggtgccac agcgcgacaa cgctgtggca cctgcacgtt gt         52

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 33
gtacaacgtg caggtgccac agcgtggatc                                  30

<210> SEQ ID NO 34
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gatccgcgct gtggcacctg cacgcaccca cgtgcaggtg ccacagcgaa ctta       54

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgggtgcgtg caggtgccac agcgtaagtt cgctgtggca cctgcacgtt gtac       54

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gatccgcgct gtggcacctg cacgaaacgg cgtgcaggtg ccacagcgaa ctta       54

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgggtgcgtg caggtgccac agcggcctag cgctgtggca cctgcacgtt            50

<210> SEQ ID NO 38
<211> LENGTH: 20

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
acggaggtgt atgcaatgtc                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
catgcttagg gacgactgga                                               20

<210> SEQ ID NO 40
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tccagtcgtc cctaagcatg tgttcgacgg tacaagaaga gggttacgct aatgagtgct   60
gacattgcat acacctccgt a                                             81

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
agcactcatt agcgtaaccc tcttcttgta ccgtcgaaca gatagagctg              50

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 42
ctctatctat ccatcaccct caccttac                                      28

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 43
ggtgtaaggt gagggtgatg gtaa                                          24

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ttaccatcac cctcacctta cttgtagatt ggtaaggtga gggtgatgga tagatagag    59

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
caatctacaa gtaaggtgag ggtgatggct ctatctatcc atcaccctca ccttacacc    59

<210> SEQ ID NO 46
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttaccatcac cctcacctta cttgtagatg taaggtgagg gtgatggata gatag        55

<210> SEQ ID NO 47
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atctacaagt aaggtgaggg tgatggctat ctatccatca ccctcacctt acacc        55

<210> SEQ ID NO 48
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttaccatcac cctcacctta cttgtaggta aggtgagggt gatggataga t            51

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ctacaagtaa ggtgagggtg atggatctat ccatcaccct caccttacac c    51

<210> SEQ ID NO 50
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccacgctgtg gcacctgcac gcacccacgt gcaggtgcca cagcgaactt aatgattgtg    60
tatagt    66

<210> SEQ ID NO 51
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agttaagaga atgattgggt gcgtgcaggt gccacagcgt aagttcgctg tggcacctgc    60
acgttg    66

<210> SEQ ID NO 52
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ccacgctgtg gcacctgcac gcacccattc gtgcaggtgc cacagcgaac ttaatgattg    60
tgtatagt    68

<210> SEQ ID NO 53
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
agttaagaga atgattgggt gcgtgcaggt gccacagcgt taagttcgc tgtggcacct    60 gcacgttg    68

<210> SEQ ID NO 54
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ccacgctgtg gcacctgcac gcacccattt ttcgtgcagg tgccacagcg aacttaatga    60
ttgtgtatag t    71

<210> SEQ ID NO 55
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
agttaagaga atgattgggt gcgtgcaggt gccacagcgt tttttaagtt cgctgtggca      60
cctgcacgtt g                                                          71

<210> SEQ ID NO 56
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
actatacaca atcattaagt tcgctgtggc acctgcacg                            39

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
cgctgtggca cctgcacgca cccaatcatt ctcttaact                            39

<210> SEQ ID NO 58
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
aaagcctacc actccgttgc ggaacctcta agcgcaacgg agtggtaggc agacaggtaa      60
ggtaagatag g                                                          71

<210> SEQ ID NO 59
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
gggtagtgtg atgtgaggtt ccgcaacgga gtggtaggcc taagctgtct gcctaccact      60
ccgttgcgaa t                                                          71

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 60
cctatcttac cttacctgtc tgcctaccac tccgttgcg                              39

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gcctaccact ccgttgcgga acctcacatc acactaccc                              39

<210> SEQ ID NO 62
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ttaccatcac cctcaccttα cttgtagatg taaggtgagg gtgatggata gatagggtag       60
gtgaatggga                                                              70

<210> SEQ ID NO 63
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tatgagtgag ttaggatcta caagtaaggt gagggtgatg gctatctatc catcaccctc       60
accttacacc                                                              70

<210> SEQ ID NO 64
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ttaccatcac cctcaccttα cttgtagatt ttttgtaagg tgagggtgat ggatagatag       60
ggtaggtgaa tggga                                                        75

<210> SEQ ID NO 65
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tatgagtgag ttaggatcta caagtaaggt gagggtgatg gtttttctat ctatccatca       60
ccctcacctt acacc                                                        75
```

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
attcaagcga caccgtggac gtgcacccac gcacgtccac ggtgtcgcac c          51

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
attcaagcga caccgtggac gtgctcagat gcacgtccac ggtgtcgcac c          51

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 68
taagttcgct gtggcacctg cacg                                        24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 69
caacgtgcag gtgccacagc gtgg                                        24

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' acrydite-modified

<400> SEQUENCE: 70
ctctatctat ccatcaccct caccttac                                    28

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: 5' acrydite-modified

<400> SEQUENCE: 71
ggtgtaaggt gagggtgatg gtaa                                                  24
```

PROGRAMMABLE SOFT ROBOT

CROSS-REFERENCE TO RELATED APPLICATIONS

This application is a 35 U.S.C. § 371 U.S. national entry of International Application PCT/US2018/049005, having an international filing date of Aug. 31, 2018, which claims the benefit of U.S. Provisional Application No. 62/553,751, filed Sep. 1, 2017, the content of each of the aforementioned applications is herein incorporated by reference in their entirety.

STATEMENT OF GOVERNMENTAL INTEREST

This invention was made with government support under grant no. W911NF-15-1-0490 awarded by ARMY/ARO. The government has certain rights in the invention.

SEQUENCE LISTING

The instant application contains a Sequence Listing which has been submitted electronically in ASCII format and is hereby incorporated by reference in its entirety. Said ASCII copy, created on Aug. 21, 2018, is named P14626-02_SL.txt and is 18,621 bytes in size.

BACKGROUND OF THE INVENTION

A common design for smart materials and devices is a patterned architecture in which a specific chemical or physical stimulus produces swelling or shrinking of one or more material regions. Local, addressable control over this process can enable the multistate shape changes required for metamorphic materials or soft robots. Such control can be achieved by embedding wires that direct local mechanical deformations. However, wires add physical bulk and require batteries or tethering, limiting the scope of their operation.

Chemomechanically responsive materials present advantages in terms of autonomy, versatility, programmability, device integration and miniaturization as compared to materials with embedded wires. Chemicals can diffuse over large distances and into small or tortuous spaces, and the huge number of chemicals that can be synthesized offers unprecedented tunability and specificity.

Addressable control comparable to that in wired systems cannot be currently achieved by wire-free stimuli such as temperature, light, electromagnetic signals or pH. There is a commercial need to develop a wire-free responsive materials made of biomolecules

SUMMARY OF THE INVENTION

The inventor's focused on developing wire-free responsive materials beginning with building a library of biomolecules to achieve addressable control, such that each of a combinatorial variety of biomolecular species would direct the swelling of a specific material domain. Analogous to the way biomolecular stimuli would enable complex sensing, signal processing and feedback within biological cells and tissues.

One embodiment of the present invention is a programmable gel comprising: a first polymer comprising a first crosslink nucleic acid sequence; a second polymer comprising a second crosslink nucleic acid sequence; a first polymerizing hairpin capable of binding to the first crosslink nucleic acid sequence; a second polymerizing hairpin capable of binding to the second crosslink nucleic acid sequence; and a terminating hairpin capable of terminating polymerization. A suitable first crosslink nucleic acid sequence may comprise a first stem sequence, a first anchor B sequence, and a first anchor A sequence, for example. A suitable second crosslink nucleic acid sequence may comprise a second stem sequence that is complementary to the first stem sequence and a first dock A sequence; for example. A suitable first polymerizing hairpin may comprise the first stem sequence and the second stem sequence, a first dock B sequence, a second anchor A sequence that is complementary to the first anchor A sequence, and a second dock A sequence that is complementary to the first dock A sequence, for example. A suitable second polymerizing hairpin may comprise the first stem sequence, the second stem sequence, a second dock B sequence that is complementary to the first dock B sequence, the first dock A sequence; and the first anchor B sequence; for example. A suitable terminating hairpin may comprise the first stem sequence, the second stem sequence, the second dock A sequence, the second anchor A sequence and a terminating sequence. The programmable gel of claim 2 wherein the stem nucleic acid sequences comprise from 8 to 50 nucleic acids each, the dock A and dock B sequences comprise up to 10 nucleic acids each, and the anchor A and anchor B nucleic acid sequences comprise up to 10 nucleic acids each.

Another embodiment of the present invention is a method of making a programmable gel comprising: providing a gel comprising a first polymer comprising a first crosslink nucleic acid sequence; a second polymer comprising a second crosslink nucleic acid sequence wherein the first polymer and the second polymer are crosslinked by the first and second crosslink nucleic acid sequences; and adding a first polymerizing hairpin, a second polymerizing hairpin; and a terminating hairpin to the gel to produce a programmable gel; wherein a concentration ratio of the first polymerizing hairpin, the second polymerizing hairpin, and terminating hairpins are adjusted prior to addition to gel to control the timing and/or degree of swelling of the programmable gel.

Another embodiment of the present invention is an expandable gel comprising: a first polymer comprising a first crosslink nucleic acid sequence; a second polymer comprising a second crosslink nucleic acid sequence; a first polymerizing hairpin capable of binding to the first cross link nucleic acid sequence; and a second polymerizing hairpin capable of binding to the second crosslink nucleic acid sequence.

Another embodiment of the present invention is a method of making an expandable gel comprising: providing a gel comprising a first polymer comprising a first crosslink nucleic acid sequence; a second polymer comprising a second crosslink nucleic acid sequence that are crosslinked by the first and second crosslink nucleic acid sequences; adding a first polymerizing hairpin and a second polymerizing hairpin; and forming an expanded gel (until the hairpins are used up).

Another embodiment of the present invention is a photo patterning process to pattern gels into precisely-defined architectures comprising: providing a surface comprising a sacrificial layer; applying a collection of monomers, a photo-initiator, and a collection of crosslink nucleic acid sequences capable of binding to the monomers; placing a mask on top of the programmable gel wherein the mask is impenetrable by light and comprises one or more shapes wherein light is able to penetrate through the shapes on the mask; applying light to the mask so that light penetrates the shapes on the mask; polymerizing the monomers; binding the cross link nucleic acids to the monomers; forming a collection of polymers comprising attached nucleic acid sequences wherein the nucleic acid sequences crosslink the polymers and the collection of polymers comprises the one or more shapes; removing the mask; adding a ratio of polymerizing hairpins and terminating hairpins; and creating a gel having one or more precisely-defined architectures. A photopatterning process of the present invention may comprise the step of removing a collection of polymers from the surface prior to adding the ratio of polymerizing hairpins and terminating hairpins.

Any suitable polymer able to work with nucleic acid chemistry may be used in the present invention. Examples include water soluble polymers, polyisoprene, polystyrene, polypropylene, polyvinyl chloride, synthetic rubber, natural rubber, phenol formaldehyde resin (or Bakelite), neoprene, nylon, polyacrylonitrile, PVB, silicone, acrylamide, hydrogels, gelatin, alginate, collagen, cross-linked peptoids or nucleic acid polymers, agarose polysachrides, hyaluronic acid acrylate, cross-linked acrylate, methacrylate, and acrylic acid, as examples.

One embodiment of the present invention are methods of making programmable gels. The methods of the present invention include providing a gel comprising a first polymer comprising a tag. Adding a first polymerizing hairpin, a second polymerizing hairpin, and a terminating hairpin to the gel. Producing a programmable gel that is expanding compared to a reference gel wherein the first polymerizing hairpin, the second polymerizing hairpin and a terminating hairpin have not been added. The gels of the present invention are programmable because the concentration ratio of starting materials are predetermined prior to their addition to a gel so as to control the timing and/or degree of swelling of a programmable gel. For example, a first polymerizing hairpin, a second polymerizing hairpin, and terminating hairpins are adjusted prior to addition to a gel to control the timing and/or degree of swelling of the programmable gel. The expansion and/or the contraction of gels of the present invention occurs by annealing nucleic acid sequences of the present invention. For example a tag is a single stranded nucleic acid such as an RNA or DNA that may include a dock B sequence and a tag anchor A sequence. The first polymerizing hairpin comprises a first stem sequence and a second stem sequence, a first dock B sequence, a second anchor A sequence that is complementary to the first anchor A sequence and a second dock A sequence that is complementary to a first dock A sequence. The first dock B sequence binds to the tag dock B sequence and where the second anchor A sequence binds to the tag anchor A sequence. The second polymerizing hairpin comprises the first stem sequence, the second stem sequence, a second dock B sequence that is complementary to the first dock B sequence, the first dock A sequence; and a first anchor B sequence. The terminating hairpin comprises the first stem sequence, the second stem sequence, the second dock A sequence, the second anchor A sequence and a terminating sequence.

Another embodiment of the present invention are methods of making a programmable gel that expands and contracts. The methods include providing a gel comprising a first polymer comprising a first crosslink nucleic acid sequence and a second polymer comprising a second crosslink nucleic acid sequence. Crosslinking the first polymer and the second polymer by the first and second crosslink nucleic acid sequences and a third crosslinker. Adding a first polymerizing hairpin, a second polymerizing hairpin; and a terminating hairpin to the gel. Producing a programmable gel that expands. Adding a first reversal strand, a second reversal strand to the programmable gel and contracting the gel compared to a reference gel that does not have a first and second reversal strand added. The methods may include a third polymerizing hairpin and fourth polymerizing hairpin are added to the contracted gel and expands the contracted gel forming an expanded contracted gel. The methods may include adding a third reversal strand and a fourth reversal strand to the expanded contracted gel and contracting the expanded, contracted gel. A programmable gel of the present invention may go through many cycles of expansion, contraction, or a combination thereof. Each expansion cycle may use the same polymerizing hairpins as the previous cycle, different polymerizing hairpins, or a combination thereof. Each contraction cycle may use the same reversal strands as the previous cycle, different reversal strands, or a combination thereof. In some methods, a gel is programmable because a concentration ratio of the first polymerizing hairpin, the second polymerizing hairpin, the terminating hairpins, the first reversal strand, and the second reversal strand are adjusted prior to addition to a gel to control the timing and/or degree of swelling and/or contraction of the gel. A suitable third crosslink comprises a physical, ionic, chemical, or nucleic acid crosslink. In some methods of the present invention the first and second polymerizing hairpins, terminating hairpins, and first and second reversal strands are incapable of interacting with the third crosslinker.

As mentioned, the expansion and/or contraction of gels of the present invention occurs by annealing nucleic acid sequences of the present invention. For example, the first and the second reversal strands of the present invention are nucleic acids such as RNA or DNA. In some methods of the present invention the first reversal strand interacts with the first polymerizing hairpin and the second reversal strand interacts with the second polymerizing hairpin.

Another embodiment of the present invention are methods of gel contraction. The methods include providing a gel comprising a first polymer comprising a first crosslink nucleic acid sequence and a second polymer. The second polymer comprises a second crosslink nucleic acid sequence and the first polymer and the second polymer are crosslinked by the first and second crosslink nucleic acid sequences. The gel also includes a third crosslinker, a first polymerizing hairpin, a second polymerizing hairpin, and a terminating hairpin. To this gel is added a first and a second reversal strand that causes the gel to contract when compared to a reference gel that does not include the first and second reversal strand.

FIGS. 1, 25, and 26 are color coded so that the gray region is an example of the stem sequence; the pink region is an example of the dock A sequence; the cyan region is an example of the anchor A sequence; the green region is an example of the anchor B sequence; and the purple is an example of the dock B sequence.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

"Crosslinked nucleic acid sequence" means a double stranded nucleic acid sequence that typically contains anchor, stem, and dock sequences.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

A "reference sequence" is a defined sequence used as a basis for sequence comparison.

By "specifically binds" is meant a nucleic acid that recognizes and binds a second complementary nucleic acid of the invention, but which does not substantially recognize and bind other non-complementary nucleic acid molecules in a sample.

"Tag" means a single stranded nucleic acid sequence that typically contains a dock and stem sequences.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a nucleic acid molecule exhibiting at least 50% identity to a reference nucleic acid sequence. Preferably, such a sequence is at least 60%, more preferably 80% or 85%, and more preferably 90%, 95% or even 99% identical at the nucleic acid sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

BRIEF DESCRIPTION OF THE DRAWINGS

FIG. 1A-1C DNA-directed expansion of DNA-cross-linked polyacrylamide gels. (A) DNA crosslinked polyacrylamide hydrogels (8). Hairpins can insert into crosslinks, inducing hydrogel expansion. (B) Schematic of crosslink C-C' extension by hairpins H1 and H2. Colors indicate domain type and its complement. Thin black lines indicate polyacrylamide. (C) Polymerizing hairpins allow the insertion of additional monomers, while terminator hairpin monomers leave a site that no monomers can interact with.

FIG. 5 Chemistry for synthesizing a poly(Am-co-BIS) or poly(Am-co-DNA) hydrogel. Both poly(Am-co-BIS) and the poly(Am-co-DNA) hydrogels were prepared by standard UV-initiated, radical copolymerization chemistry. In the case of poly(Am-co-DNA) gels, a pre-annealed DNA duplex—with each strand modified at the 5' end with a standard, commercially available, acrydite moiety—was used as a crosslinker. The acrydite-modified DNA strands were obtained from IDT in their lyophillized form.

Figures 3A, 3B, 3C:
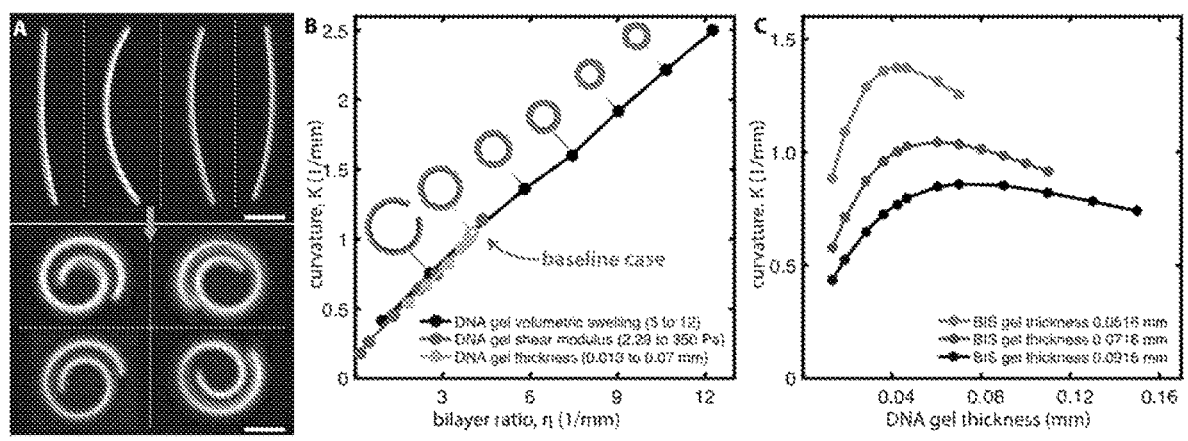
FIG. 3A-3C Shape change mechanics. (A) Fluorescence micrographs of photopatterned hydrogel beams (side views) with a 60 µm thick BIS-crosslinked polyacrylamide layer (green), and a 60 µm thick DNA-crosslinked hydrogel (red) before (top) and after (bottom) sequence-driven curving. Scale bars 1 mm. (B) Computational finite element parameter study of bilayer curvature. The baseline case (white circle) corresponds to experimentally measured bilayer curvature and swelling ratios. The bilayer ratio (Equation 1) captures the effects of the shear moduli, thickness and volumetric swelling ratios of the gel layers. Illustrated bilayers show predicted final shapes for different volumetric swelling ratios. (C) Analytical predictions of curvature change using the design rule $K=C\eta+K_0$, where C and $K_0$ were fit to simulation results B.

This solvent uptake controls the initial size of the gels when DNA is added to induce specific actuation. Differential swelling of poly(Am-co-BIS) and poly(Am-co-DNA) gels due to solvent uptake caused the bilayers in FIG. 3 to curve slightly before DNA-driven actuation, as seen in FIG. 3A. To measure the extent of swelling through solvent uptake for each gel type, poly(Am-co-BIS) and poly(Am-co-DNA) hydrogels were photopatterned as described in Methods. The poly(Am-co-BIS) gels were labeled with rhodamine B via copolymerization with acrylamide and BIS, whereas the poly(Am-co-DNA) gels were stained overnight in 2×SYBR Green dye. The gels were then allowed to equilibrate in TAE/$Mg^{2+}$ buffer for 24 hrs. The poly(Am-co-BIS) gels swelled uniaxially due to solvent uptake by an average of 0.12±0.04 (mean±SD, N=5). The poly(Am-co-DNA) gels uniaxially swelled due to solvent uptake by an average of 0.36±0.04 (mean±SD, N=4). Images of sample (a) poly(Am-co-BIS) and (b) poly(Am-co-DNA) gels after 24 hours of equilibration in solvent are shown. The degree of swelling was calculated using pattern dimensions of the photomask as the initial lengths of the gel edges. Scale bars are 1 mm.

Figure 18:
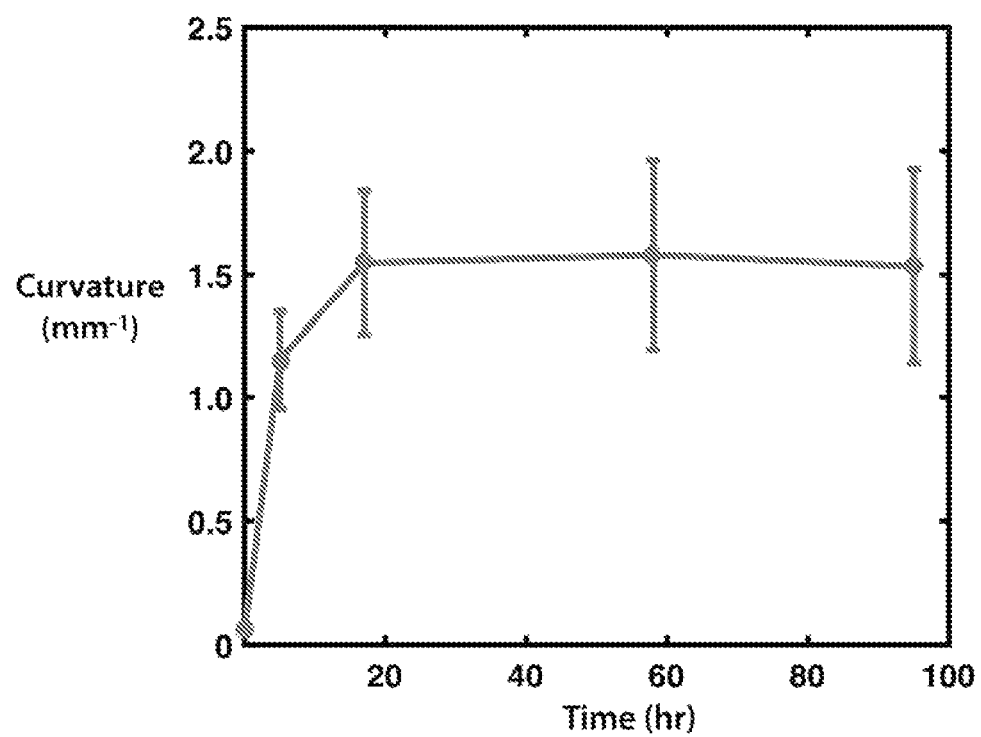

FIG. 18 Kinetics of BIS/DNA bilayer actuation. Gel bilayer architectures comprised of a bottom poly(Am-co-BIS) layer and a top poly(Am-co-DNA) layer were fabricated as described in Methods and FIG. 16. After fabrication, the gel structures were allowed to equilibrate in TAE/$Mg^{2+}$ for at least 24 hours. Next, the samples were placed in 3 mL of 20 µM hairpin solution containing 2% terminator hairpin. The curvature of the samples was monitored via fluorescence microscopy and was measured using ImageJ software. Each of the data points represents measurements from 3 samples. Error bars represent a single standard deviation about the mean swelling value.

Figures 7A, 7B:
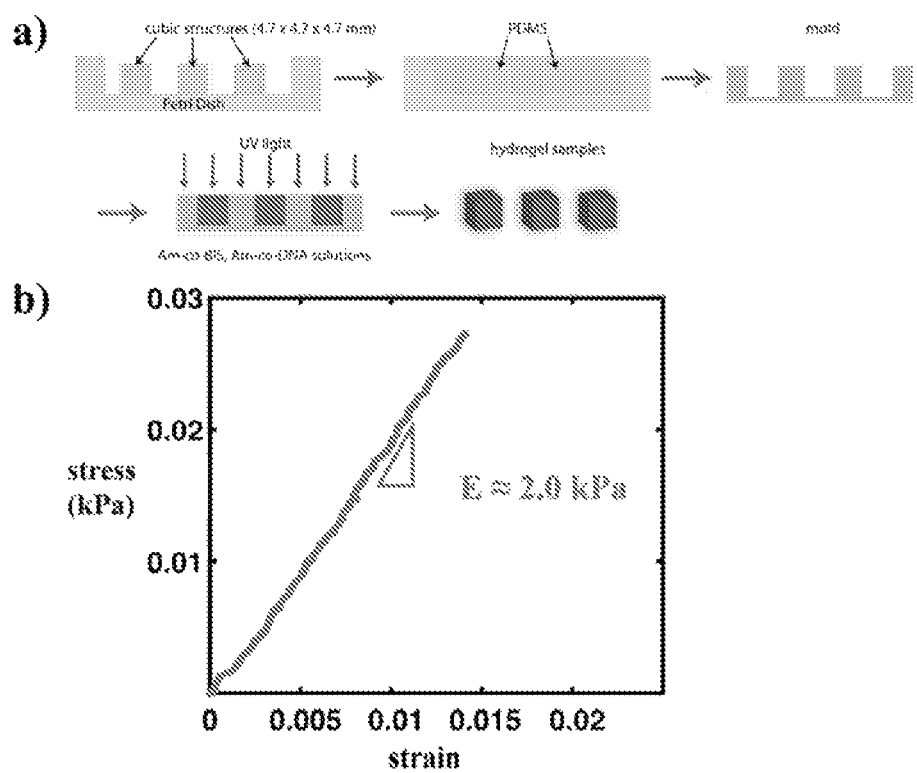
FIG. 7A-7B Micromolding and stress-strain measurements of a poly(Am-co-DNA) hydrogel. To determine the stiffness of the DNA-crosslinked hydrogels used in this study, elastic moduli measurements were obtained for a fully hydrated poly(Am-co-DNA) hydrogel. (A) A PDMS micromold was prepared by mixing base and curing components of Sylgard 184 in a 1:10 volume ratio. The resulting solution was poured over a negative pattern, wooden cubes, in a Petri dish. The mixture was then heated at 70° C. for one hour and allowed to cool to room temperature. The PDMS mold was then peeled off the negative pattern and taken out of the Petri dish. A poly(Am-co-DNA) gel cube sample with dimensions of roughly 4.7×4.7×4.7 mm was prepared by photopolymerization of a system 1 pregel solution in the PDMS mold. The gel was exposed to 365 nm UV light with an intensity of 7.55 mW/cm$^2$ for five minutes to ensure complete curing of the pregel solution. The gel sample was then placed in 3 mL of fresh TAE/Mg$^{+2}$ buffer and was allowed to swell due to solvent uptake to equilibrium over a period of roughly two weeks, with the buffer being replaced approximately every 3 days. (B) The elastic modulus of the DNA gel sample was measured using a controlled force, unconfined compression test at room temperature (Q800 DMA; TA instruments). The applied force on the gel sample was ramped to a maximum static force value of 2 mN at a rate of 1 mN/min. Once the maximum static force was reached, the applied force was ramped down to 0 N at the same rate. Static force and displacement data for the loading portion of the compression test were used to generate true stress and true strain curves for the sample. The elastic modulus was measured as the slope of the best-fit line to the stress-strain curve. Previously D. C. Lin et al. reported that the elastic moduli for a poly(Am-co-DNA) gel ranges from 59 Pa to 11.6 KPa depending on crosslink density (41), consistent with these measurements.
Figure 19:
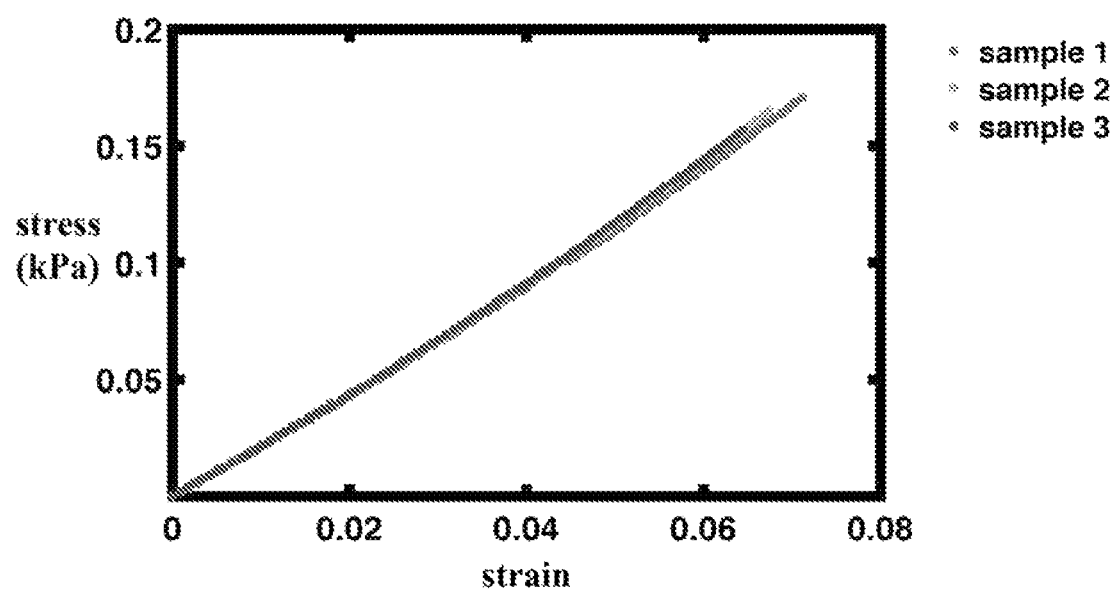

FIG. 19 Measurement of the Young's modulus for poly (Am-co-BIS) hydrogels. Three poly(Am-co-BIS) hydrogel samples, each 8 mm×8 mm×8 mm in size, were fabricated via photopolymerization of 5% Am:BIS (19:1) pregel solution in a previously prepared PDMS mold (see FIG. 7). The hydrogel samples were then placed in 1×TAE/$Mg^{2+}$ for two days to swell to equilibrium via solvent uptake. To obtain elastic moduli values for the gels, the samples were subjected to an unconfined compression, controlled-force deformation test (Q800 DMA, TA instruments). The applied force was increased at a rate of 0.01 N/min until a maximum static force of 0.015 N was reached, after which the load was reduced at the same rate to 0 N. True stress-strain curves were generated from the raw static force and displacement data. Elastic moduli values were calculated as the tangent to the best fit quadratic curve at 1% strain, and were determined to be 2.24 kPa, 2.18 kPa and 2.17 kPa for samples 1, 2 and 3, respectively. They are on the order of previously determined elastic moduli values for poly(Am-co-BIS) gels prepared with similar concentrations of Am and BIS (42).

Figure 20:
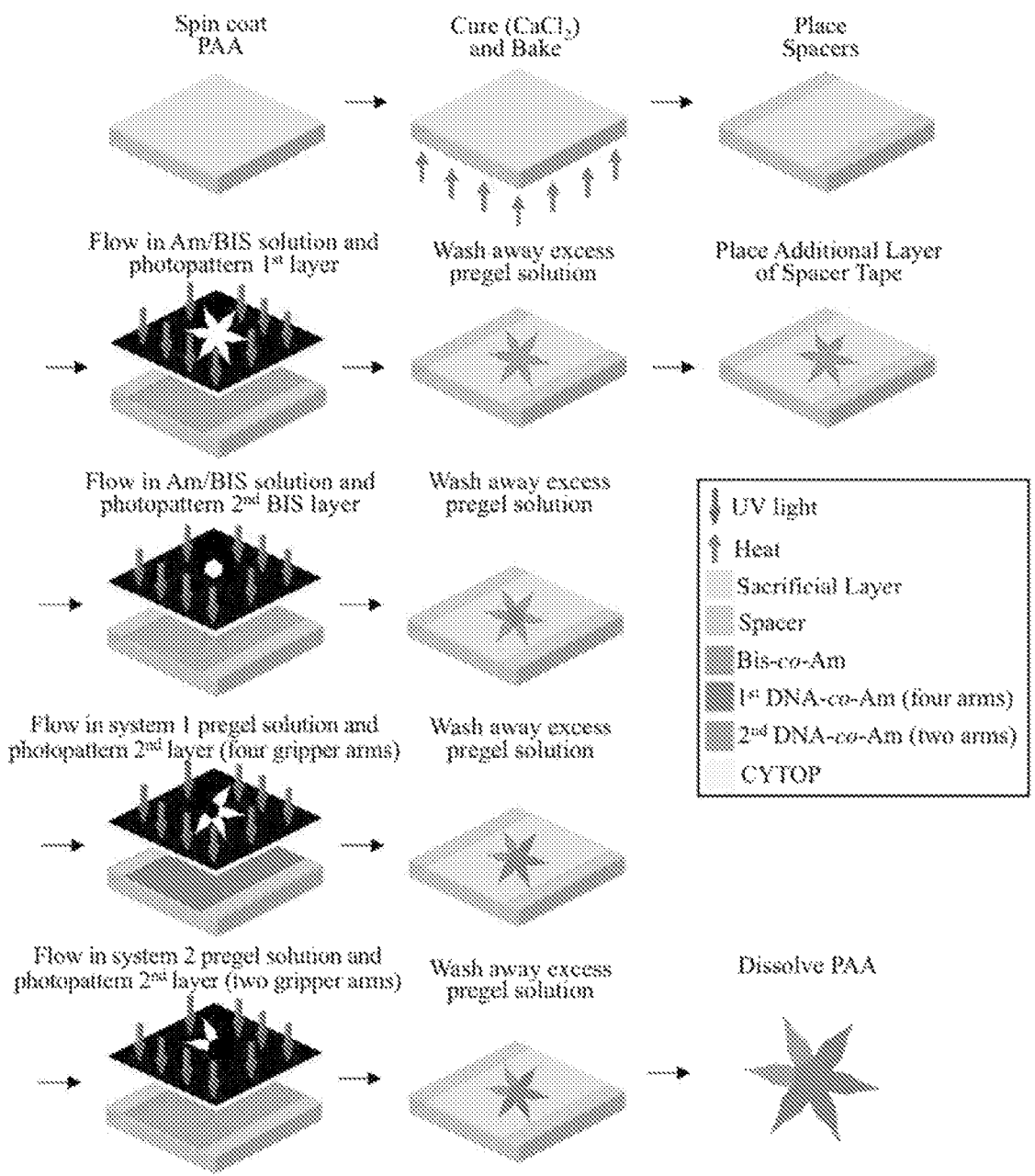

FIG. 20 Flower fabrication. Parameters such as bake temperature/time, spacer thickness and solution concentrations are listed in Methods.

Figure 21:
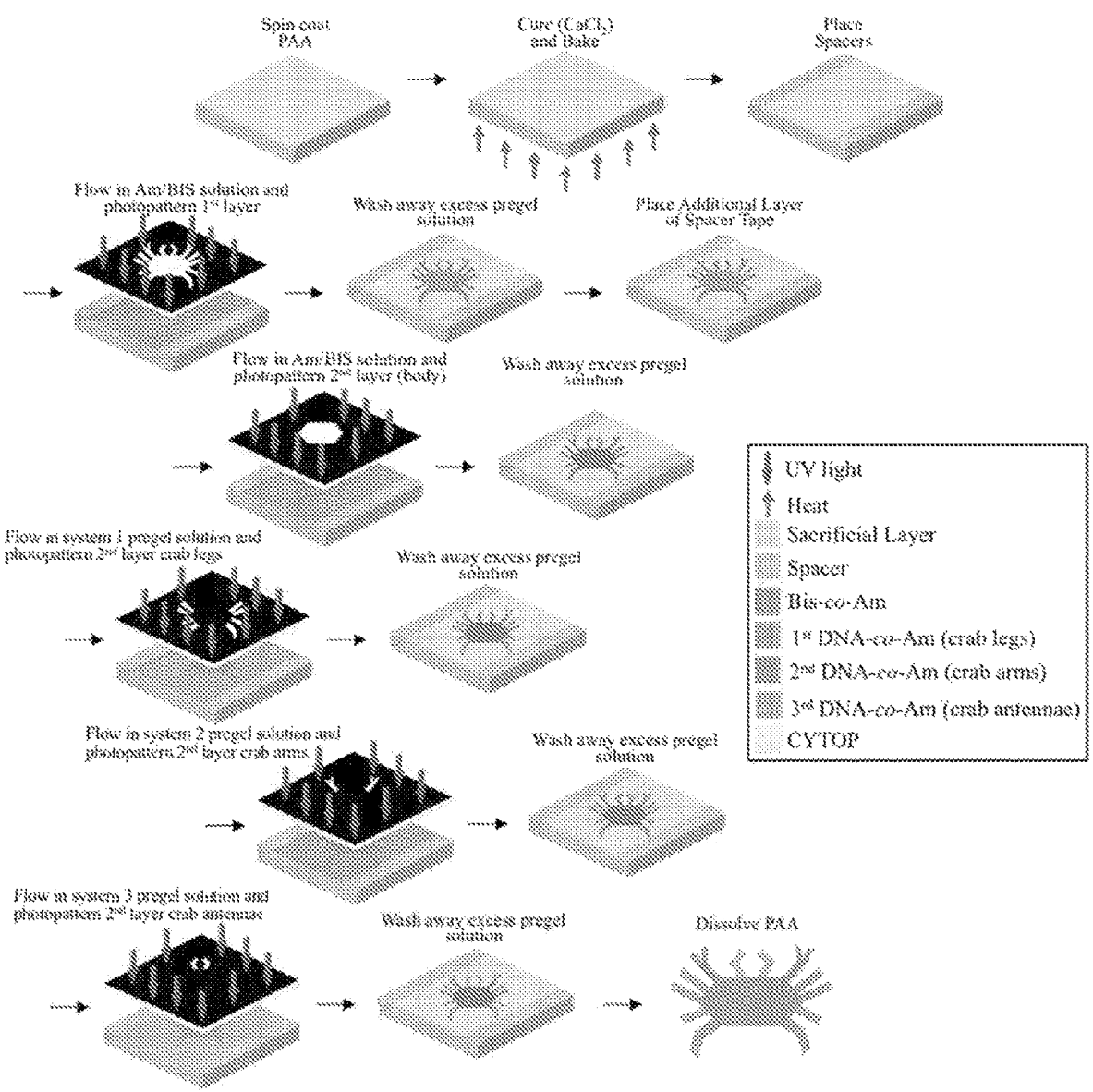

FIG. 21 Crab fabrication. Parameters such as bake temperature/time, spacer thickness and solution concentrations are listed in Methods.

Figure 22:
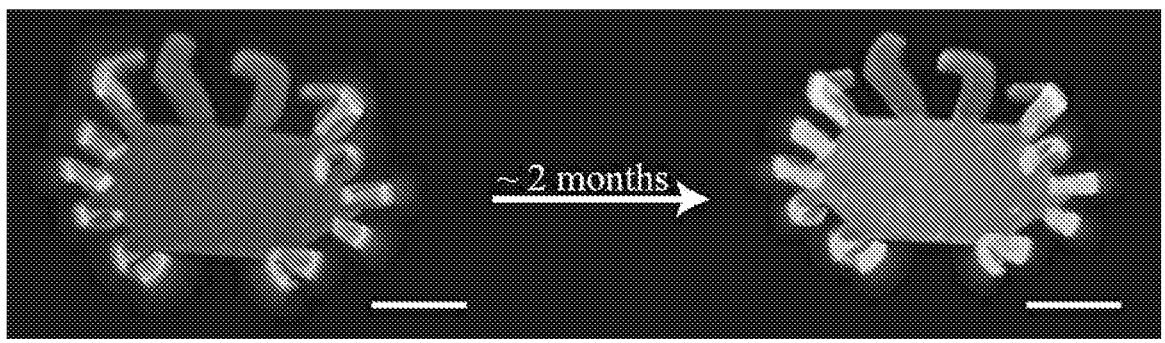

FIG. 22 BIS/DNA bilayer crab stability after actuation. Poly(Am-co-BIS)/poly(Am-co-DNA) crab architectures were prepared according to the protocol described in Methods and FIG. 21. Each DNA domain of the bilayers was actuated via treatment with a solution containing 20 µM of the systems 1-3 hairpins, with 2% terminator, for at least 24 hours at room temperature. The actuated crab bilayers then were stored in this same buffer at 4° C. for 2 months. The samples were imaged after the room temperature incubation (left) and after storage at 4° C. for two months (right) via fluorescence microscopy. Scale bars are 2 mm.

Figure 23:
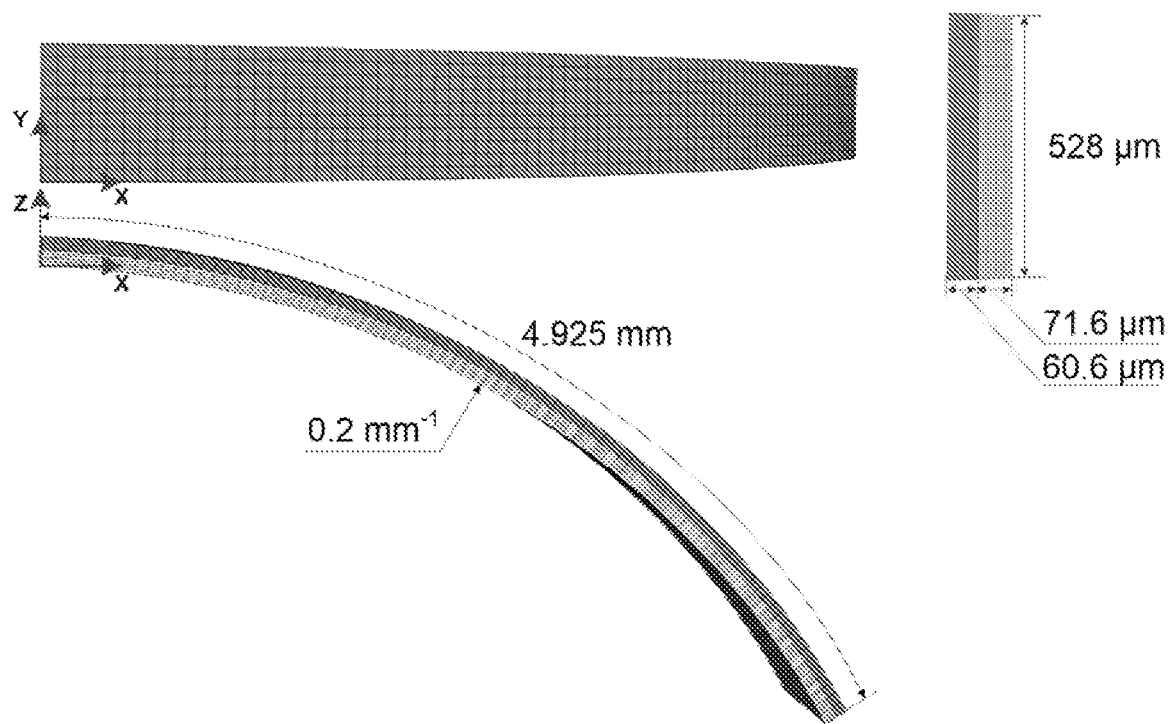
Figures 24A, 24B, 24C, 24D:
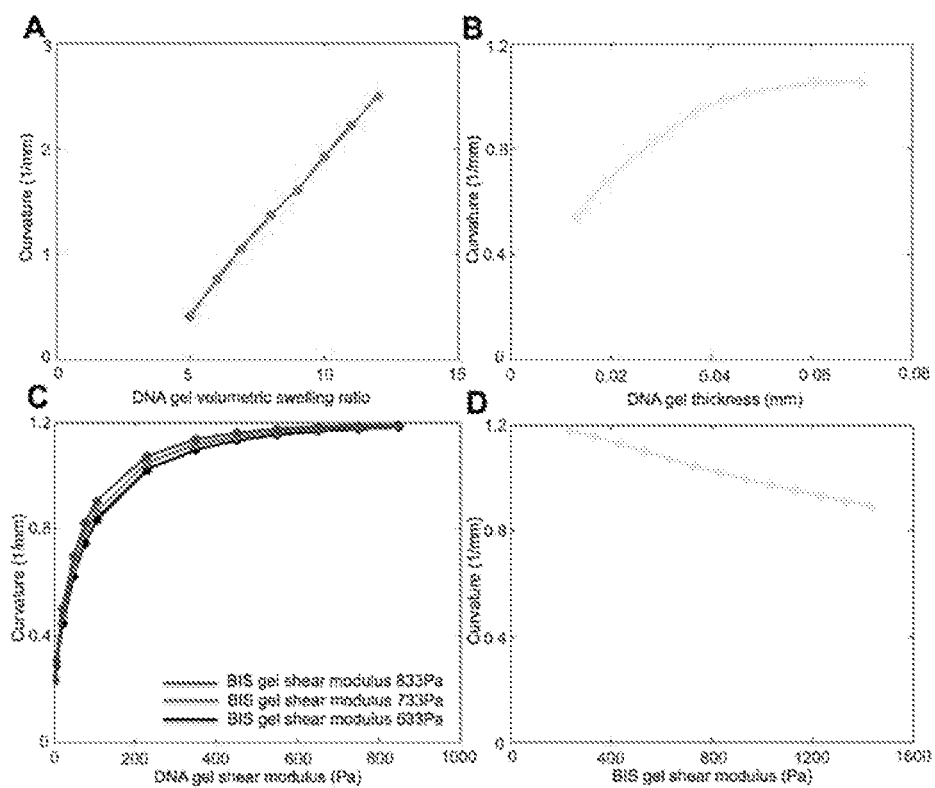

FIG. 23 Finite element model of the BIS/DNA hydrogel bilayer. Green represents poly(Am-co-BIS) hydrogel and red represents poly(Am-co-DNA) hydrogel.

FIG. 24A-24D Computational predictions of bilayer curvature as DNA gel swelling ratio, DNA gel thickness, and DNA and BIS gel shear moduli are varied one at a time. (A) DNA gel volumetric swelling ratio was changed from 5 to 12, while a DNA gel thickness of 60.6 µm, DNA gel shear modulus of 229 Pa, BIS gel thickness of 71.6 µm and BIS gel shear modulus of 733 Pa were kept constant; (B) DNA gel thickness was changed from 0.013 to 0.07 mm, while a DNA gel shear modulus of 229 Pa, DNA gel volumetric swelling ratio of 6.91, BIS gel thickness of 71.6 µm and BIS gel shear modulus of 733 Pa were kept constant; (C) DNA gel shear modulus was changed from 2.29 to 850 Pa for a BIS gel shear modulus of 633~833 Pa, while a DNA gel thickness of 60.6 µm, DNA gel volumetric swelling ratio of 6.91 and BIS gel thickness of 71.6 µm were kept constant; (D) BIS gel shear modulus was changed from 233 to 1433 Pa while a DNA gel shear modulus of 229 Pa, DNA gel thickness of 60.6 µm, DNA gel volumetric swelling ratio of 6.91 and BIS gel thickness of 71.6 µm were kept constant.

FIG. 25 Detailed Hairpin Structures. Figure discloses SEQ ID NOS 66, 67, 4, and 6, respectively, in order of appearance.

FIG. 26 Color Coded DNA Sequences. Figure discloses SEQ ID NOS 1-27, respectively, in order of appearance.

Figure 27:
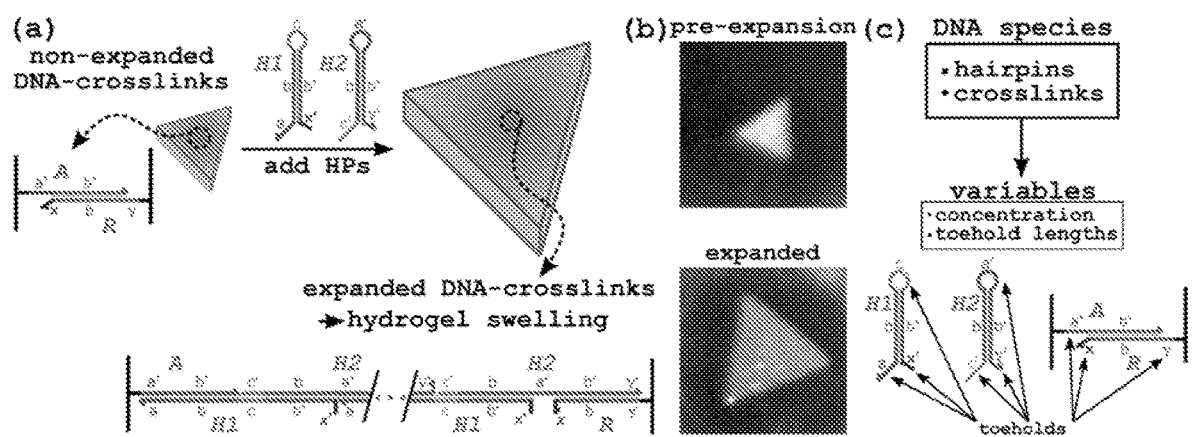

FIG. 27A-27C Triggering hydrogel expansion using DNA. (a) Hydrogels containing anchored DNA capable of initiating a hybridization chain reaction by reacting with a set of hairpins. DNA hairpins sequentially bind the growing DNA chain, significantly increasing the DNA content of the hydrogel. (b) Representative images of a poly(PEGDA-co-S1dsDNA1.154) hydrogel expanded using 20 µM per hairpin. Hydrogels are visualized using the fluorophore Rhodamine B methacrylate that is incorporated during polymerization. (c) Parameters that could control the rate and extent of DNA-induced hydrogel expansion.

Figure 28:
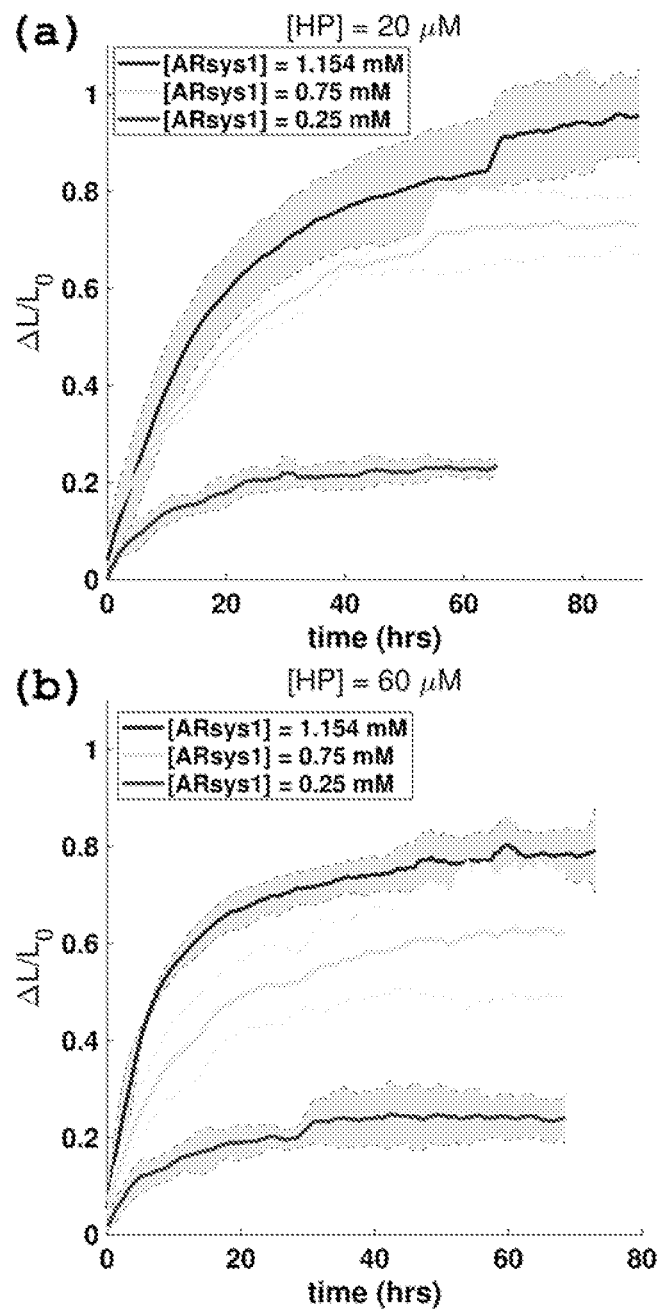

FIG. 28A-28B Controlling hydrogel expansion using crosslink concentration. Hydrogels were polymerized with DNA crosslinks at 1.154, 0.75, or 0.25 mM with System 1 sequences and were incubated with hairpins at a final concentration of (a) 20 µM or (b) 60 µM per type. Curves are the relative change in hydrogel side length after the addition of hairpins. Solid lines are the average of 3-6 hydrogels; shaded regions show 95% confidence intervals as determined by standard deviations.

Figure 29:
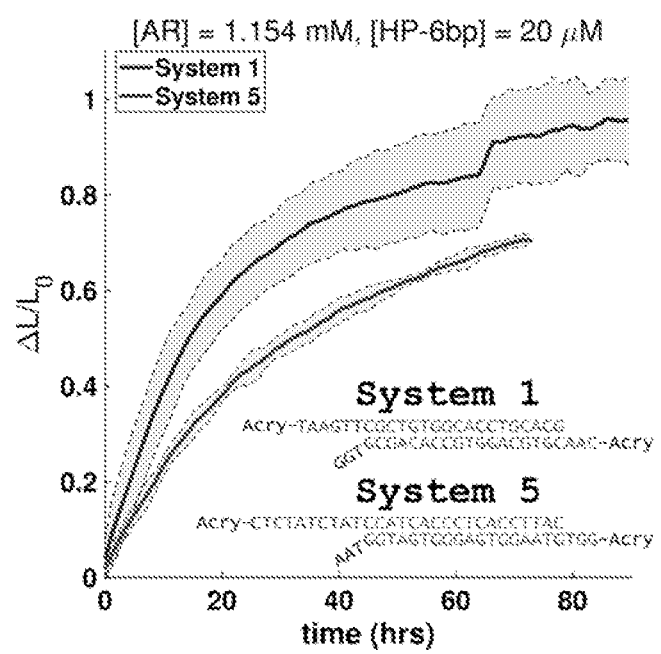

FIG. 29 Hydrogel expansion kinetics depend on crosslink sequence. The relative change in side length of hydrogels polymerized with either System 1 or System 5 crosslinks incubated with 20 µM hairpins containing their respective sequences. Hairpin toehold lengths were 6 bp/3 bp for each system. Solid lines are the average of 3 or 6 hydrogels; shaded regions show 95% confidence intervals as determined by standard deviations. Inset: sequences of System 1 and System 5 crosslinks. Domains are labeled by their respective colors. Figure discloses SEQ ID NOS 68-71, respectively, in order of appearance.

Figure 30:
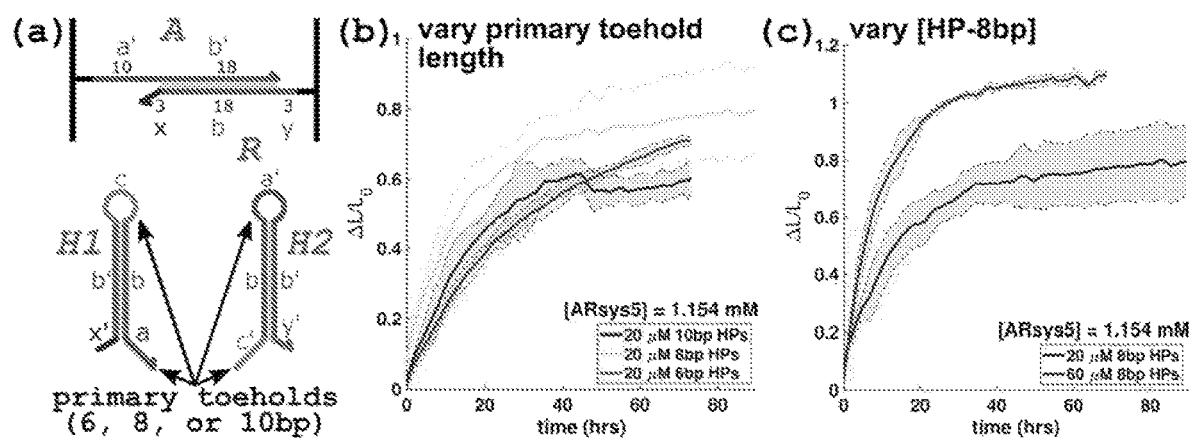

FIG. 30A-30C Effect of the length of the hairpin's primary toehold on the degree and rate of hydrogel expansion. (a) Hydrogels were polymerized with crosslinks containing 10 bp primary toeholds and 3 bp secondary toeholds. Numbers indicate the number of bases in those domains in the crosslink. Hairpins were designed to have 6, 8, or 10 bp long primary toeholds that can react with the crosslinks for hairpin insertion. (b) Relative change in hydrogel side length for hydrogels polymerized with 1.154 mM of the crosslinks in (a) incubated with 20 µM of hairpins containing 6, 8, or 10 bp long primary toeholds. (c) Relative change in hydrogel side length for hydrogels polymerized with 1.154 mM of the crosslinks in (a) incubated with 20 or 60 µM 8 bp primary toehold hairpins.

Figure 31:
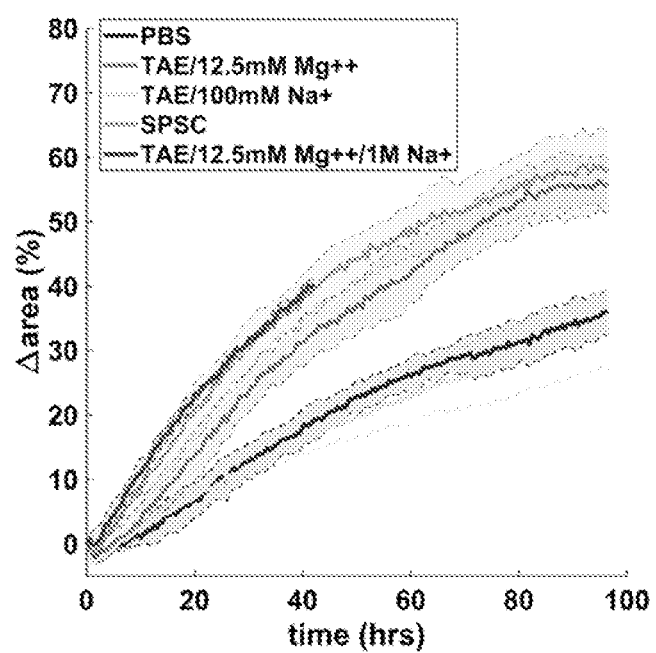

FIG. 31 Response of poly(PEGDA10k-co-S1dsDNA1.154) hydrogel particles to DNA hairpins in different salt-containing buffers. Polymerizing hairpins were individually prepared in 1×TAE/12.5 mM magnesium acetate by flash cooling at a concentration of 200 µM. Hydrogel particles were buffer exchanged into the indicated buffer in the legend and incubated with 20 µM per hairpin type. The final reaction solution contained 1× concentration of the buffer indicated plus 0.2×TAE and 0.25 mM magnesium acetate supplemented from the hairpin stock solution. In general, the dependence of the rate of hydrogel swelling due to hairpin incorporation into the crosslinks is consistent with the dependence of DNA hybridization on monovalent and divalent cation concentration. Pure 1×PBS: 137 mM NaCl, 2.7 mM KCl, 10 mM $Na_2HPO_4$, 1.8 mM $KH_2PO_4$. Pure 1×SPSC: 1 M NaCl, 50 mM $Na_2HPO_4$, pH 8.0.

Figure 32:
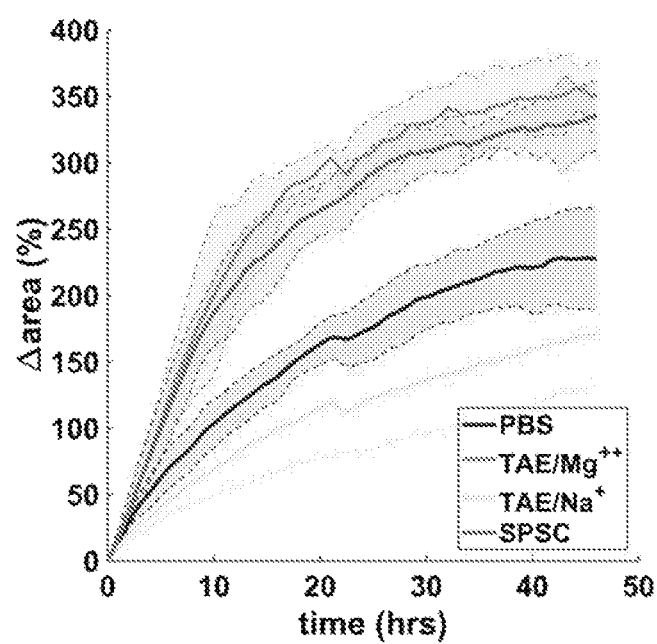

FIG. 32 Response of poly(acrylamide-co-S1dsDNA1.154) hydrogel particles to DNA hairpins in different salt-containing buffers. Hairpins, with 10% of the total hairpins being terminating hairpins, were prepared in 1×TAE/12.5 mM magnesium acetate by flash cooling at a concentration of 400 µM. Hydrogel particles were buffer exchanged into the indicated buffer in the legend and incubated with 20 µM per hairpin type. The final reaction solution contained 1× concentration of the buffer indicated plus 0.1×TAE and 0.125 mM magnesium acetate supplemented from the hairpin stock solution. In general, the dependence of the rate of hydrogel swelling due to hairpin incorporation into the crosslinks is consistent with the dependence of DNA hybridization on monovalent and divalent cation concentration. Pure 1×PBS: 137 mM NaCl, 2.7 mM KCl, 10 mM $Na_2HPO_4$, 1.8 mM $KH_2PO_4$. Pure 1×TAE/$Mg^{++}$: 1×TAE, 12.5 mM MgAcetate. Pure 1×TAE/$Na^+$: 1×TAE, 100 mM NaCl. Pure 1×SPSC: 1 M NaCl, 50 mM $Na_2HPO_4$, pH 8.0.

Figure 33:
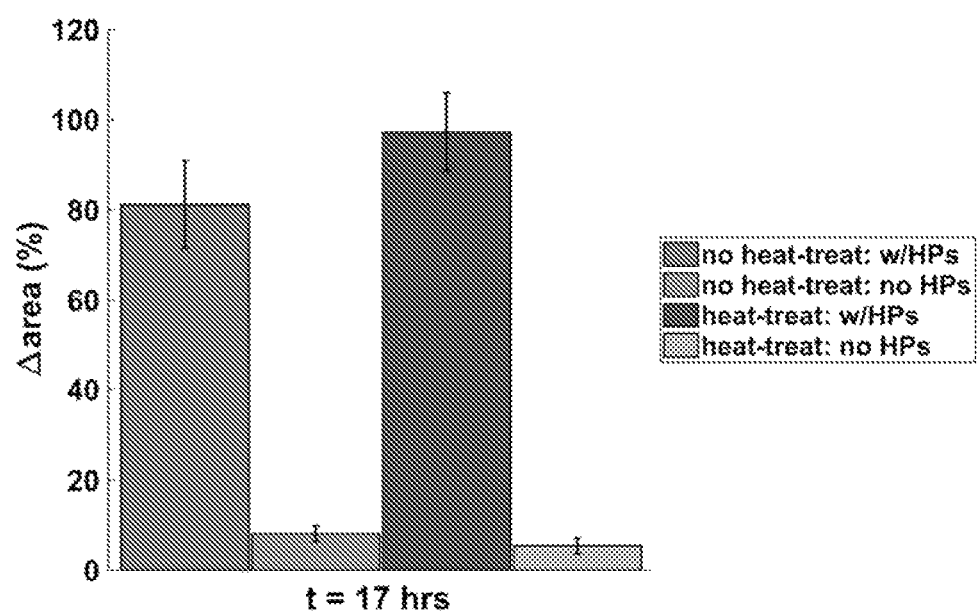

FIG. 33 Response of poly(acrylamide-co-S1dsDNA1.154) hydrogel particles to DNA hairpins (HPs) in cell medium (DMEM/10% fetal bovine serum) at 37° C. that has or has not been heat-treated. Heat-treated medium was prepared by incubating the cell medium at 65° C. for 30 minutes prior to adding hydrogel particles to the medium. DNA-crosslinked hydrogels in cell medium without heat-treatment can potentially swell in the absence of polymerizing hairpins because DNases present in the serum could break the DNA crosslinks and cause de-crosslinking of the hydrogel. After 17 hours of incubation, particles in non-heat-treated medium do not show a significant amount of swelling in the absence of hairpins and have a similar change in area to particles in heat-treated medium without hairpins. Hydrogel swelling was induced in both the heat-treated medium and medium without heat-treatment by the addition of polymerizing hairpins, 10% of which were terminating hairpins.

FIG. 34 Applications of programmable hydrogels of the present invention which is a mixture of polymer network and water (or other solvent). It can contain over 90% of water, which leads to a rubbery and transparent texture, with high biocompatibility. Hydrogels of the present invention maybe used in fields such as biotechnology, bioengineering, pharmacy, agriculture, veterinary, and food industry. Some examples are shown here.

FIG. 35 Stimuli-responsive hydrogels can change their volume significantly in response to small alterations of certain environmental parameters, such as pH, ions, oxidants (chemical stimuli) and light, temperature, ultrasound, magnetic field (physical stimuli), and biomolecular stimuli. PNIPAM as a temperature controlled polymer network is shown here as an example.

FIG. 36 DNA is an attractive stimulus for hydrogel swelling because it's programmable at the molecular level. In a previous study, DNA has been used to build polymer networks and hydrogels. We designed a DNA-hydrogel system that is built using a polymer and DNA, and is able to respond to DNA signals.

FIG. 37 The DNA responsive hydrogel system.

Figure 38:
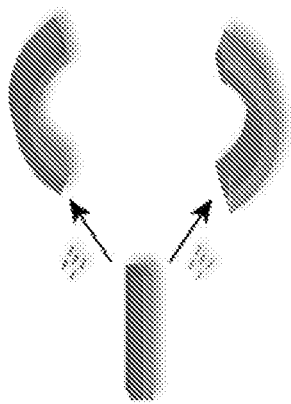

FIG. 38 An example of a DNA hydrogel robot.

Figure 39:
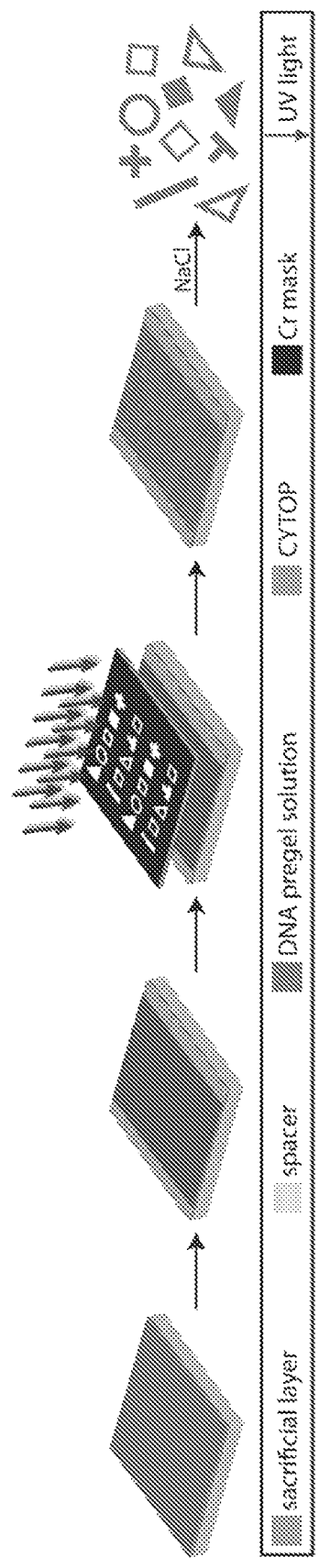

FIG. 39 Fabrication process of single layer hydrogels.

Figure 40:
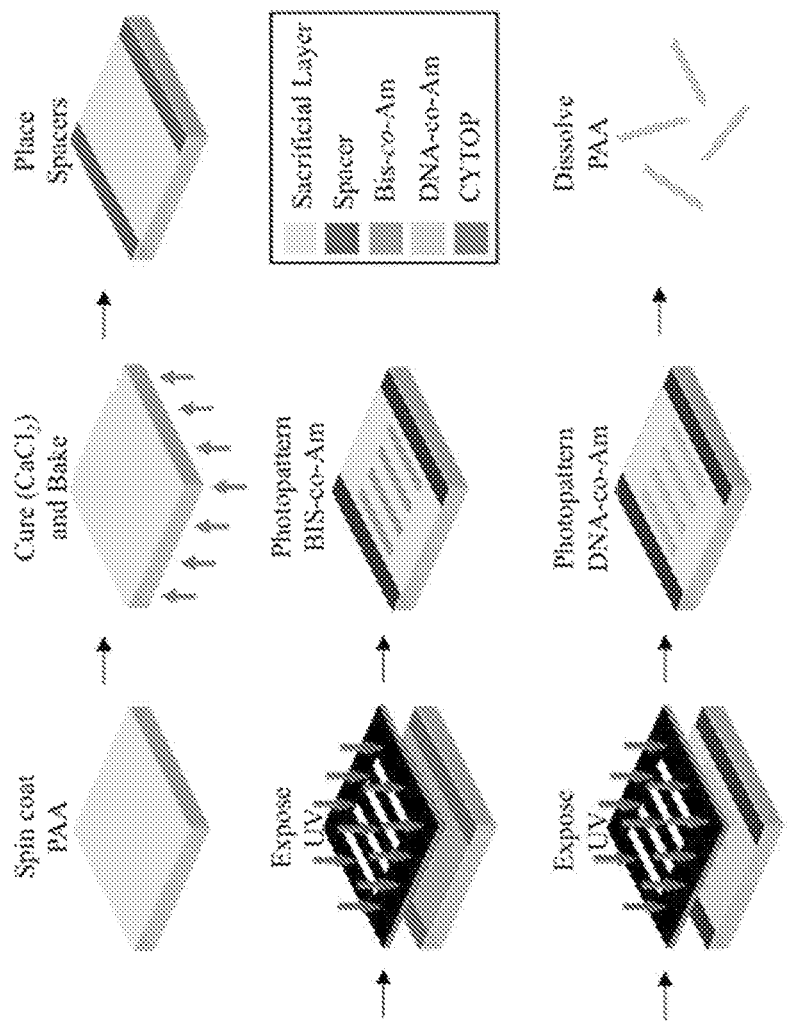

FIG. 40 Fabrication process of bilayer hydrogels.

Figure 41:
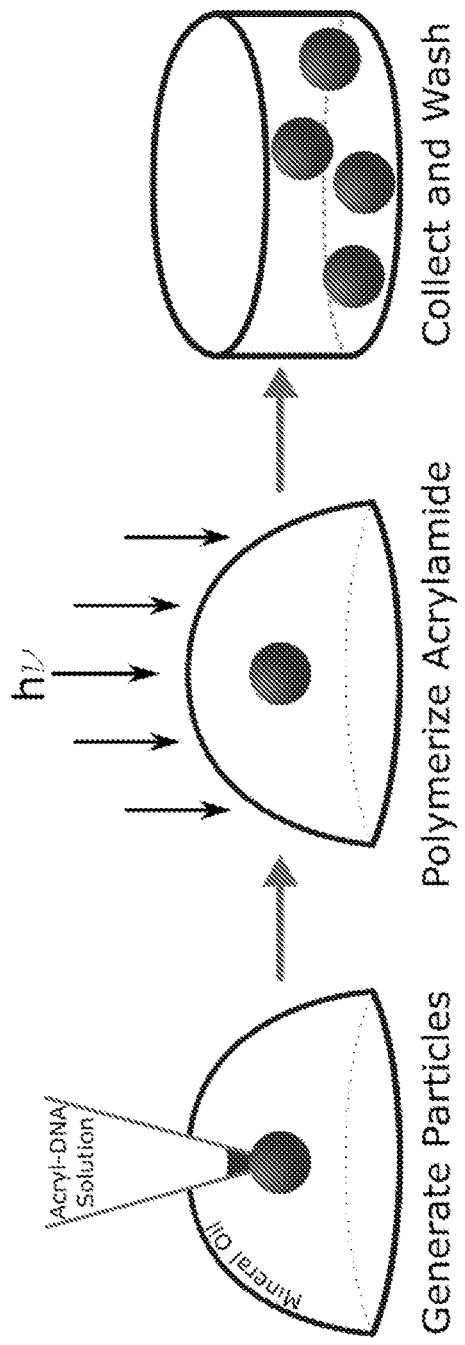

FIG. 41 Fabrication process of gel microparticles.

Figure 42:
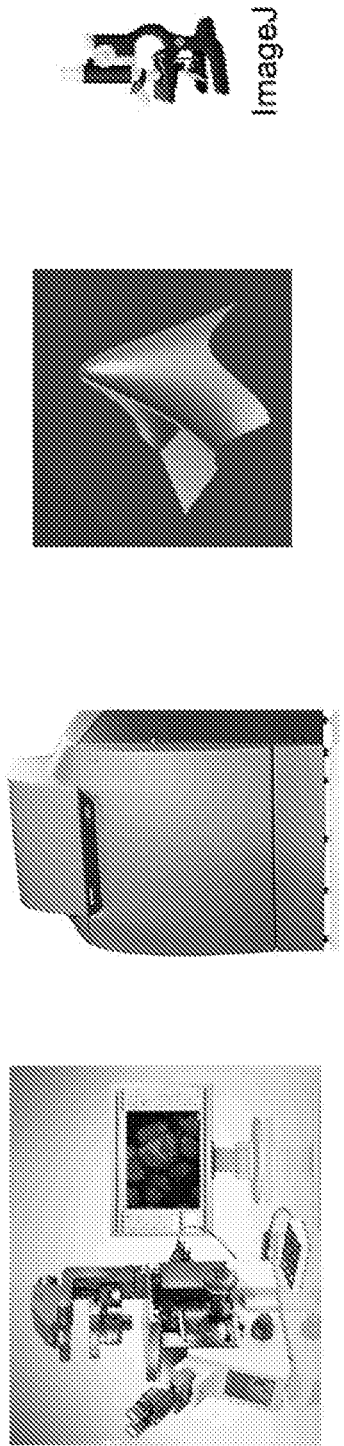

FIG. 42 Swelling experiments and methods.

Figure 43:

FIG. 43 Examples of programmable gels of the present invention including Am-(BIS)-DNA, PEGDA-DNA, GELMA-DNA and Am-Alginate-DNA.

FIG. 44 Swelling result for Am-DNA.

Figure 45:
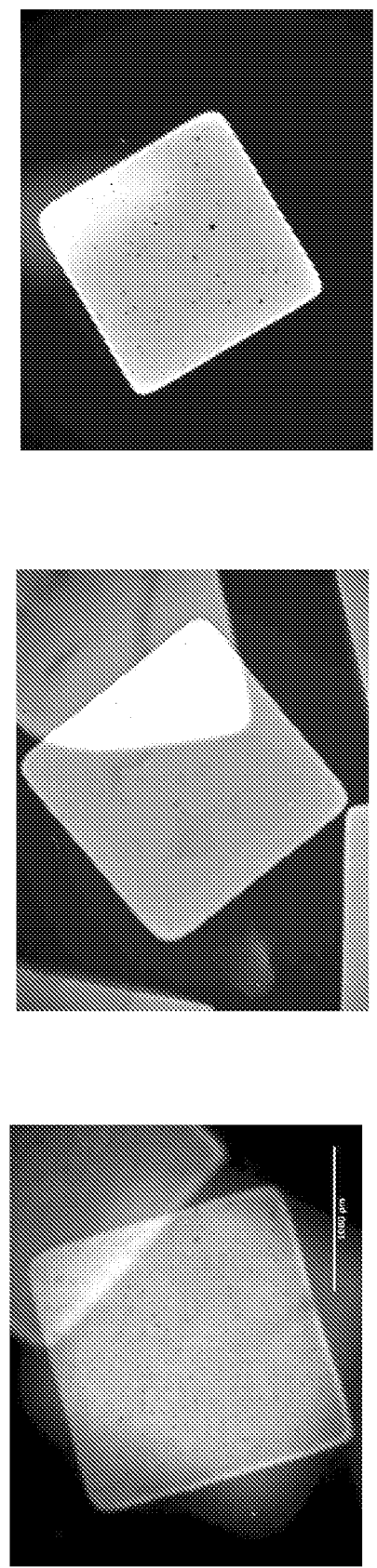

FIG. 45 Results showing validation of the concept to add BIS content in the Am-DNA gel to make the Am-BIS-DNA gels. The higher BIS concentration makes the gel water hydration capacity smaller.

FIG. 46 Swelling curves of Am-DNA gels and comparison to Am-BIS-DNA gels.

FIG. 47 Concept of PEGDA-DNA gels. PEGDA, as poly(ethylene glycol) diacrylate, is more biocompatible that acrylamide gels and has been widely used for biomedical applications. It's a self-crosslinking polymer, which means it does not need additional crosslinkers (BIS or DNA to Am) to form a polymer network. PEGDA has a wide range of molecular weight (controllable chain length), leading to a huge difference in solvent hydration and material modulus, which provides a wide range of tunable material properties.

FIG. 48 Examples of a variety of shapes of programmable PEGDA gels made with 575 or 10 k molecular weight.

FIG. 49 Due to the low ratio of DNA crosslinks to PEGDA the programmable PEGDA575-DNA gel does not swell over 72 h.

Figure 50:
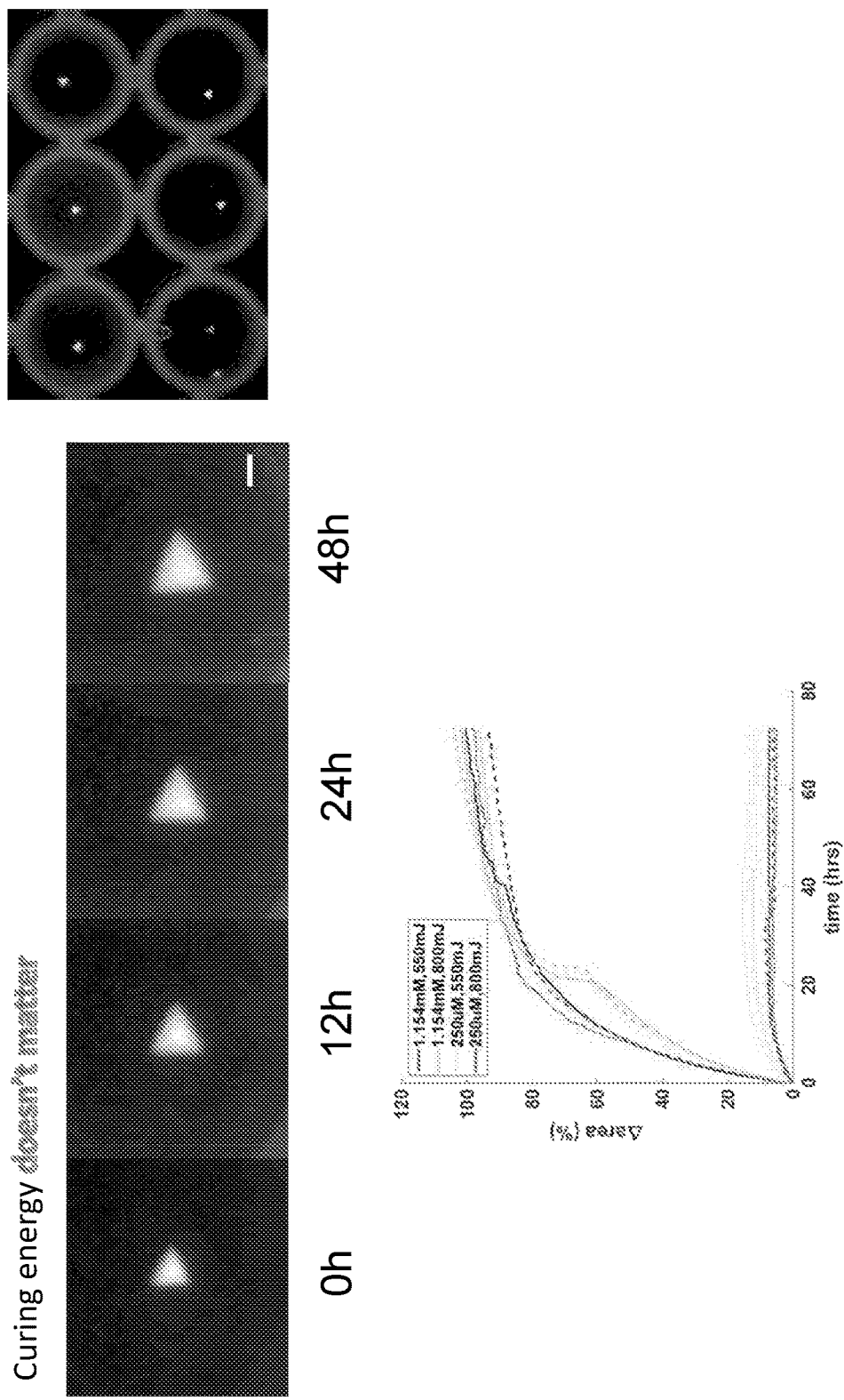

FIG. 50 Images showing swelling of programmable PEGDA 10 k-DNA gels. The higher the DNA crosslink in the gel, the more swelling we can get. Another finding is that the degree of swelling is relatively unchanged with changes in the curing energy for the gels.

FIG. 51 Images showing a heat reversible a programmable PEGDA-DNA gel. As a self-crosslinking gel, the extended DNA crosslink may be broken by heat (which dissociates the hairpins) without breaking the gel. The PEGDA-DNA gel can stay intact after heating to 95° C. and regrows in the original DNA hairpin solution.

Figure 52:
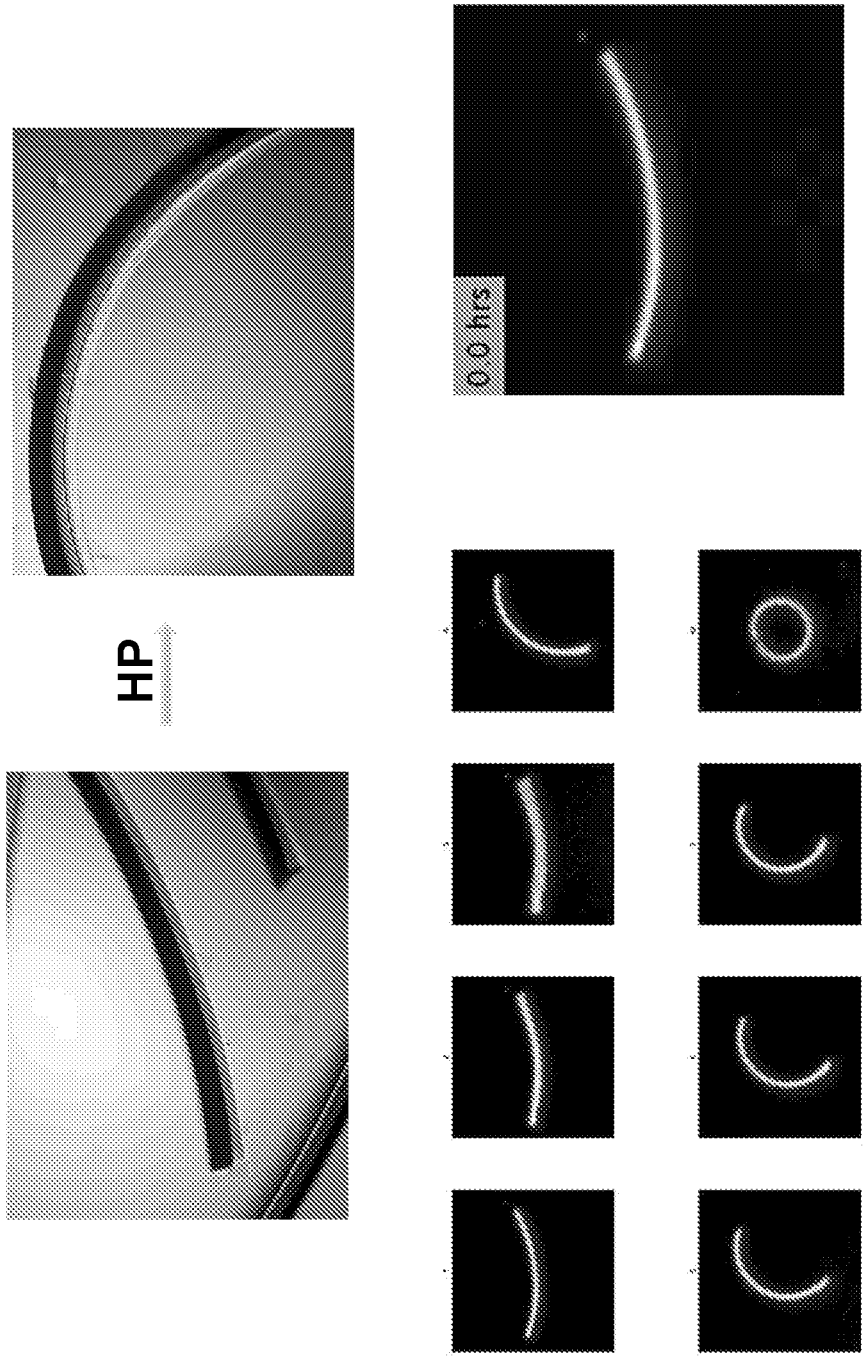

FIG. 52 Images showing the fabrication and operation of a programmable PEGDA gel bilayer with one layer with DNA-crosslinked gel and the other layer composed of pure PEGDA. By swelling the DNA gel side using a nucleic acid signal such as DNA hairpins, the bilayer gel curls.

Figure 53:
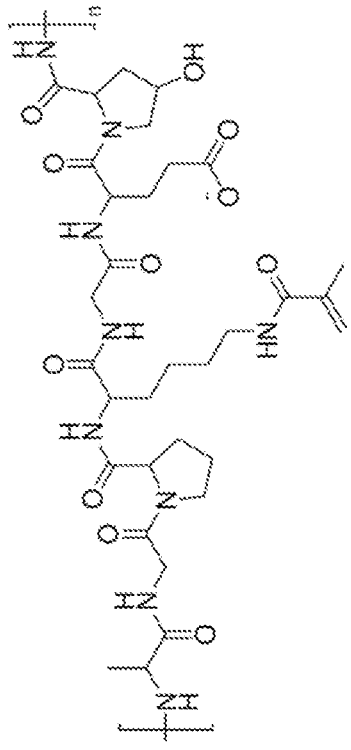

FIG. 53 Demonstration of a GelMA gel. GelMA, as gelatin methacrylate, is perfect for cell culture. It could also be cured by UV by adding photoinitiator, as the Am or PEGDA gels. It's a self-crosslinking polymer, and by varying the molecular weight, the inventors could get different 'bloom' (different modulus) of GelMA gel.

FIG. 54 Images showing fabrication of programmable GelMA-DNA gels.

Figure 55:
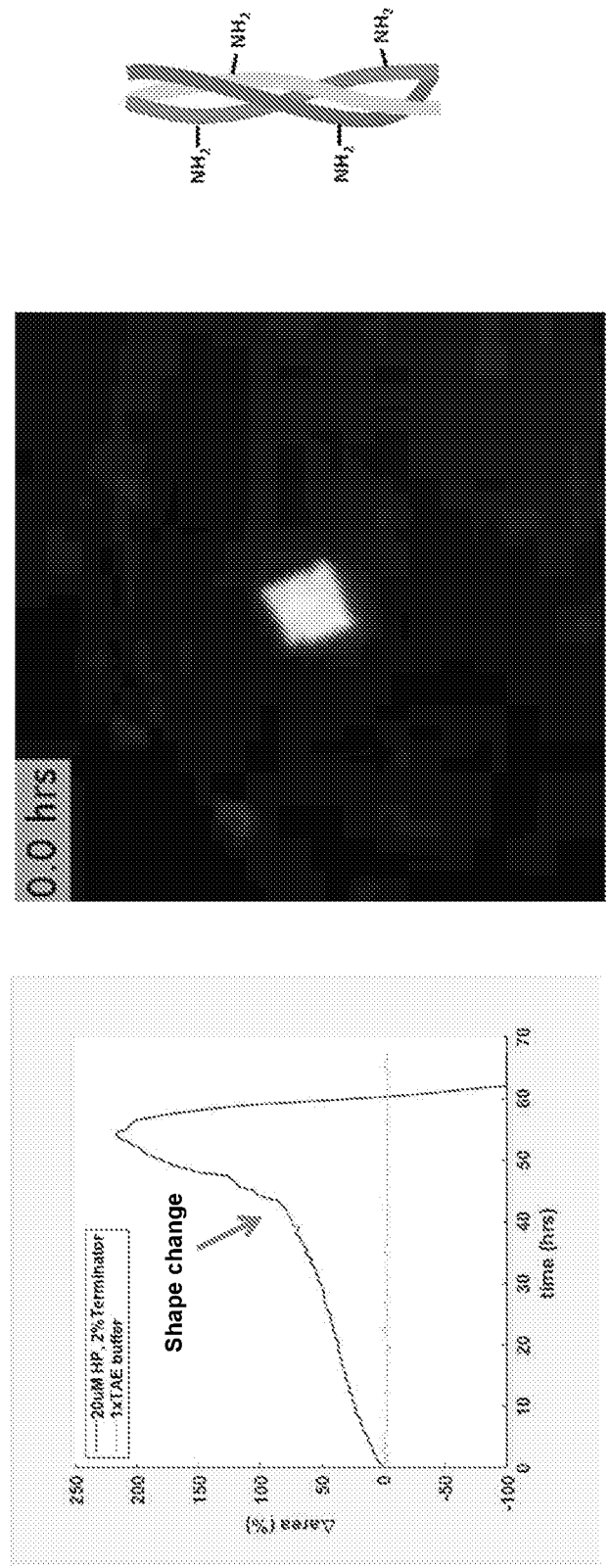

FIG. 55 Images showing swelling of a programmable GelMA-DNA gel. During swelling, the GelMA gel has a sudden shape change around ~40 hrs.

Figure 56:
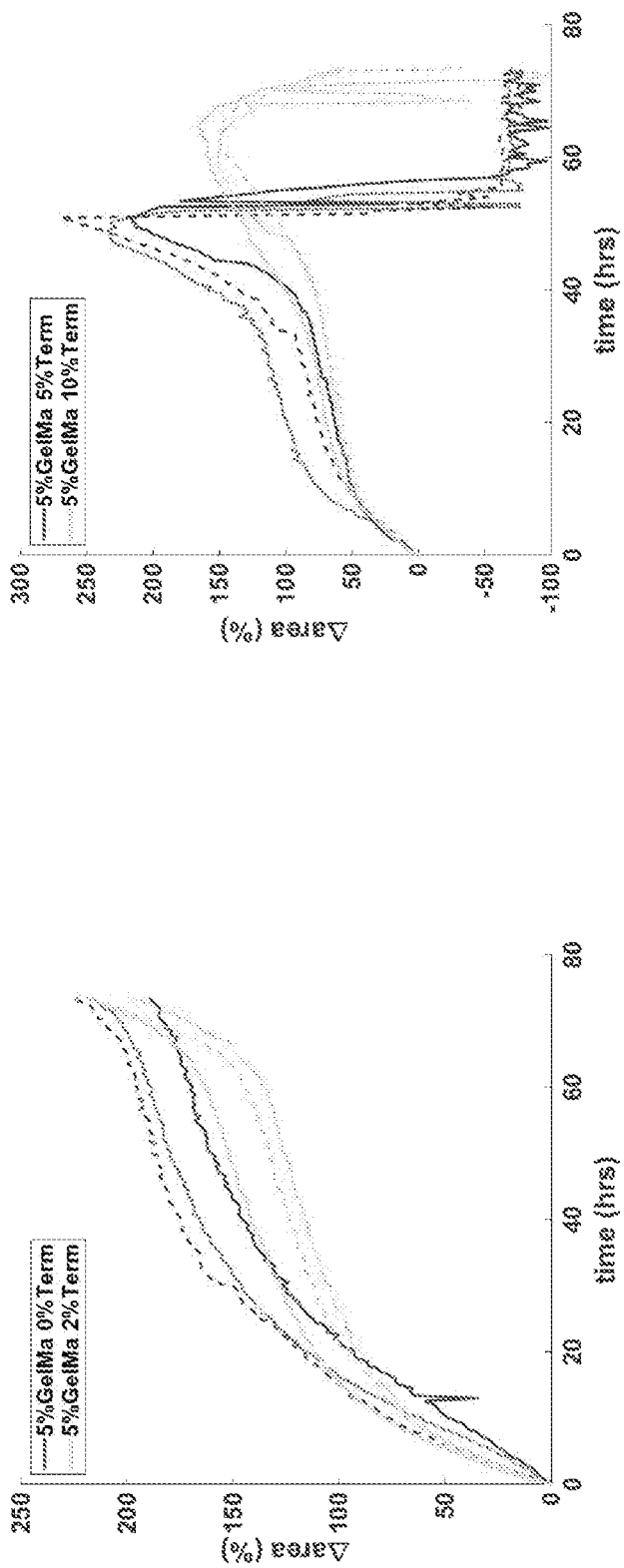

FIG. 56 The degree of swelling of programmable GelMA gels is changed by altering the terminator HPs concentration. However, the swelling speedup and disappearance of the programmable GelMA is consistent in all kinds of terminator concentrations. Another finding is that the time point of the swelling speedup depends on fabrication process, and may vary from batch to batch (40~60 hrs before swelling speedup).

Figure 57:
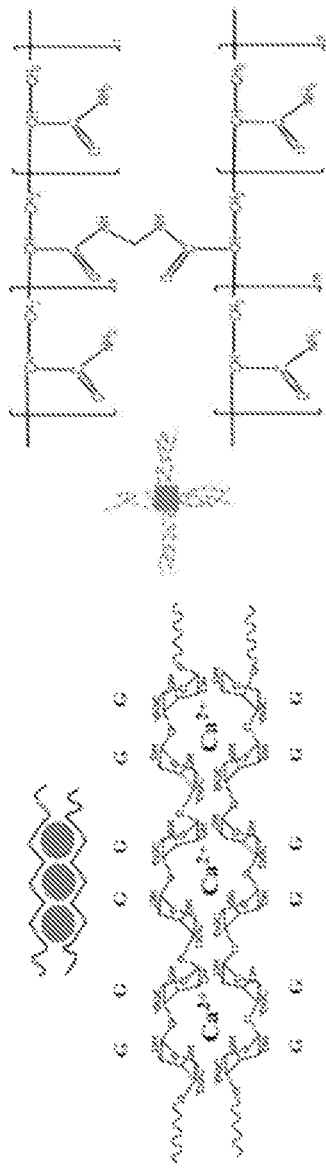

FIG. 57 Am-BIS(DNA)-Alginate gels has a double network that consist of Am-BIS(DNA) that crosslinked by covalent bonds, and Ca-Alginate which is ionic crosslinked. By heating the two polymer network mixture, a new covalent bond —CO—NH— would form between Am (—NH2) and Alginate (—COO—), which makes this gel highly stretchable.

FIG. 58 Programmable Am-DNA-alginate gels. Images showing the fabrication process used to photopattern programmable Am-DNA with Na-alginate first. After photopatterning and gel release, the gel is soaked in Ca++/Mg++ buffer to form the Ca-Alginate. Gels are heated to form —CO—NH—. When heated to 50° C. for 1 hr, the gel started to disappear after ~4 hrs during HP swelling.

FIG. 59 Am-DNA-alginate gels. As in FIG. 58 but heating condition from 50° C. 1 hr to 37° C. 12 hrs. The gels became larger after heating, and more porous.

FIG. 60 Am-Alginate DNA gel swelling. The gels heated in 37° C. for 12 hrs are more stable during swelling than the 50° C. 1 hr ones.

FIG. 61 Swelling curves of Am-Alginate DNA gel and comparison to original Am-DNA gel.

FIG. 62 Am-DNA-Alginate is not stable when preserving in water/buffer. After one week material separation from gel was observed. The Am-DNA gel is labeled with Rhodamine B and it was observed in the Cy3 channel of the microscope. The diffused material was observed in the bright field.

FIG. 63A-63E Expanding hydrogels with anchored single-stranded HCR initiators. (a) Single-stranded DNA that is capable of initiating the hybridization chain reaction is anchored to hydrogels during hydrogel polymerization. Expansion is initiated by the addition of polymerizing hairpins. (b) Relative change in side length of hydrogels with varying concentrations of anchored ssDNA initiators. Hydrogels were incubated with 20 µM of 8 bp long primary toehold hairpins. (c) Relative change in side length of hydrogels with varying concentrations of anchored ssDNA initiators incubated with 20 µM of 10 bp long primary toehold hairpins. (d) Relative change in side length of hydrogels with 1.154 mM anchored ssDNA initiator incubated with 20 or 60 µM 8 bp primary toehold hairpins. (e) Relative change in side length of hydrogels with 1.154 mM anchored ssDNA initiator incubated with 20 µM hairpins with 6, 8, or 10 bp long primary toeholds.

Figure 64:
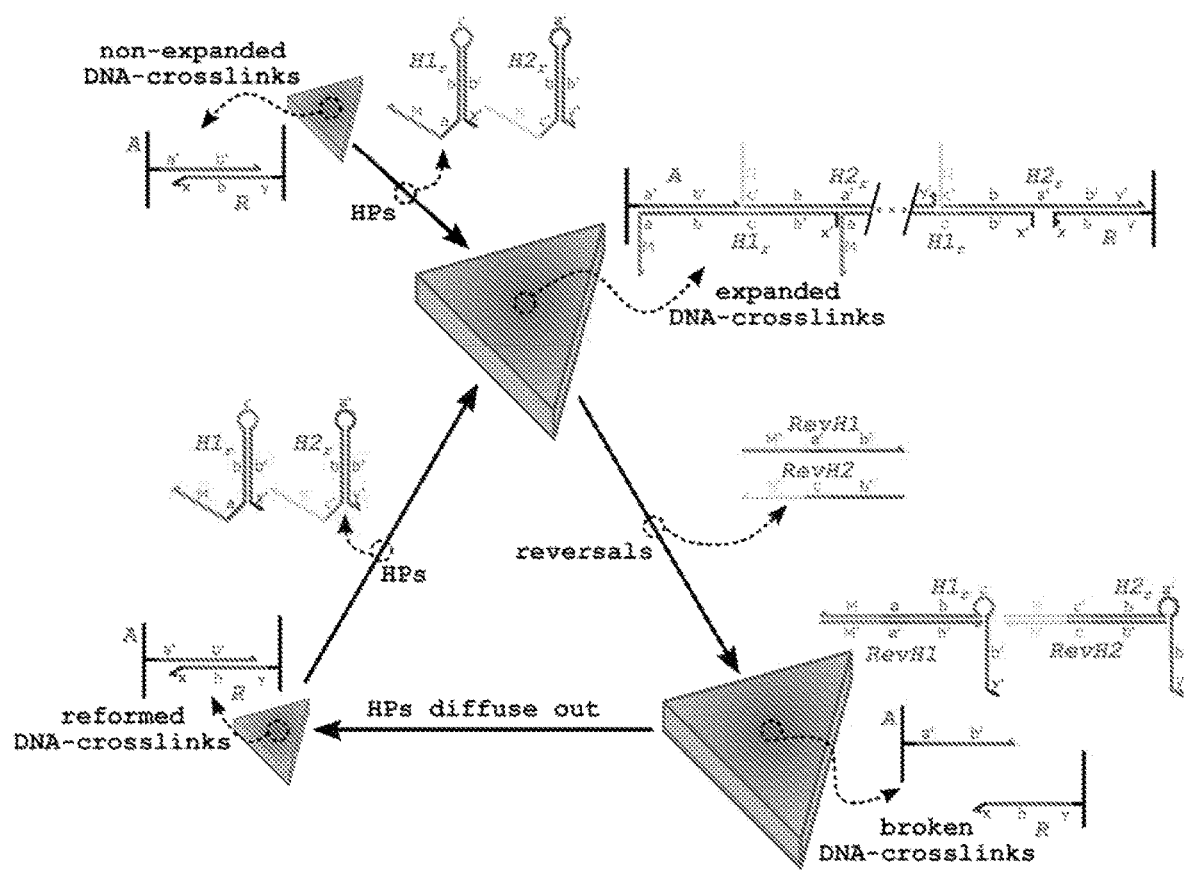

FIG. 64 Swelling and contraction of a hydrogel containing DNA crosslinks. DNA crosslinks are expanded by polymerizing hairpins (H1$_r$, H2$_r$), inducing hydrogel swelling. The addition of reversal strands RevH1 and RevH2 disrupts the polymerized hairpin chain and breaks the chain and DNA crosslink. Hairpins then diffuse out of the gel, causing hydrogel contraction and the re-hybridization of the DNA crosslinks. The addition of fresh hairpins re-initializes the expansion of the DNA crosslinks and hydrogel expansion.

Figure 65:
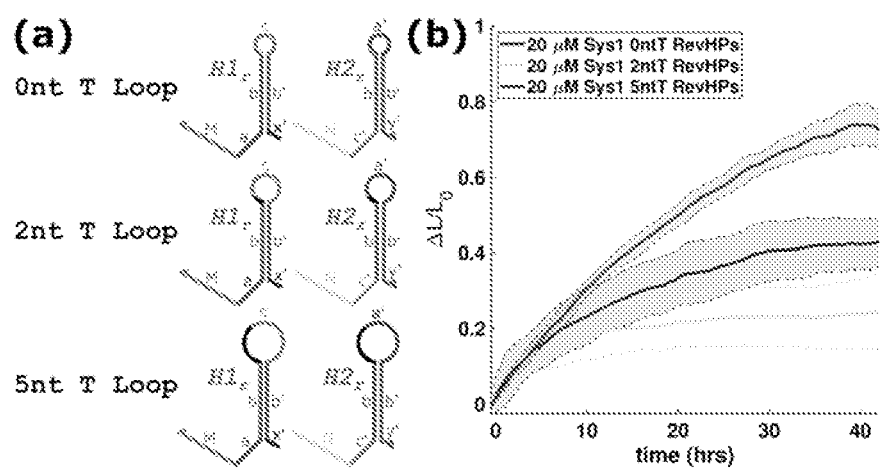

FIG. 65A-65B Design of reversible polymerization hairpins. (a) Hairpins with Reversal binding tags (M and N domains) were designed to have 0, 2, or 5 extra bases inserted into the loop of the hairpin (black domain). For System 1 and System 5 sequences, these bases are thymines. For System 2, the bases were chosen from all 4 DNA bases. (b) Uniaxial swelling of poly(PEGDA10k-co-Sys1DNA) hydrogel triangles incubated with reversible hairpins containing 0, 2, or 5 extra bases in the hairpin loop domain. Solid lines are the average uniaxial swelling curves of 2-4 hydrogels; shaded regions show the 95% confidence intervals as determined by standard deviations.

Figure 66:
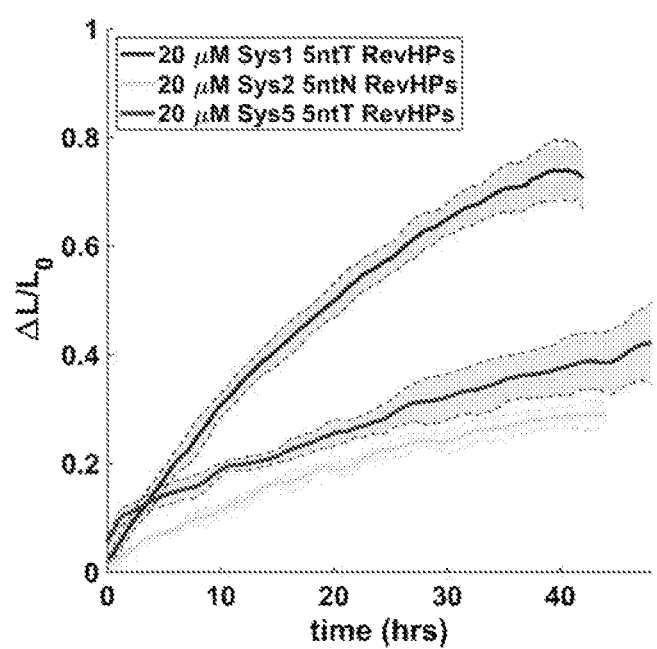

FIG. 66 Comparison of the uniaxial swelling of PEGDA10k triangles polymerized with 1.154 mM System 1, 2, or 5 DNA crosslinks and incubated with their respective reversible hairpins (5 nt loops). Concentration listed is on a per hairpin basis. Solid lines are the average uniaxial swelling curves of 2-4 hydrogels; shaded regions show the 95% confidence intervals as determined by standard deviations.

Figure 67:
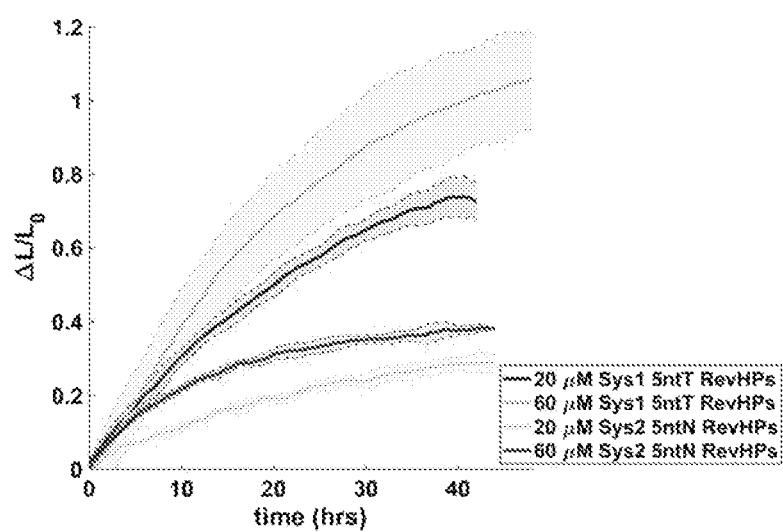

FIG. 67 Comparison of the uniaxial swelling of PEGDA10k triangles polymerized with 1.154 mM System 1 or 2 DNA crosslinks and incubated with 20 or 60 µM per 5 nt reversible hairpin. Concentration listed is on a per hairpin basis. Solid lines are the average uniaxial swelling curves of 2-4 hydrogels; shaded regions show the 95% confidence intervals as determined by standard deviations.

Figure 68:
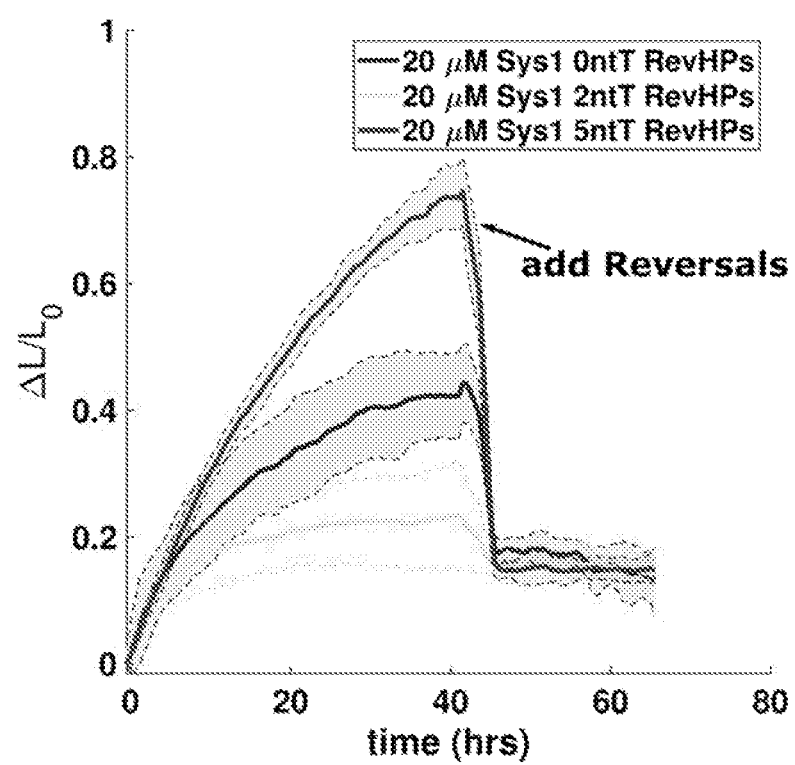

FIG. 68 Reversible swelling of poly(PEGDA10k-co-Sys1DNA) hydrogel triangles. Hydrogels were incubated with 20 µM hairpins with either 0, 2, or 5 bases added to the hairpin loop domain. After 45 hours of incubation, the hydrogels were washed 3 times and 20 µM Reversal strands were added to induce hydrogel contraction. Solid lines are the average uniaxial swelling curves of 2-4 hydrogels; shaded regions show the 95% confidence intervals as determined by standard deviations.

Figure 69:
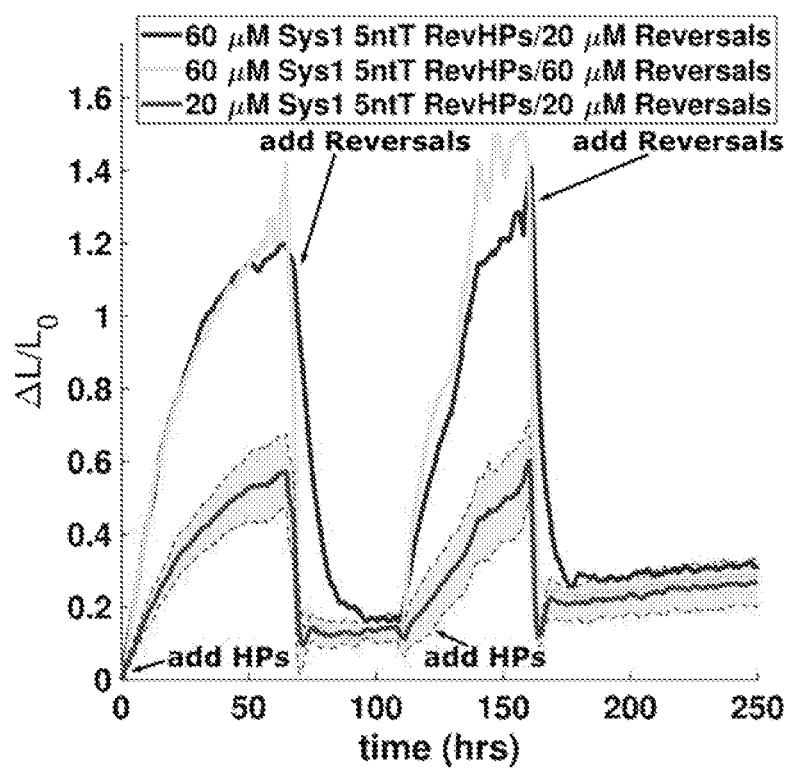

FIG. 69 Two cycles of swelling and contraction of poly (PEGDA10k-co-Sys1DNA) hydrogel triangles. Hydrogels were incubated with 20 or 60 µM System 1 5 ntT reversible hairpins. After 65 hours of incubation, the hydrogels were washed 3 times and 20 or 60 µM Reversal strands were added to induce hydrogel contraction. After 50 hours of incubation with Reversal strands, the hydrogels were washed again and a second cycle of swelling-contraction was conducted using the same hairpin and Reversal strand concentrations. Solid lines are the uniaxial swelling curves of 1 hydrogel or the average of 4 hydrogels (20 µM HPs/20 µM Reversals); shaded regions show the 95% confidence intervals as determined by standard deviations.

Figure 70:
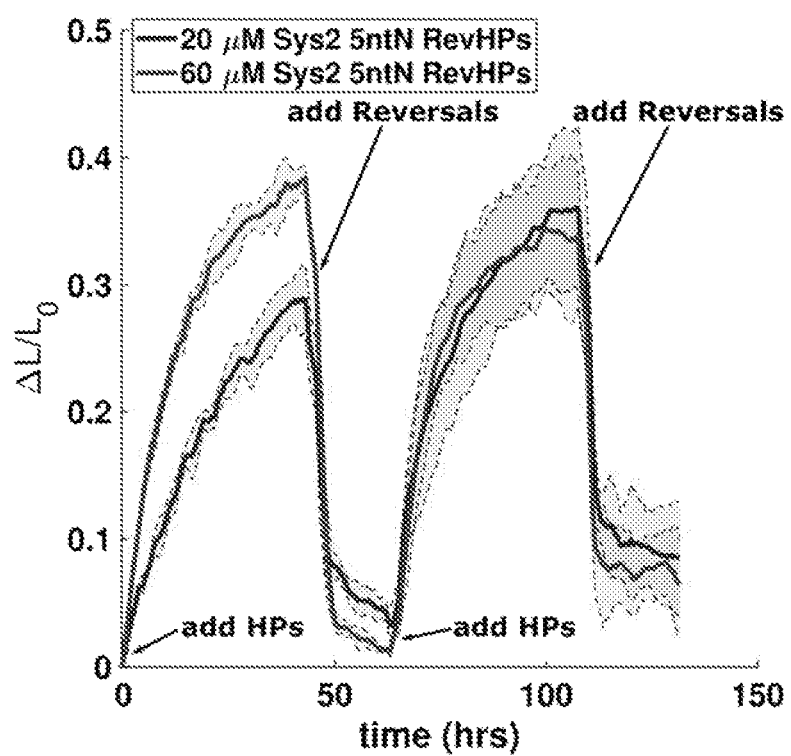

FIG. 70 Two cycles of swelling and contraction of poly (PEGDA10k-co-Sys2DNA) hydrogel triangles. Hydrogels were incubated with 20 or 60 µM System 2 5 ntN reversible hairpins. After 45 hours of incubation, the hydrogels were washed 3 times and 20 or 60 µM Reversal strands were added to induce hydrogel contraction. After 15 hours of incubation with Reversal strands, the hydrogels were washed again and a second cycle of swelling-contraction was conducted using the same hairpin and Reversal strand concentrations. Solid lines are the average uniaxial swelling curves of 2 hydrogels; shaded regions show the 95% confidence intervals as determined by standard deviations.

Figure 71:
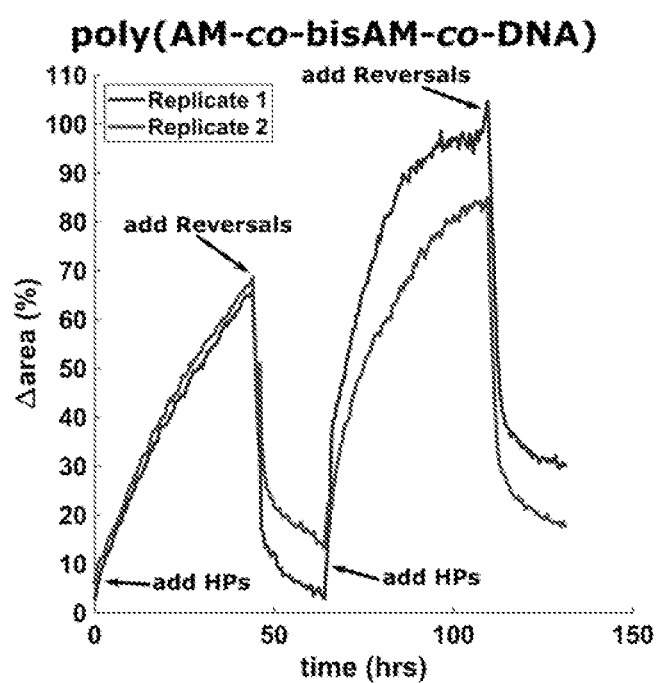

FIG. 71 Reversible swelling of a polyacrylamide hydrogel triangles crosslinked with 5 mM bis-acrylamide and 1.154 mM System 2 DNA crosslinks. Hydrogels were incubated with 60 µM System 2 5 Nspc reversible hairpins and de-swelled using 60 μM System 2 reversal strands. Lines show two replicate hydrogels. Hydrogels were washed 3× prior to new additions with 1×TAE/12.5 mM magnesium acetate/0.001% v/v Tween20 to remove excess hairpins or Reversal strands.

Figure 72:
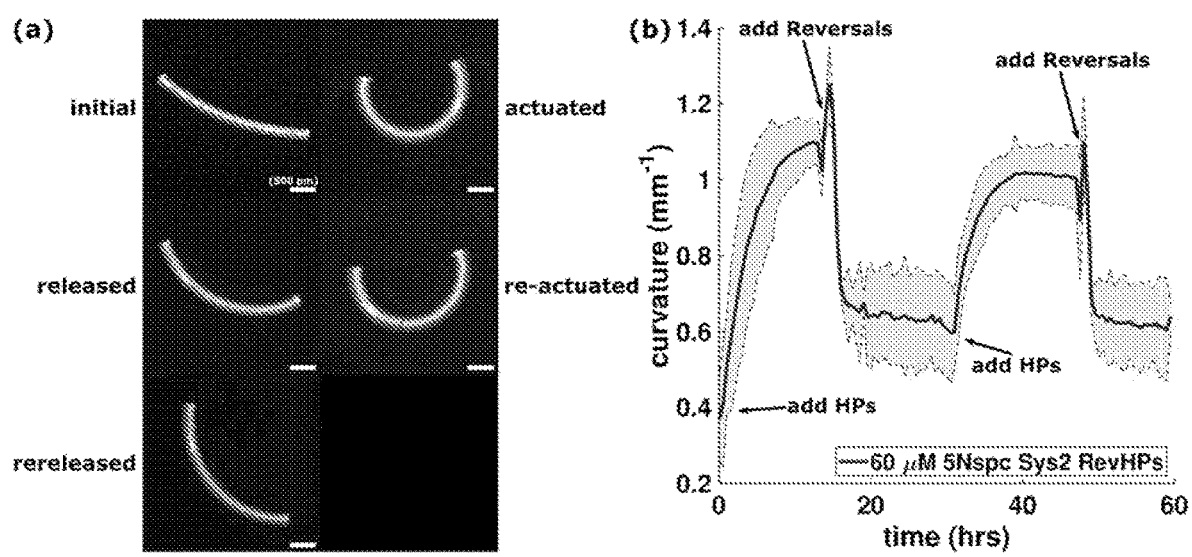

FIG. 72A-72B Examples of reversible swelling of a programmable gel.

DETAILED DESCRIPTION OF THE INVENTION

The inventor's developed wire-free responsive materials by building a library of biomolecules to achieve addressable control, such that each of a combinatorial variety of biomolecular species would direct the swelling of a specific material domain. This is analogous to the way biomolecular stimuli would enable complex sensing, signal processing and feedback within biological cells and tissues.

If one region of a material shrinks or swells in response to a chemical or physical stimulus, the material can change shape to minimize its overall free energy. The ability to addressably deform different material regions can thus allow a material to take on many shapes. This principle has been used to create metamorphic materials or soft robots in which embedded wires direct local mechanical deformations. However, wires add bulk and require batteries or tethering. Chemomechanically responsive materials, in contrast, swell or shrink in response to chemical rather than electrical or pneumatic signals. Chemicals can diffuse over large distances and into small or tortuous spaces, and the huge number of chemicals that can be synthesized offers unprecedented tunability and specificity. Chemomechanical devices require no batteries and can easily be miniaturized and integrated with other devices.

Stimuli such as temperature, light, electromagnetic stimuli or pH have been used to direct shape change. These nonspecific stimuli can induce chemical or conformational changes throughout a material, leading to dramatic swelling or shrinking. However, this lack of specificity also means these stimuli cannot produce addressable control comparable to that in wired systems. The inventors asked whether they could build a combinatorial library of biomolecules, such as DNA sequences, where each species would direct the swelling of a specific material domain.

Figures 1A, 1B, 1C:
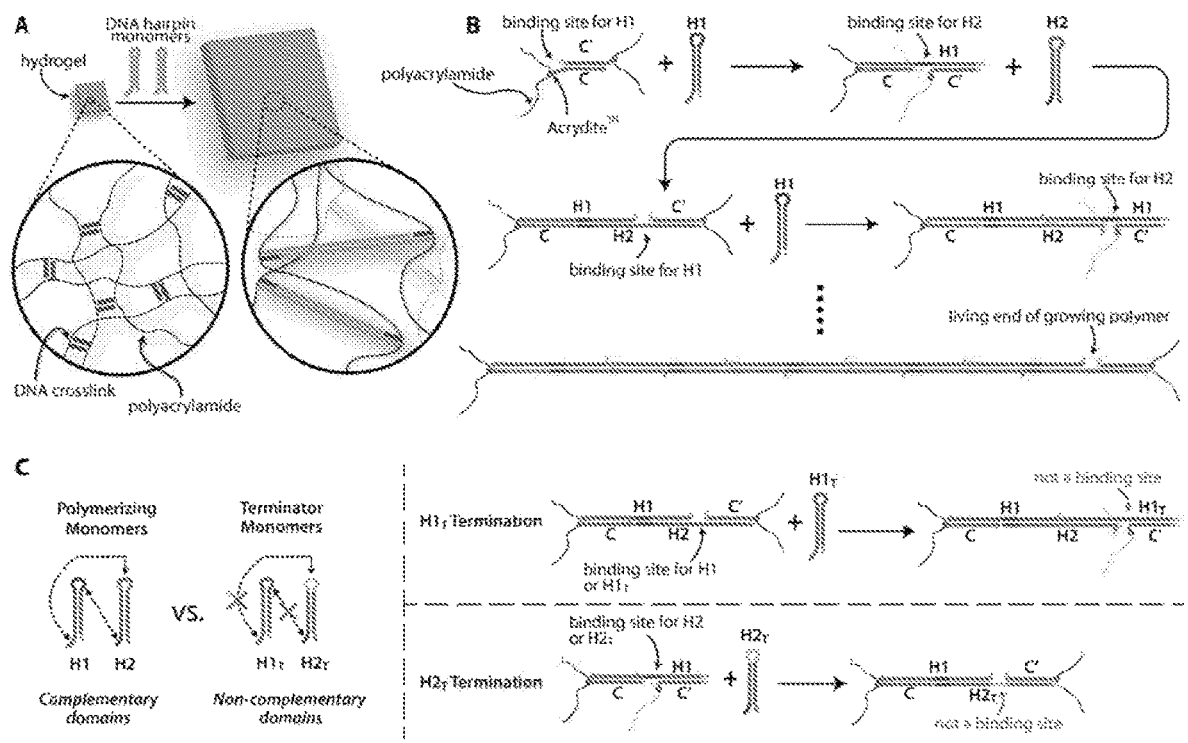
Figures 6A, 6B:
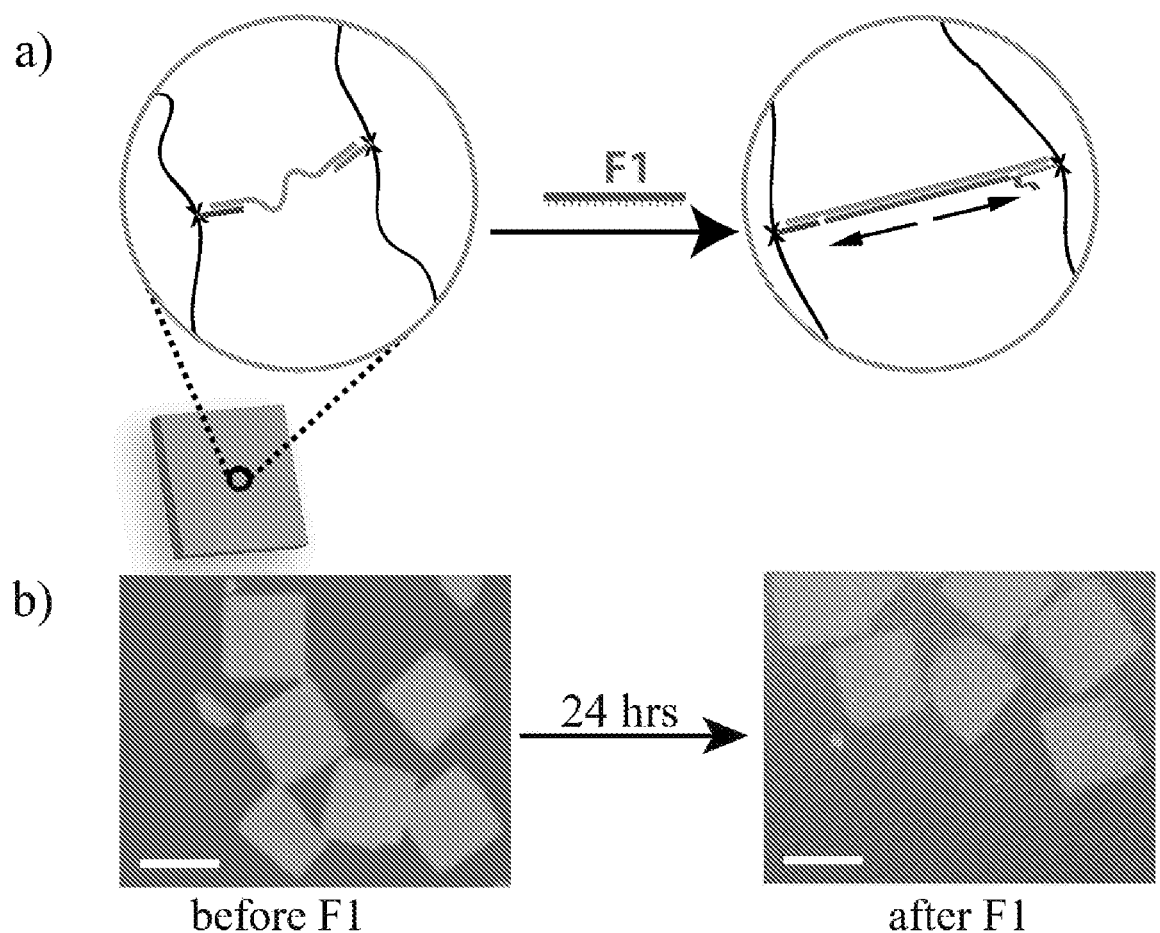
FIG. 6A-6B Hydrogel expansion driven by a single- to double-stranded crosslink transition. (A) To quantify the amount of hydrogel expansion that would result from a simple hybridization process within hydrogel crosslinks, we use a 3-strand crosslink architecture studied previously by Lin et al (11). Hydrogel squares with these crosslinks were fabricated according to the protocol listed in Methods (22). The resulting structures swelled to equilibrium due to solvent uptake in TAE/Mg$^{2+}$ buffer, after which the samples were immersed in TAE/Mg$^{2+}$ buffer containing 33.3 µM of F1 DNA strand that is complementary to the single stranded region within the crosslink. (B) Representative images of samples before and after treatment with F1. Approximately 24 hours after the addition of F1 strand, the gels had swelled uniaxially by roughly 5%. Brightness and contrast of the images was adjusted using ImageJ. Scale bars are 2 mm.

The inventors focused on hydrogels, crosslinked networks of polymers in water, where structural changes can cause extensive expansion or contraction of the material as a whole. To study biomolecular actuation, the inventors considered DNA-crosslinked polyacrylamide hydrogels (FIG. 1A, FIG. 5). DNA hybridization exchange processes can direct the release of particles or melt, form or stiffen these gels. Hybridization exchange can also induce size or shape changes of DNA-linked nanostructures, thin films and colloidal crystals. However, while the exchange of a DNA strand can cause DNA-crosslinked gels to swell by 10-15%, this amount is typically insufficient to change the shape of macroscale gel architectures (FIG. 6).

Hence, a critical challenge in making DNA triggered shape change hydrogels was to significantly increase the degree of swelling. The inventors postulated that swelling would increase if they lengthened crosslinks successively using a DNA hybridization cascade in which multiple DNA molecules are inserted into a duplex (FIG. 1A-B). To test this theory, the inventors designed DNA sequences, called "system 1," consisting of hydrogel crosslinks and corresponding hairpins, H1 and H2, for the cascade.

Figures 2A, 2B, 2C, 2D, 2E, 2F:
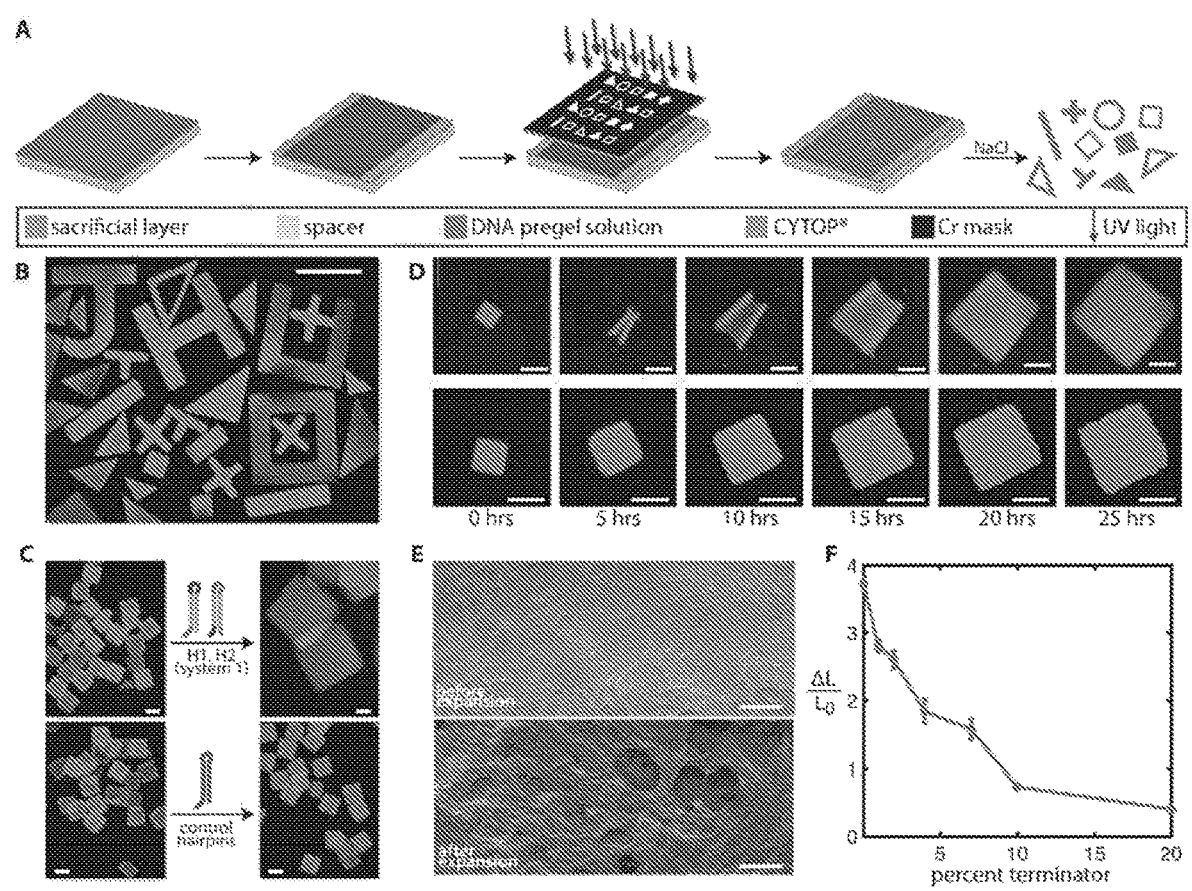
FIG. 2A-2F Photopatterning and hydrogel expansion. (A) Photopatterning process flow. (B) Fluorescence micrograph of hydrogels post-stained with Sybr Green I (22). Scale bar 5 mm. (C) Hydrogels expand dramatically in 20 µM polymerizing hairpin solution but not in 20 µM control hairpin solution. Scale bars 1 mm. (D) Time-lapse fluorescence micrographs of a hydrogel in polymerizing hairpins (top) and 98% polymerizing, 2% terminating hairpins (bottom). Scale bars 2 mm. (E) Scanning electron micrographs of hydrogels before and after DNA hybridization-driven expansion. Scale bars 300 µm. (F) Linear expansion of hydrogels with different terminator hairpin percentages (N=4). Error bars are one standard deviation.
Figure 8:
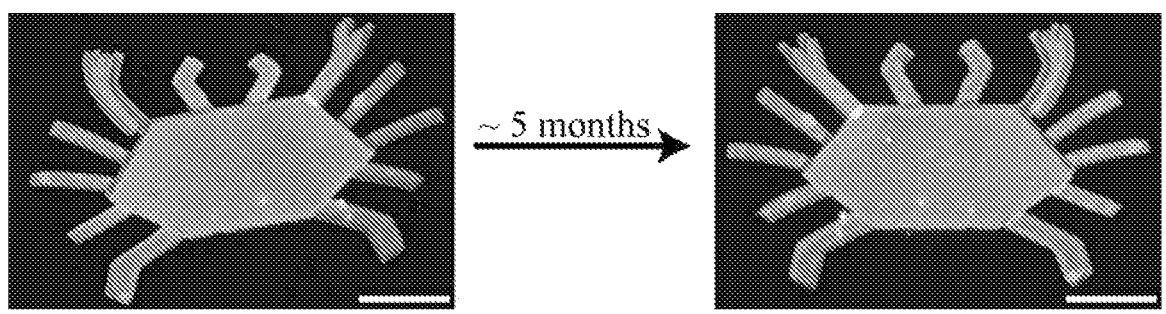
FIG. 8 Long-term stability of photopatterned poly(Am-co-DNA) gel architectures. Poly(Am-co-BIS)/poly(Am-co-DNA) crab architectures were prepared as described in Methods and FIG. 21. The micrographs show a typical crab (left) after fabrication and immersion in TAE/Mg$^{2+}$ buffer for 24 hours, and then (right) the same structure after storage at 4° C. in TAE/Mg$^{2+}$ buffer for roughly five months. Prior to imaging the crab after storage, the sample was flipped over in the course of handling. Scale bar is 2 mm.

Another challenge to enable addressable control was to reproducibly fabricate well-defined, multi-material DNA hydrogel shapes capable of arbitrary shape change in three dimensions. The inventors thus developed a photolithography process to pattern DNA hydrogels into precisely-defined architectures. While numerous photolithographic processes for silicon-based devices exist, protocols for photopatterning DNA hydrogels are largely absent, and the patterning process presents unique challenges. DNA-crosslinked hydrogels have orders of magnitude lower moduli as compared to silicon or even many polymers (FIG. 7) and also tend to adhere strongly to untreated glass and photomasks. Further, the UV light typically used for photopolymerization can damage DNA. The inventors developed a process in which an optimized amount of light exposure drives fabrication to reduce DNA damage. Further, the inventors created a process where structure thickness is controlled by solid spacers sandwiched between glass slides and a CAD-designed chrome mask with coatings and sacrificial layers that enable liftoff (FIG. 2A). Structures with millimeter- to centimeter-scale lengths and widths, and thicknesses from 15 to hundreds of microns with multiple domains could be patterned serially using mask alignment with registry to underlying layers. Multiple structures could be fabricated in parallel, and after fabrication, structures were stable in buffer at 4° C. for at least 4 months (FIG. 8).

The inventors fabricated 0.06×1×1 mm hydrogel squares containing system 1 crosslinks. In the presence of system 1 hairpins, the hydrogels expanded dramatically while the gels in buffer containing an alternate DNA sequence did not expand (FIG. 2C, D). Scanning electron micrographs of fixed samples showed that multiscale pores formed during expansion (FIG. 2E). Expansion occurred at a roughly linear rate (FIG. 9 and Movie S1) unabated.

Figure 9:
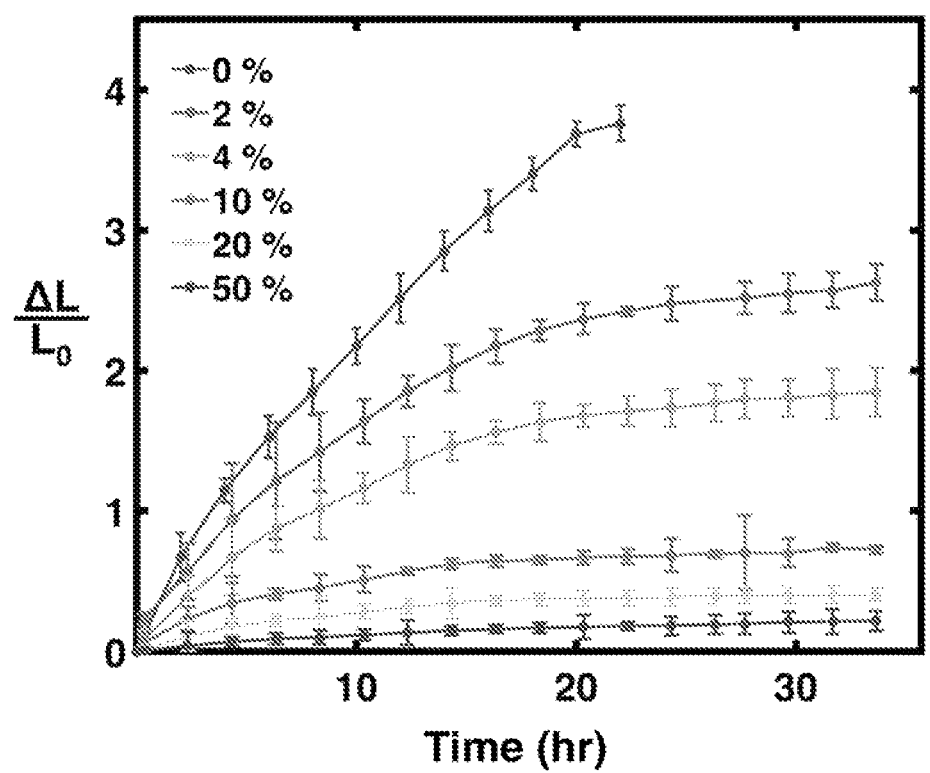
FIG. 9 The degree of swelling of poly(Am-co-DNA) gels can be controlled by adjusting the relative percentages of terminator and polymerizing hairpins. To assess the degree of expansion, poly(Am-co-DNA) gel squares and hairpin solutions with a total hairpin concentration of 20 µM of each of the two hairpin types (e.g. H1, H2)—with the percentages of terminator shown in the legend—were prepared following the protocols listed in the Methods section. Before the gel squares were added to the hairpin solution, they were allowed to take up buffer in a DNA-free solution for 24 hours. This DNA-free solution also contained 2×SYBR Green I nucleic acid stain to enable the gels to be imaged via fluorescence during swelling. For each percentage listed, 4 hydrogel squares were mixed with 3 mL of buffer containing the corresponding hairpin concentrations in a standard Petri dish. After the gels were added to the hairpin solutions, images of the gels were captured every 20 minutes in standard gel imager. At each time point, all four sides of each DNA gel sample were measured manually and averaged, then divided by the average lengths of the sides at time zero to obtain a uniaxial swelling measurement, which we denote as $\Delta L/L_0$. For samples that curled during expansion (some of the 0% and 2% terminator samples), the lengths of observable sides were averaged to calculate the degree of uniaxial swelling. Samples were tracked for 36 hours. Data for the 0% sample is not shown after 24 hours because the squares dimmed and their size could no longer be tracked reliably. Error bars represent a single standard deviation about the mean swelling value (N=4).

The inventors thus asked whether hydrogels could reliably expand to a desired final size. The inventors modified the sequences of the polymerizing hairpins to create "terminator hairpins" (FIG. 1C). By tuning the relative concentrations of polymerizing and terminator hairpins, the inventors could induce swelling of gels without curling to a well-defined final size (FIG. 2F, FIG. 9). Inclusion of 2% terminator hairpins produced high-degree but well-controlled swelling and was used in the remainder of our studies (Movie S2).

Figure 10:
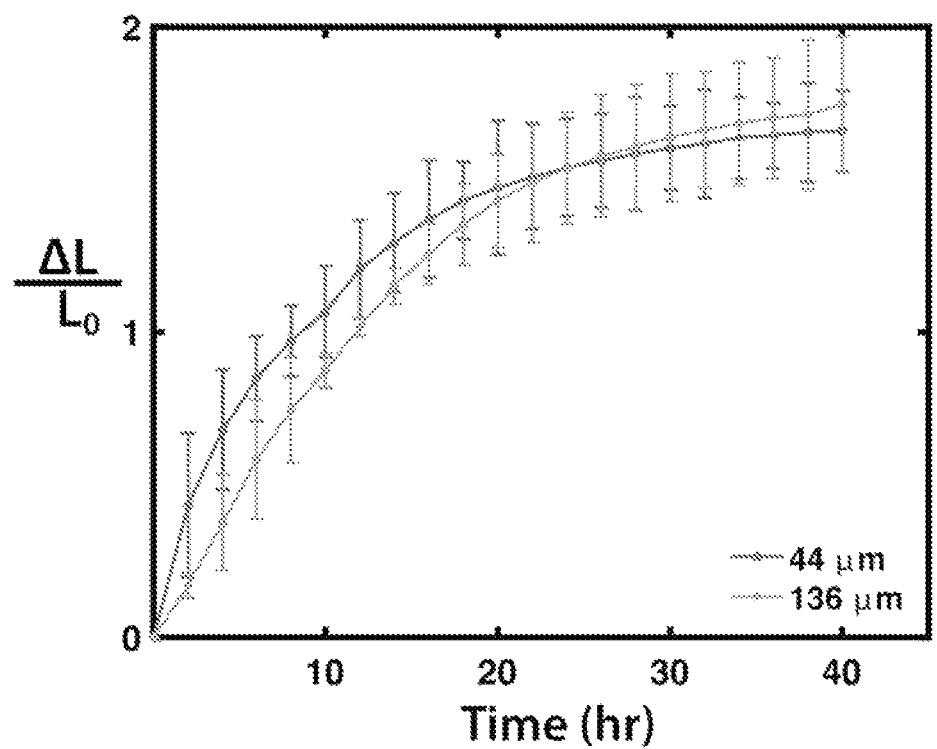
FIG. 10 Swelling of poly(Am-co-DNA) films of different thicknesses. The swelling kinetics of 1×1 mm, system 1 poly(Am-co-DNA) hydrogel squares, with measured thicknesses of 44 µm±3 µm and 136 µm±2 µm (mean±SD), in response to system 1 hairpins. The thickness was measured before the addition of hairpins for 4 samples using a confocal microscope as described in Methods. Uniaxial swelling is averaged for at least three samples for each thickness. Error bars represent a single standard deviation about the mean swelling value.
Figures 11A, 11B:
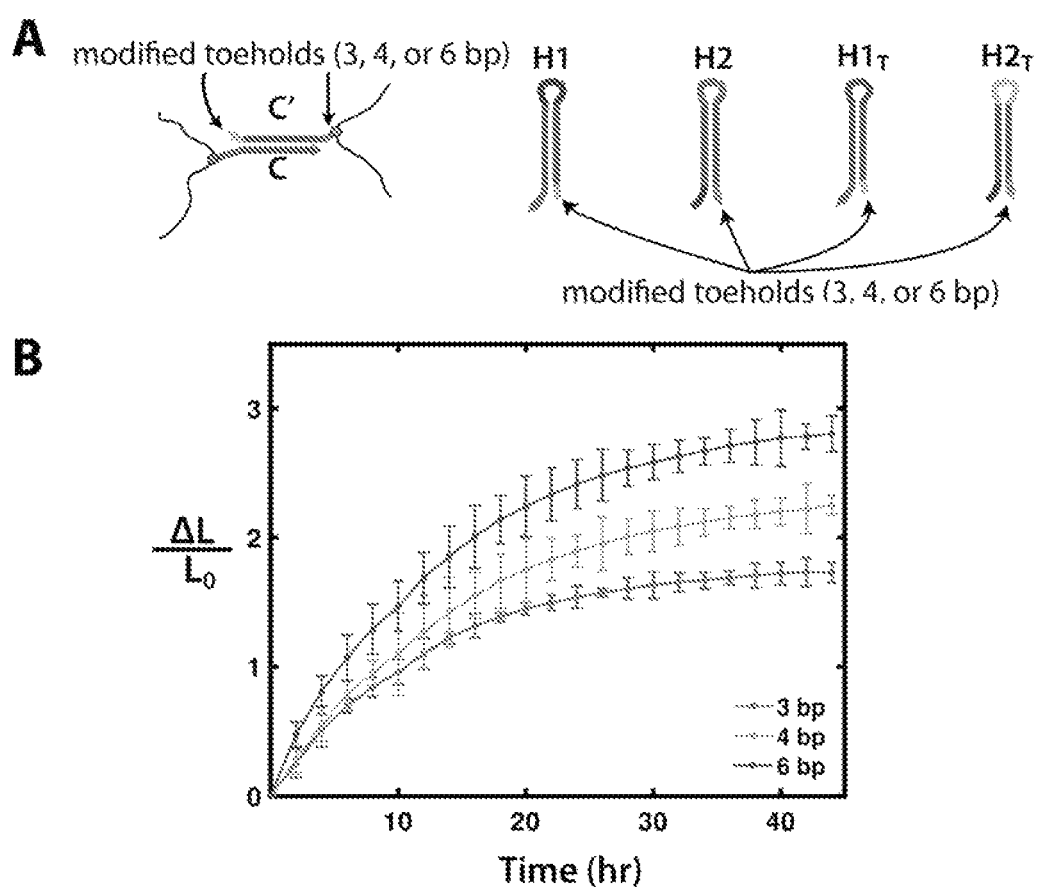
FIG. 11A-11B Swelling of poly(Am-co-DNA) films with different hairpin toehold lengths. (A) DNA crosslinker and hairpin systems containing either 3, 4 or 6 base pair toeholds were designed. The altered domains are indicated with arrows. The DNA crosslinker and hairpin system with the 3 bp toeholds are designated in the main text as "system 1." (B) The crosslinker complexes were prepared by annealing strand C with a C' strand containing 3 bp, 4 bp, or 6 bp toehold regions according to the protocol outlined in the Methods section. The 1 mm×1 mm×60 µm photopatterned poly(Am-co-DNA) hydrogel squares were swelled via the addition of a 20 µM, 2% terminator hairpin solution consisting of polymerizing and terminator hairpins with regions complementary to the 3 bp, 4 bp, or 6 bp toehold regions. Uniaxial swelling values are averaged for at least three samples for each toehold length. Error bars represent a single standard deviation about the mean swelling value.
Figure 12:
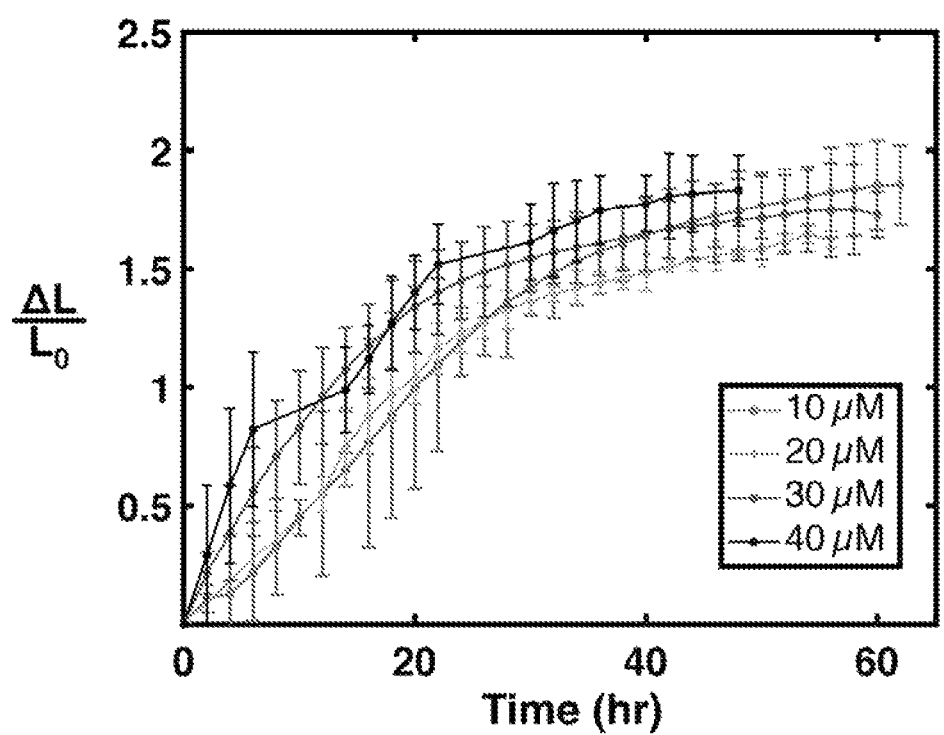
FIG. 12 Swelling of poly(Am-co-DNA) films with different total hairpin concentrations. The swelling kinetics of 1 mm×1 mm×14 µm photopatterned poly(Am-co-DNA) hydrogel squares containing system 1 crosslinker. The samples were placed in 3 mL of buffered solution containing 10, 20, 30 or 40 µM of overall hairpins, 2% of which was terminator hairpin monomers. Uniaxial swelling values are averaged for at least 3 samples for each hairpin concentration. Error bars represent a single standard deviation about the mean swelling value.

The inventors also found we could tune the swelling rate. Thinner films swelled slightly faster, but swelling rates do not appear limited by the diffusion of DNA hairpins (FIG. 10). Increasing the length of one of the toeholds that initiated the hairpin insertion process from 3 to 4 or 6 base pairs sped up expansion more significantly (FIG. 11), as did increasing hairpin concentration (FIG. 12).

By designing DNA sequences for three more systems of crosslinks and hairpins, we could addressably swell multiple domains (Table 1).

TABLE 1

DNA sequences of crosslinker and hairpin systems. All sequences were ordered from IDT in their lyophilized form and resuspended with TAE/Mg$^{2+}$. Sequences for acrydite-modified strands are preceded with a /5ACryd/ designation.

| DNA Strand | Sequence | SEQ ID NO: |
|---|---|---|
| *System 1 Strands* | | |
| S1-C | /5ACryd/TAAGTTCGCTGTGGCACCTGCACG | 1 |
| S1-C' | /5ACryd/CAACGTGCAGGTGCCACAGCGTGG | 2 |
| S1-H1 | CCACGCTGTGGCACCTGCACGCACCCACGTGCAGGTGCCACAGCGAACTTA | 3 |
| S1-H2 | TGGGTGCGTGCAGGTGCCACAGCGTAAGTTCGCTGTGGCACCTGCACGTTG | 4 |
| S1-H1$_T$ | CCACGCTGTGGCACCTGCACGTAGACTCGTGCAGGTGCCACAGCGAACTTA | 5 |
| S1-H2$_T$ | TGGGTGCGTGCAGGTGCCACAGCGGCCTAGCGCTGTGGCACCTGCACGTTG | 6 |
| S1-H1_FAM | /56-FAM/CCACGCTGTGGCACCTGCACGCACCCACGTGCAGGTGCCACAGCGAACTTA | 7 |
| Control Hairpin | GCTATCTAGCATCGCACGCTCTTTTTTGAGCGTGCGATGCTAGATGCGTAC | 8 |
| *System 2 Strands* | | |
| S2-C | /5ACryd/CTGTCTGCCTACCACTCCGTTGCG | 9 |
| S2-C' | /5ACryd/ATTCGCAACGGAGTGGTAGGCTTT | 10 |
| S2-H1 | AAAGCCTACCACTCCGTTGCGGAACCTCGCAACGGAGTGGTAGGCAGACAG | 11 |
| S2-H2 | AGGTTCCGCAACGGAGTGGTAGGCCTGTCTGCCTACCACTCCGTTGCGTTG | 12 |
| S2-H1$_T$ | AAAGCCTACCACTCCGTTGCGTCAAGCCGCAACGGAGTGGTAGGCAGACAG | 13 |
| S2-H2$_T$ | AGGTTCCGCAACGGAGTGGTAGGCAATCGTGCCTACCACTCCGTTGCGTTG | 14 |
| S2-H1_FAM | /56-FAM/AAAGCCTACCACTCCGTTGCGGAACCTCGCAACGGAGTGGTAGGCAGACAG | 15 |
| *System 3 Strands* | | |
| S3-C | /5ACryd/GGAACTCGGCAGTCGTCCAAGCGA | 16 |
| S3-C' | /5ACryd/ATCTCGCTTGGACGACTGCCGTAT | 17 |
| S3-H1 | ATACGGCAGTCGTCCAAGCGATACGGCTCGCTTGGACGACTGCCGAGTTCC | 18 |
| S3-H2 | GCCGTATCGCTTGGACGACTGCCGGGAACTCGGCAGTCGTCCAAGCGAGAT | 19 |
| S3-H1$_T$ | ATACGGCAGTCGTCCAAGCGACTGAGTTCGCTTGGACGACTGCCGAGTTCC | 20 |
| S3-H2$_T$ | GCCGTATCGCTTGGACGACTGCCGCAGATCCGGCAGTCGTCCAAGCGAGAT | 21 |
| *System 4 Strands* | | |
| S4-C | /5ACryd/ATCGGACCAGCACTTCGCCTACGG | 22 |
| S4-C' | /5ACryd/TGACCGTAGGCGAAGTGCTGGATG | 23 |
| S4-H1 | CATCCAGCACTTCGCCTACGGCTCTACCCGTAGGCGAAGTGCTGGTCCGAT | 24 |
| S4-H2 | GTAGAGCCGTAGGCGAAGTGCTGGATCGGACCAGCACTTCGCCTACGGTCA | 25 |
| S4-H1$_T$ | CATCCAGCACTTCGCCTACGGAAGGTGCCGTAGGCGAAGTGCTGGTCCGAT | 26 |
| S4-H2$_T$ | GTAGAGCCGTAGGCGAAGTGCTGGTGTATGCCAGCACTTCGCCTACGGTCA | 27 |
| *System 1: 4 Basepair Toehold* | | |
| S1_4bp-C' | /5ACryd/ACAACGTGCAGGTGCCACAGCGTGGA | 28 |
| S1_4bp-H1 | TCCGCGCTGTGGCACCTGCACGCACCCACGTGCAGGTGCCACAGCGAACTTA | 29 |
| S1_4bp-H2 | TGGGTGCGTGCAGGTGCCACAGCGTAAGTTCGCTGTGGCACCTGCACGTTGT | 30 |

TABLE 1-continued

DNA sequences of crosslinker and hairpin systems.
All sequences were ordered from IDT in their lyophilized
form and resuspended with TAE/Mg$^{2+}$. Sequences for acrydite-
modified strands are preceded with a /5ACryd/ designation.

| DNA Strand | Sequence | SEQ ID NO: |
|---|---|---|
| S1-4bp-H1$_T$ | TCCGCGCTGTGGCACCTGCACGAAACGGCGTGCAGGTGCCACAGCGAACTTA | 31 |
| S1-4bp-H2$_T$ | TGGGTGCGTGCAGGTGCCACAGCGCGACAACGCTGTGGCACCTGCACGTTGT | 32 |
| System 1: 6 Basepair Toehold ||||
| S1_6bp-C' | /5ACryd/GTACAACGTGCAGGTGCCACAGCGTGGATC | 33 |
| S1_6bp-H1 | GATCCGCGCTGTGGCACCTGCACGCACCCACGTGCAGGTGCCACAGCGAACTTA | 34 |
| S1_6bp-H2 | TGGGTGCGTGCAGGTGCCACAGCGTAAGTTCGCTGTGGCACCTGCACGTTGTAC | 35 |
| S1-6bp-H1$_T$ | GATCCGCGCTGTGGCACCTGCACGAAACGGCGTGCAGGTGCCACAGCGAACTTA | 36 |
| S1-6bp-H2$_T$ | TGGGTGCGTGCAGGTGCCACAGCGGCCTAGCGCTGTGGCACCTGCACGTT | 37 |
| 3-Strand Crosslink System Strands ||||
| SA1 | ACGGAGGTGTATGCAATGTC | 38 |
| SA2 | CATGCTTAGGGACGACTGGA | 39 |
| L3 | TCCAGTCGTCCCTAAGCATGTGTTCGACGGTACAAGAAGAGGGTTACGCTAATGAGTGCTGACATTGCATACACCTCCGTA | 40 |
| F1 | AGCACTCATTAGCGTAACCCTCTTCTTGTACCGTCGAACAGATAGAGCTG | 41 |

Figure 13:
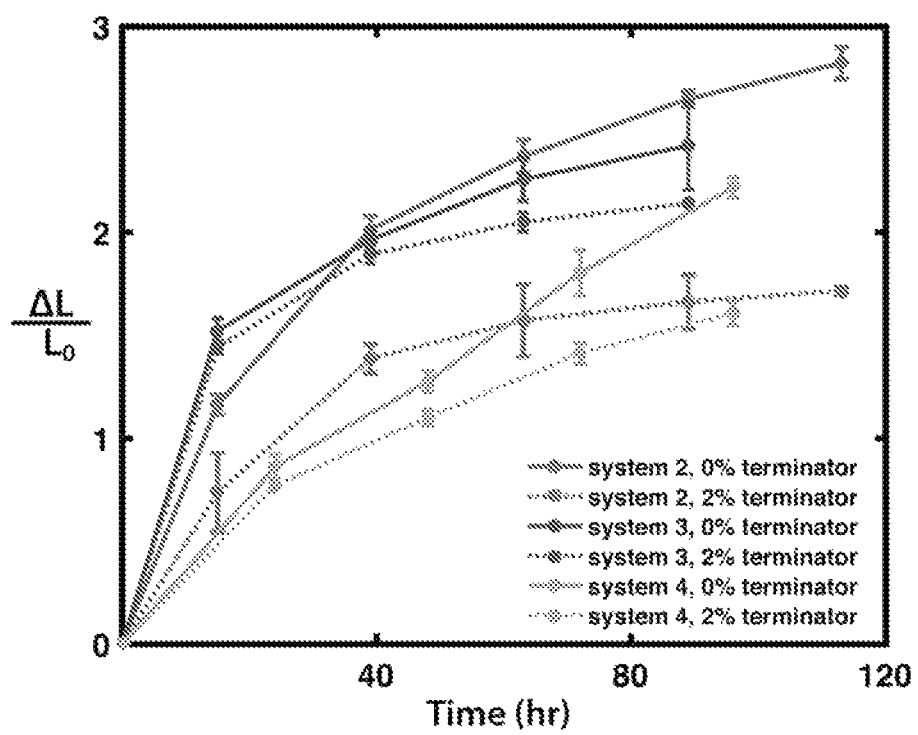
FIG. 13 DNA-driven expansion of poly(Am-co-DNA) gels crosslinked by different sequences in response to their respective polymerizing hairpins. Poly (Am-co-DNA) gel samples were prepared as described in the Methods section with either system 2, system 3 or system 4 crosslink complexes. All gel samples were 60 µm×1 mm×1 mm in size. To visualize the gels, samples were stained overnight in 2×SYBR Green I nucleic acid stain and subsequently washed in fresh TAE/$Mg^{2+}$ buffer before being added to a 20 µM hairpin solution containing either 0% or 2% terminator hairpin and were monitored via fluorescence microscopy. Sample dimensions were measured manually using ImageJ software. The error bars show a single standard deviation about the mean swelling value of at least four samples in a particular hairpin solution.
Figure 14:
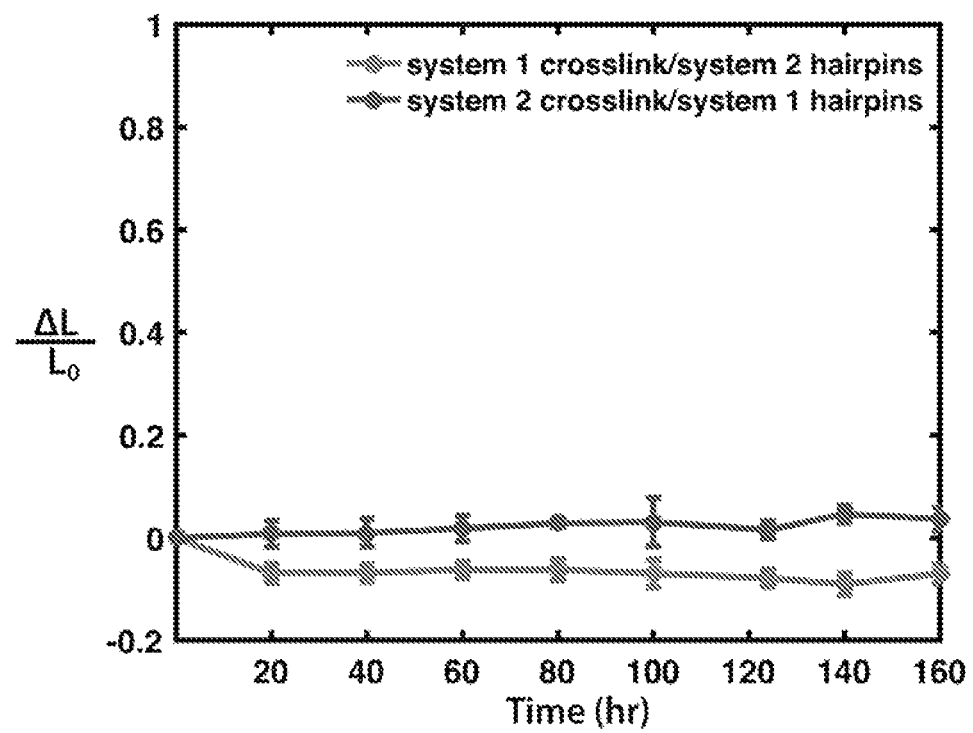
FIG. 14 Poly (Am-co-DNA) gels do not expand in solutions of non-complementary hairpin types. Poly (Am-co-DNA) gels containing either system 1 or system 2 crosslinks were prepared following the protocol listed in the Methods section. The gels were stained overnight in 2×SYBR Green I nucleic acid stain and were subsequently washed in fresh TAE/$Mg^{2+}$ buffer prior to adding the DNA hairpin solution. Four gel samples crosslinked with system 1 DNA complexes were placed in a 20 µM solution of system 2 polymerizing hairpins (with 0% terminator). Conversely, four gel samples crosslinked with system 2 DNA complexes were placed in a 20 µM solution of system 1 polymerizing hairpins (with 0% terminator). The gels were monitored via fluorescence microscopy; sample dimensions were manually measured using ImageJ software. The error bars represent a single standard deviation about the mean swelling value of all the samples exposed to a given hairpin solution.
Figure 15:
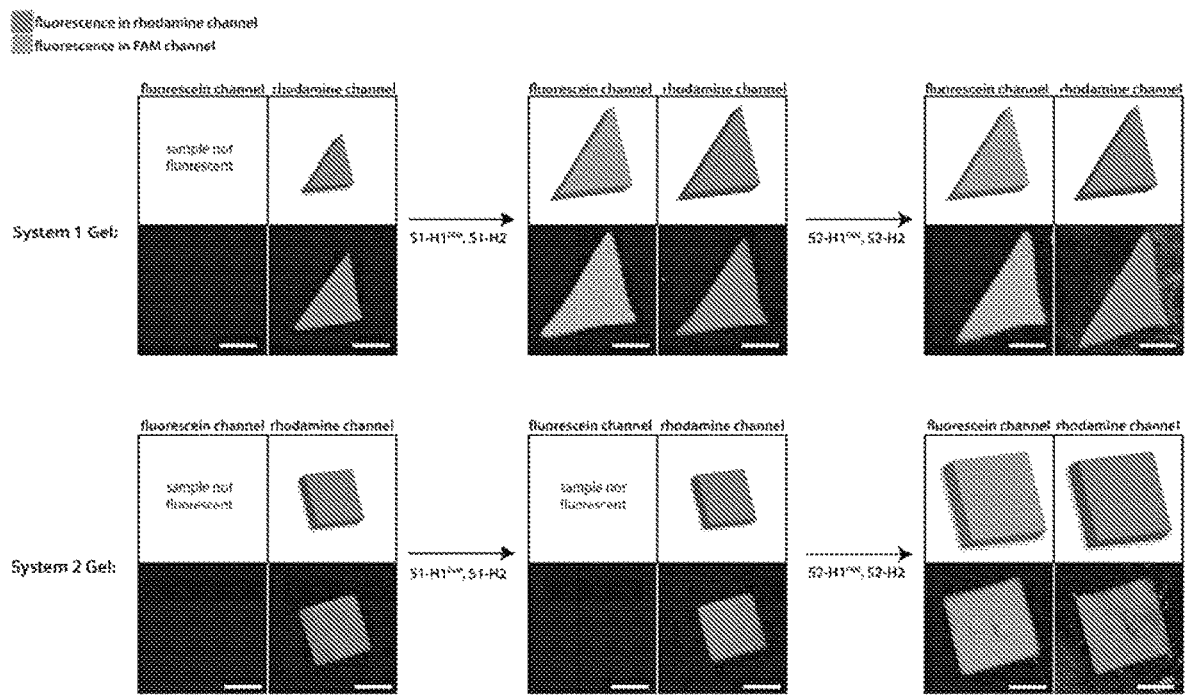
FIG. 15 Sequence-specific incorporation of hairpins into poly(Am-co-DNA) gels during expansion. To verify that DNA hairpins accumulate in poly(Am-co-DNA) gels when expansion occurs but not otherwise, two sets of poly(Am-co-DNA-co-rhodamine) gels—one crosslinked with system 1 and the other crosslinked with system 2—were each first exposed to a solution of system 1 hairpins, then exposed to a solution of system 2 hairpins. The H1 polymerizing hairpin in each system was labeled on the 5' end with a FAM fluorophore. The system 1 gel was patterned as a triangle, whereas the system 2 gel was patterned as a square so that the type of crosslinks within the gel could be identified by the gel's shape. Before the addition of hairpins, both samples were visible under a Nikon AZ100 epifluorescence microscope using a G-2E/C filter cube (528-533 nm excitation, 590-650 bandpass) because of the rhodamine dye; no significant fluorescence was observed when imaging with the FAM filter. After the addition of 19.6 µM of FAM-labeled system 1 hairpins and 0.4 µM unlabeled system 1 terminator hairpins (i.e. a 2% fraction of the total hairpins, following other experiments), the gel with system 1 crosslinks (the triangle) expanded and was readily visible in the FAM channel, whereas the other shape was not visible. The samples were then transferred to a solution of 19.6 µM of FAM-labeled system 2 hairpins and 0.4 µM unlabeled system 2 terminator hairpins (i.e. a 2% fraction of the total hairpins, following other experiments). In this solution the system 1 crosslinked-gel did not change significantly in size or brightness, but the system 2-crosslinked gel expanded and became visible in the FAM channel. Scale bars are 1 mm.

Hydrogels with each crosslink type swelled extensively in response to their corresponding hairpins but not to others (FIGS. 13-14 Hairpins also accumulated only in their corresponding gels (FIG. 15).

Figure 16:
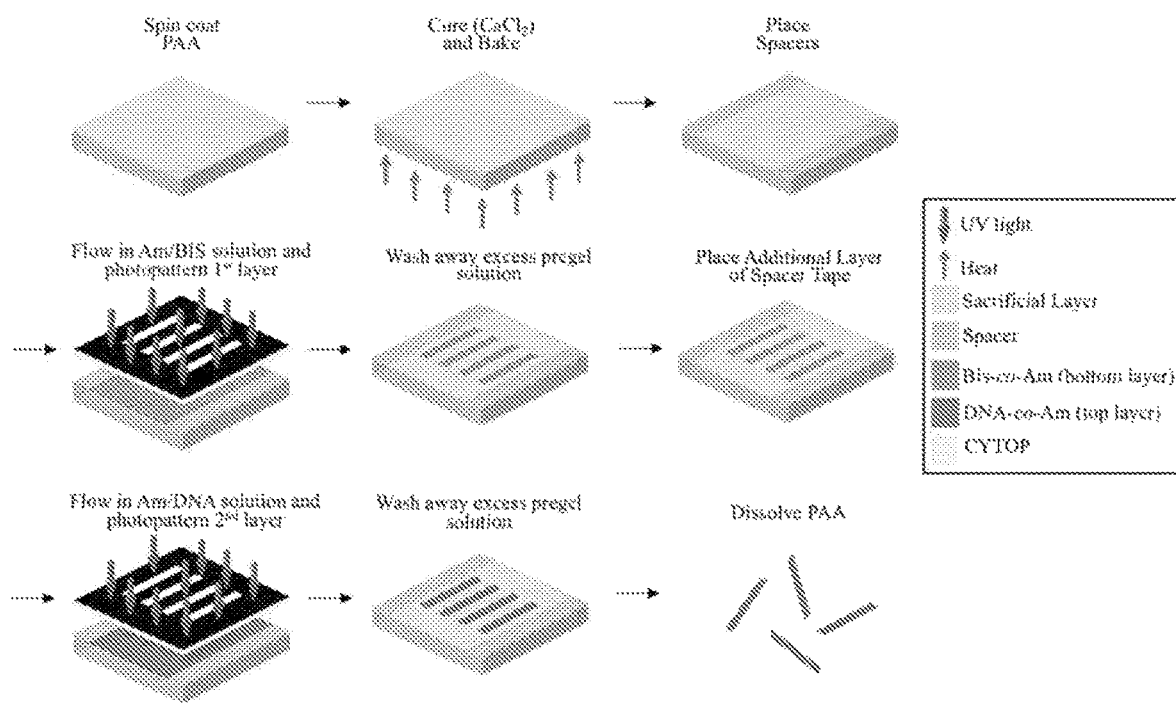
FIG. 16 Process Diagram for poly(Am-co-BIS)/poly(Am-co-DNA) Hydrogel Bilayer Fabrication. Parameters such as bake temperature/time, spacer thickness and solution concentrations are given in the Methods section. After each UV exposure, the resulting samples were washed with TAE/$Mg^{2+}/Ca^{2+}$ buffer to remove unpolymerized monomers and DNA crosslinks. The calcium cations in the buffer prevent degradation of the ionic crosslinks of the poly(acrylic acid) sacrificial layer.
Figure 17:
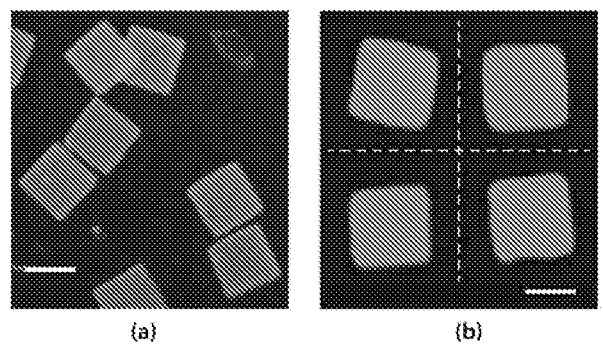
FIG. 17 Swelling of poly(Am-co-BIS) and poly(Am-co-DNA) hydrogels after patterning due to solvent uptake. Both the poly(Am-co-BIS) and poly(Am-co-DNA) gels swell in TAE/Mg' buffer after photopatterning due to solvent uptake.

To investigate how to design the shape change of composite multi-domain architectures, the inventors characterized DNA sequence-driven curling of model bilayer beams (FIG. 3A, FIG. 16). While the beams curled only slightly in DNA-free buffer due to different rates of solvent uptake by BIS-crosslinked and DNA-crosslinked gels (FIG. 3A, FIG. 17), they curled much more tightly when subsequently exposed to their corresponding hairpins (FIG. 3A, FIG. 18).

The inventors applied finite element analysis to study bilayer curving caused by DNA-induced swelling (see a description of Finite Element Analysis provided below). The stress response of the gel was assumed to be the sum of an elastic component for the entropic response of the polymer network, and the solvent pressure acting on the network derived from Flory-Huggins theory. The inventors determined the final shape of a structure after DNA-driven swelling by changing the Flory-Huggins parameter in the DNA- and BIS-crosslinked gel layers to achieve the experimentally measured volumetric swelling ratios within the different layers (FIG. 3A) and then solving for the displacement field in the bilayer.

To set the remaining model parameters, the inventors measured the Young's modulus of a BIS-crosslinked gel via an unconfined compression test as 2.2 kPa (FIG. 19), which corresponds to a shear modulus of 733 Pa assuming mechanical incompressibility (supplementary text). The inventors then used the finite element model to fit the shear modulus of the DNA gel, 229 Pa, to obtain the curvature of the bilayer measured in experiments.

The inventors found that the effects of varying DNA gel thickness, modulus, and the degree of swelling (FIG. 3B) can be described by a simple design rule for the curvature K=Cη+K$_D$ of the bilayer, where η is the bilayer ratio (24) given by (supplementary text), $$\eta = \frac{\frac{E_{DNA} t_{DNA}}{E_{BIS} t_{BIS}^2} \Delta\theta \left(1 + \frac{t_{DNA}}{t_{BIS}}\right)}{1 + 4\left(\frac{t_{DNA}}{t_{BIS}}\right)\left(\frac{E_{DNA}}{E_{BIS}}\right) + 6\left(\frac{t_{DNA}}{t_{BIS}}\right)^2\left(\frac{E_{DNA}}{E_{BIS}}\right) + 4\left(\frac{t_{DNA}}{t_{BIS}}\right)^3\left(\frac{E_{DNA}}{E_{BIS}}\right) + \left(\frac{t_{DNA}}{t_{BIS}}\right)^4\left(\frac{E_{DNA}}{E_{BIS}}\right)^2}$$

(1)

$E_{DNA}$ and $E_{BIS}$ are the Young's modulus (Pa) of the DNA and BIS gels, $t_{DNA}$ and $t_{BIS}$ the thickness (mm) of the DNA and BIS gels, and $\Delta\theta$ the difference in the volumetric swelling ratio between the DNA and BIS gels. The initial curvature $K_0$=0.2 mm$^{-1}$ and proportionality constant C=0.21 were obtained from a linear regression of our simulation results (FIG. 3B).

This design rule indicates that curvature is more sensitive to the DNA gel swelling ratio ($\Delta\theta$), with which the curvature varied linearly, than to the shear modulus or thickness of the DNA gel layer. The high degree of swelling was thus essential for extensive shape change. Further, there is an optimum thickness of the DNA gel for which curvature is maximized (FIG. 3C). A DNA gel layer that is too thin cannot exert enough force to bend the bilayer, while a DNA gel layer that is too thick is negligibly affected by the BIS gel layer and undergoes uniform swelling rather than folding. The parameter study predicts that the high degree of swelling of the DNA gel could cause millimeter- to centimeter-thick structures to bend. For example, an initially flat 10 mm long by 7.23 mm-thick bilayer with the optimum DNA gel thickness and the maximum swelling ratio 3.72±0.11 should fold into a complete circle after sequence-specific DNA-triggered actuation.

Figures 4A, 4B, 4C, 4D, 4E, 4F, 4G:
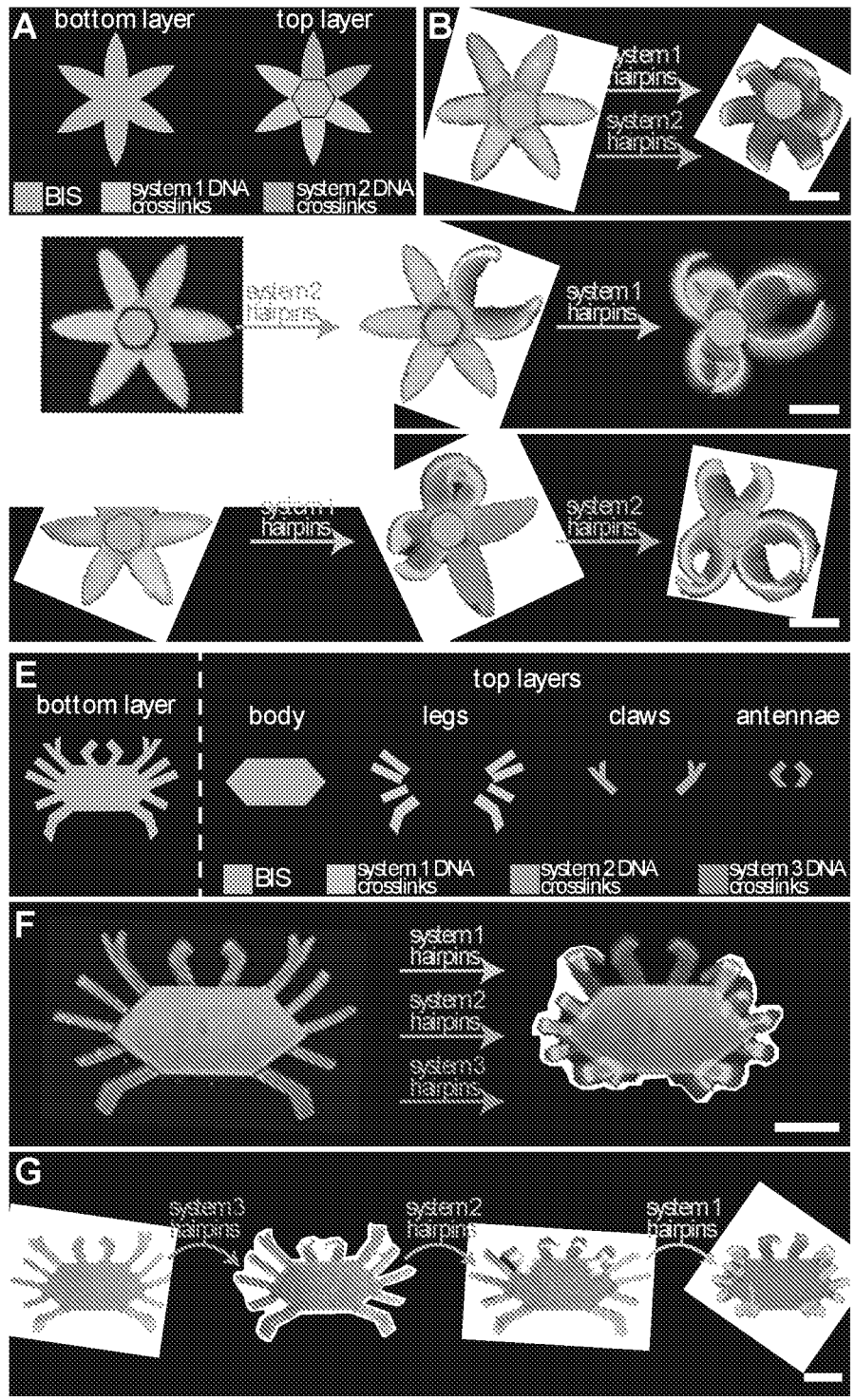
FIG. 4A-4G DNA sequence-programmed shape change of macroscopic hydrogel shapes. (A) Schematic of a six-petal flower (22). (B) All petals curl in response to both system 1 and 2 hairpins. (C-D) Specific petals actuate in response to system 1 or system 2 hairpins alone. Petals can be actuated in series. (E) Hydrogel crab schematic. (F) Legs, claws and antennae all actuate in response to system 1-3 hairpins. (G) Serial actuation. Solutions contained 20 µM of each hairpin, 98% polymerizing hairpins, 2% terminating hairpins. DNA-crosslinked hydrogel domains are differentially colored for clarity. Scale bars: 1 mm B, C, and D, 2 mm F and G.

The inventors next explored how structures with multiple, different DNA sequence-responsive hydrogels would differentially change shape in response to different hairpin inputs. The inventors fabricated flowers where two groups of petals responded to two different sequences (FIG. 20, FIG. 4A). In the presence of both sets of sequences, all the petals folded (FIG. 4B). Each set alone caused its corresponding petals to fold, and petals could be folded in sequence through stepwise exposure (FIG. 4C-D). The inventors attribute twisting of the petals to misalignment errors during photopatterning of the gel layers. We further fabricated hydrogel "crab" devices, in which the antennae, claws and legs each curled in response to respective sequences, either all at once or sequentially with appropriate sequence inputs as designed (FIG. 4E-G, FIG. 21). The structures remained in their actuated states for at least 60 days (FIG. 22).

Biological tissues demonstrate the versatility and functionality of shape change driven by biomolecules, where different cues and their concentrations determine which responses occur. The inventors have demonstrated how specific biomolecular signals can also determine which domains of a synthetic material should change in shape and by how much. The DNA oligonucleotide signals used could be the outputs or inputs to molecular sensors and circuits. Coupling these circuits to hydrogels could allow materials to exhibit multistage, goal-directed behaviors currently impossible to achieve. Because hairpin insertion and removal can occur without the crosslink breaking, altering the extension reaction's bias could allow crosslink contraction and potentially, reversible actuation. Finally, our wafer-scale patterning approach offers the potential for scale-up and integration with existing optical, logic and memory devices.

Description of Finite Element Analysis:

Finite Element Model of BIS/DNA Bilayer Actuation Various theoretical hydrogel models have been developed in recent years to explain the coupled mechanical and stimuli-responsive swelling behavior of hydrogels and to support the design of active hydrogel structures. The inventors previously developed a constitutive theory for thermoresponsive hydrogels and showed that it can accurately predict the equilibrium configuration of pNIPAM gels and composite structures in response to a temperature and mechanical stimuli. In their model, the inventors neglected the kinetics of diffusion and assumed that the hydrogel remained in equilibrium throughout the deformation, which was justified by the short diffusion time permitted by micrometer-scale thickness of the bilayer structures.

For the constitutive model, the inventors first defined a deformation field $x=\varphi(X)$, that maps material points X in the initial undeformed dry polymer network configuration to spatial points x in the current deformed hydrogel configuration. The deformation gradient tensor is defined as $F=\partial z/\partial X$ from the initial configuration to the current configuration. To model the stress-free swelling of the gel, the deformation gradient tensor F is further decomposed into a mechanical part, $F_e$, and a swelling part, $F_s$:

$$F=F_e F_s, \quad (1)$$

where $F_s=\varphi^{-1/3}I$ and $\varphi$ is the polymer network volume fraction of the hydrogel. The polymer network volume fraction is expressed as $\varphi=1/(1+vc)$, where v is the volume per solvent molecule and c is the number of solvent molecules per polymer network volume. Since the gel is initially swollen, the inventors define the swollen undeformed configuration as the reference configuration, and a deformation gradient f mapping from the stress-free reference configuration to the final swollen deformed configuration:

$$f=\varphi_0^{1/3}F, \quad (2)$$

where $\varphi_0$ is the polymer network volume fraction in the reference state. The left Cauchy-Green deformation tensor and its first invariant are defined as, $b=FF^T$ and $I_b=\text{tr}(b)$. The b tensor can be expressed in terms of its principle values and principle directions as:

$$b=\Sigma_{i=1}^3 \lambda_i^2 \otimes n_i, \quad (3)$$

and $\bar{\lambda}_i=\varphi_0^{1/3}\lambda_i$ are the corresponding principal stretches of f tensor. The change of volume from initial dry configuration to final configuration is related to the mechanical component and swelling component as: $J=\det[F]=\det[F_e]\det[F_s]=J_e\varphi^{-1}$. The inventors assumed that the free energy density of hydrogel could be additively decomposed into a mechanical term arising from the stretching of a polymer network and a term describing the mixing energy of the polymer network and solvent system:

$$\Psi=\Psi_{mechanical}(I_b,J_e)+\Psi_{mixing}(\varphi). \quad (4)$$

The quasi-incompressible Neo-Hookean model is used to describe the strain energy of the network (39):

$$\Psi_{mechanical}(I_b, J_e) = \frac{G}{2}(I_b - 3 - 2\log J) + \frac{K}{4}(J_e^2 - 2\log J_e - 1), \quad (5)$$

where G and K are the shear modulus and bulk modulus of the polymer network respectively. The Flory-Huggins model (23) is used to express the free energy of mixing:

$$\Psi_{mixing}(\varphi) = \frac{RT}{v\varphi}[(1-\varphi)\log(1-\varphi) + \chi\varphi(1-\varphi)], \quad (6)$$

where R is the gas constant, and $\chi$ is the Flory-Huggins parameter.

The Cauchy stress tensor is derived from the free energy density as $\sigma=(1/J)(\partial\Psi/\partial F)F^T$, and the chemical potential is defined as $\mu=\partial\Psi/\partial c$, where c is the number of solvent molecules per polymer network volume:

$$\sigma = \sum_{i=1}^3 \left\{ \frac{G\varphi_0}{\bar{\lambda}_1\bar{\lambda}_2\bar{\lambda}_3}(\varphi^{-2/3}\lambda_i^2 - 1) + \frac{K\varphi_0}{2\bar{\lambda}_1\bar{\lambda}_2\bar{\lambda}_3}\left[\left(\frac{\varphi}{\varphi_0}\bar{\lambda}_1\bar{\lambda}_2\bar{\lambda}_3\right)^2 - 1\right]\right\} n_i \otimes n_i, \quad (7)$$

$$\mu = RT[\log(1-\varphi) + \varphi + \chi\varphi^2] - \frac{Kv\varphi}{2}\left[\left(\frac{\varphi}{\varphi_0}\bar{\lambda}_1\bar{\lambda}_2\bar{\lambda}_3\right)^2 - 1\right]. \quad (8)$$

The constitutive model was implemented into TAHOE (Sandia National Laboratories) for finite element simulation of hydrogel structures. The shear modulus of the DNA hydrogel was obtained from swelling experiments and finite element analysis of the folding of DNA/BIS hydrogel bilayer beams. For the swelling experiments of DNA/BIS hydrogel bilayer beams, the dimensions in the hydrated state before adding DNA hairpins were l=4.925 mm in contour length and w=0.528 mm in width. The thicknesses of the DNA and BIS layers were $t_{DNA}$=60.6 μm, $t_{BIS}$=71.6 μm. The initial bilayer curvature in the hydrated state was measured to be 0.2 mm$^{-1}$. DNA hairpins were added to the bilayer bars to induce sequence-driven swelling. The average curvature of swollen bilayer bars under equilibrium was measured to be 1.0 mm$^{-1}$. The dimensions of both layers in equilibrium were also measured and the volumetric swelling ratios of the DNA gel and BIS gel were calculated to be 6.91 and 4.42 respectively. The sequence-induced swelling of the BIS gel was caused by the interpenetration of DNA and BIS gels during the layer-by-layer fabrication process, which was confirmed by confocal imaging.

Finite Element Model of Swelling-Induced Folding of a Hydrogel Bilayer

For the finite element model of the bilayer beam, the simulation started from the initial hydrated configuration, where the initial curvature of bilayer was 0.2 mm$^{-1}$ as measured in the experiments. The model geometry had the same dimensions as measured for the fully hydrated photopatterned bilayers (FIG. 23). The mesh was discretized using trilinear hexahedral elements. The dimensions of the elements were $l_e$=61.6248 μm in length and $w_e$=52.8 μm in width, and the thicknesses were $l_e^{DNA}$=15.15 μm, $t_e^{BIS}$=17.9 μm for DNA and BIS gel elements. The displacements at X=0, Y=0 and Z=0 were fixed. The Young's modulus of the BIS gel in the fully hydrated state was measured to be 2.2 kPa from unconfined compression tests (FIG. 19). Assuming that the gels were mechanically incompressible resulted in 733 Pa for the shear modulus of the BIS gel. The bulk modulus was set to K=1000G to enforce mechanical incompressibility of the polymer network. Though the BIS gel exhibited DNA interpenetration, we assumed that the shear modulus of the BIS gel did not change significantly during DNA-driven swelling. It was difficult and expensive to prepare and fully expand a DNA-crosslinked hydrogel via hairpin incorporation (in a 2% terminating hairpin solution) large enough to perform a compression test with using our equipment, because of the time required for diffusion of enough DNA hairpins into a very thick gel sample to complete expansion. Handling expanded hydrogels was also very difficult due to the softening that occurs during DNA-driven swelling. To determine the modulus of DNA gel in the fully swollen state, we therefore applied the finite element model to determine the shear modulus of the DNA gel needed to obtain the curvature measured for the actuated bilayer. The DNA sequence-driven swelling was achieved by varying the Flory-Huggins interaction parameter $\chi$. The Flory-Huggins interaction parameters for the hydrated state and the DNA-actuated state were selected so that the free swelling ratio of the gels in simulation matched the results from swelling experiments of BIS/DNA hydrogel bilayers (FIG. 18). The average volumetric swelling ratios measured for 12 specimens were 6.91 and 4.42 for the DNA and BIS layers. The parameters used in the model are listed in Table S2.

TABLE S2

Parameters determined for DNA and BIS hydrogels.

| Parameters | G (Pa) | $\chi$ for the hydrated state | $\chi$ for the DNA-actuated state |
|---|---|---|---|
| DNA gel | 229 | 0.55 | 0.51 |
| BIS gel | 733 | 0.55 | 0.51 |

The initial polymer network volume fraction coo was obtained by solving equations and with the conditions σ=0 and μ=0. The Flory-Huggins interaction parameters were continuously decreased from 0.55 to 0.51, and at each value the deformation gradient field f(X) and polymer network volume fraction φ(X) were determined by the finite element analysis. The inventors performed the finite element simulations while varying the shear modulus of the DNA gel from 2.29 to 350 Pa, and calculated for each case the equilibrium curvature of the bilayer bar at the equilibrium swelling. The equilibrium curvature of the bilayer was calculated as follows. The deformed positions of the points on the midline of the bilayer inner surface were obtained from the simulation result. The inventors determined the radius of the best fit circle to the points using the method of least squares. The curvature was then calculated by taking the inverse of the radius. The calculated curvature of the bilayer was compared to the curvature of the actuated bilayer measured in experiments to determine the equilibrium shear modulus of the DNA gel. A shear modulus of 229 Pa produced the best fit to the experimentally measured bilayer average curvature at steady state.

Parameter Study

The inventors applied the model to investigate the effect of the thickness, shear modulus and volumetric swelling ratio of DNA gel on the curvature of folding BIS/DNA gel bilayer bars. The inventors first varied the DNA gel thickness from 13 μm to 70 μm while keeping the BIS layer thickness of 71.6 μm, DNA gel shear modulus of 229 Pa and volumetric swelling ratio of 6.91 unchanged. Next, the inventors kept the DNA gel thickness and volumetric swelling ratio constant at 60.6 μm and 6.91, respectively, and adjusted the DNA gel shear modulus from 2.29 to 350 Pa. The inventors then kept the DNA gel thickness of 60.6 μm and shear modulus of 229 Pa unchanged, and varied the DNA gel volumetric swelling ratio from 5 to 12. These parameters were varied independently and in each simulation the average equilibrium curvature of actuated DNA/BIS gel bilayer was calculated using the method described in the above section.

Theoretical solutions for the curving of thin film-thick substrate bilayer system have been derived based on the century-old Stoney formula for stresses in the deposited thin film. This formula assumes small strains and rotations, and that the material of each layer is isotropic, homogeneous, and linear elastic. For the case where the thicknesses of each layer are comparable (e.g., $t_{BIS} \sim t_{DNA}$), Freund et al. (24) derived the modified Stoney formula for the bilayer curvature, which for an initially flat bilayer can be expressed as, K=2η. The bilayer ratio, η, is given by, $$\eta = \frac{\frac{E_{DNA} t_{DNA}}{E_{BIS} t_{BIS}^2} \Delta\theta \left(1 + \frac{t_{DNA}}{t_{BIS}}\right)}{1 + 4\left(\frac{t_{DNA}}{t_{BIS}}\right)\left(\frac{E_{DNA}}{E_{BIS}}\right) + 6\left(\frac{t_{DNA}}{t_{BIS}}\right)^2\left(\frac{E_{DNA}}{E_{BIS}}\right) + 4\left(\frac{t_{DNA}}{t_{BIS}}\right)^3\left(\frac{E_{DNA}}{E_{BIS}}\right) + \left(\frac{t_{DNA}}{t_{BIS}}\right)^4\left(\frac{E_{DNA}}{E_{BIS}}\right)^2}$$ (9)

for the case when the Poisson's ratio is the same in each layer. The $E_{DNA}$ and $E_{BIS}$ are the Young's moduli of the DNA and BIS gels (Pa); $t_{DNA}$ and $t_{BIS}$ are the thicknesses of DNA and BIS gel layers (mm); and Δθ is the difference in the volumetric swelling ratio between the DNA and BIS gels. The modified Stoney formula provided a poor prediction of the simulation results for the curvature of the BIS/DNA gel bilayer, likely because the simulations exhibited large deformation and nonlinear elastic behavior, which violated the assumptions of the theory. However, the inventors found that the simulation results for the curvature change scaled with the bilayer ratio. Plots of the curvature as a function of the bilayer ratio for all cases of the parameter study fell on a straight line of the form $K=C\eta+K_0$ (FIG. 3B in the main text). A linear regression returned $C=0.21$ for the proportionality constant and $K_0=0.2$ mm$^{-1}$ for the initial curvature, which agreed with the average initial curvature of the bilayers measured in the hydrated state 0.2057 mm$^{-1}$.
The bilayer ratio $\eta$ depends nonlinearly on the modulus and thickness ratio of the DNA and BIS gels, and depends linearly on the difference in the volumetric swelling ratio. FIG. 24 shows the variation of the equilibrium bilayer curvature with the DNA gel shear modulus, BIS gel shear modulus, DNA gel thickness and volumetric swelling ratio. Increasing the DNA gel thickness or shear modulus increased the flexural stiffness of the DNA gel resulting in a higher curvature, signifying a more curved bilayer. Likewise, increasing the DNA gel volumetric swelling ratio increased the curvature. As shown in the figure, the curvature was most sensitive to the DNA gel volumetric swelling ratio. Changing the BIS gel shear modulus had a small effect on the final curvature, with a less stiff BIS gel leading to only slightly more folding. In contrast, the shear modulus of the DNA gel had a pronounced effect. When the DNA gel shear modulus was increased from 2.29 to 850 Pa, the equilibrium curvature increased asymptotically until the DNA gel shear modulus reached the BIS gel shear modulus. In FIG. 3C the inventors plotted the equilibrium bilayer curvature as a function of the DNA layer thickness $t_{DNA}$ for the BIS layer thickness of 0.0516~0.0916 mm. Increasing the BIS gel thickness resulted in a lower curvature due to the increased flexural stiffness of BIS layer. However, the effect of varying the thickness of the DNA gel was more complicated. For each BIS gel thickness, there was an optimum thickness of DNA gel for which the bilayer curvature was maximized. For example, the optimal DNA gel thickness was 0.0606 mm for the BIS gel thickness of 0.0716 mm. The bilayer curvature decreased for larger and smaller values of DNA gel thickness. A DNA gel layer that is too thin did not exert enough force to bend the bilayer, while a DNA gel layer that is too thick was negligibly affected by the BIS gel layer and underwent uniform swelling rather than inducing folding. The optimal thickness increased with the BIS gel thickness. For the BIS gel thicknesses of 0.0516, 0.0716 and 0.0916 mm, the optimum DNA gel thicknesses were 0.042, 0.0606 and 0.0698 mm respectively.

The parameter study also showed that the high degree of swelling of the DNA gel should allow millimeter to centimeter sized bilayer structures to achieve a large shape change. For example, we asked whether a 10 mm long flat bilayer beam that was also several millimeters thick (as opposed to 0.1 mm or less as we had studied previously) could fold into a complete circle. The relation obtained from the parameter study was $K=0.21\eta+0.2$, where 0.2 mm$^{-1}$ represents the initial curvature of the bilayers in the hydrated state. Using the relation $K=0.21\eta$ and assuming the 10 mm long bilayer beam was initially flat, the inventors determined that the 10 mm long bilayer with the optimum DNA gel thickness can be as thick as 7.23 mm and still fold into a complete circle for the maximum experimentally measured swelling ratio of 3.72±0.11.

For similar DNA-crosslinked polyacrylamide gels, the average molecular weight between crosslinks was measured using diffusion ordered NMR spectroscopy (DOSY) to be roughly 160,000 (Adv. Funct. Mater., 2015, 25 (44), pp 6867-6874), so the inventors anticipate that the molecular weight of the gels of the present invention prior to swelling would be in a similar range. An extensive study of the molecular weight of the gels of the present invention after swelling will be performed using NMR. The inventors' experiments in which they varied the relative concentrations of terminator and polymerizing hairpins suggest bounds on the average number of DNA molecules incorporated at each crosslink. Classic results from polymer chemistry predict that in a reaction where a fraction p of the monomers are "terminating" or incorporate without allowing for further extension, the average length of the polymer in monomer units will be 1/p. This expected chain length is actually consistent with what we observe in our experiments. Because the DNA is much more rigid than the polyacrylamide, one might guess that the uniaxial change in film size would be proportional to change in the length of the crosslinks. We indeed see that this is the case. We plotted the expected chain length 1/p where p ranges from 0.02 to 0.50.

The inventors did not use the 0% (or p=0) values for the plot, since, as the inventors mentioned, without terminators the structures did not stop growing, which also supports this interpretation. These predictions suggest that the average polymer size is on order 50 hairpins based on the current experiments with gels actuated in a 2% terminator solution.

There are many commercial applications of the nucleic-acid directed gel expansion and/or contraction technology of the present invention. Gel contraction technology is further discussed in the section titled, "Methods and Examples". Nucleic acid directed expansion of hydrogels, for example, may be used in biological applications such as a part of a stent. When the gel is position within the body or near a tissue of a subject, it may prevent blood flow or cell migration as the gel expands in response to a specific stimulus such as a nucleic acid. The expandable and/or contractable gels may be applied directly to tissue or cells in vitro or in vivo as a gel, patch, or part of a surgical instrument such as a stent or implant, for example. The gels of the present invention may comprise therapeutic agents and be programmed to release these agents such as small molecules, nanoparticles or antibodies upon the gel's expansion and or contraction to a specific stimulus such as a nucleic acid including one or more DNA hairpins or reversal strands. For example, a DNA cross linked hydrogel in the shape of a patch could be use in biological applications including drug release and may be in contact with tissue that is locate inside or outside (such as skin) of a body and could be used to enhance the healing of internal or external wounds. The gels of the present invention may be used to fill in internal wounds such as vascular aneurysms or be used to close surgical wounds by expanding in the presence of signal such as DNA hairpins. The gels of the present invention may alter cell migration, cell invasion, cell signaling based on material mechanics, modulus, pore size or mesh size as the gel expands creating barriers that affect the movement of biological materials. The gels of the present invention are perfectly suitable for directing gel expansion and/or contraction in robot devices providing biological alternatives to using mechanical principles in robotic design. The gels of the present invention can be programmed to orient, align or change the density of molecules or particles embedded within a gel, such as a hydrogel, for chemical or optical applications based on the specific nucleic acid stimulus chosen prior to gel formation. Other applications of the gels of the present invention are described in FIGS. 34-62 which illustrates a wide range of applications such as tunable PEGDA-DNA, Am-DNA-alginate and GelMA-DNA Gels.

In current practice, aneurysms are often managed by inserting a coil of flexible wire into the aneurysm through an endovascular approach. A hydrogel-based expander of the present invention would be helpful in this context. For example, the hydrogel could be placed in the aneurysm and expanded (by adding DNA hairpins) to fill the aneurysm.

METHODS/EXAMPLES

The following Methods/Examples have been included to provide guidance to one of ordinary skill in the art for practicing representative embodiments of the presently disclosed subject matter. In light of the present disclosure and the general level of skill in the art, those of skill can appreciate that the following Methods/Examples are intended to be exemplary only and that numerous changes, modifications, and alterations can be employed without departing from the scope of the presently disclosed subject matter. The following Examples are offered by way of illustration and not by way of limitation.

DNA Sequences and Sequence Design.

All oligonucleotide sequences are listed in Table 1. The sequences for system 1 crosslinks and polymerizing hairpins, H1 and H2, are based on those used by Venkataraman et al. Oligonucleotides were supplied by Integrated DNA Technologies (IDT) in their lyophilized form. Sequences for all terminating hairpins and the sequences for the crosslinks and hairpins in systems 2-4 were designed using the DNAdesign package, available at: www.dna.caltech.edu/DNAdesign/. This program produces sequences with the necessary complementarity to form the desired secondary structures, while minimizing other potential interactions.

Preparation of DNA-Crosslinked and N, N-Methylenebisacrylamide (BIS)-Crosslinked Pregel Solutions.

Both sets of gels were prepared by UV-initiated, free radical copolymerization of acrylamide along with either N, N-methylenebisacrylamide (BIS) or a DNA duplex as the crosslinker (FIG. S1). To enable its copolymerization with acrylamide, the pre-annealed DNA duplex crosslinker contained oligonucleotides modified at the 5' end with an acrydite moiety. For the DNA pregel solution, stock solutions of the crosslink strands A and R (which contain acrydite modifications), or the crosslink strands for the corresponding system, were first prepared by resuspending lyophilized DNA samples to a final concentration of approximately 25 mM in TAE buffer (40 mM tris-acetate, 1 mM EDTA) that had been previously diluted from 50× stock (Life Technologies, Catalog #24710-030) and supplemented with 12.5 mM magnesium acetate tetrahydrate (Sigma #228648), herein referred to as TAE/Mg$^{2+}$. Oligonucleotide concentrations were verified by absorbance spectroscopy at 260 nm. To prepare the DNA copolymer gel, referred to as poly(Am-co-DNA), to the crosslink strands were added TAE/Mg$^{2+}$ buffer supplemented with calcium chloride (Sigma #C1016)—herein referred to as TAE/Mg$^{2+}$/Ca$^{2+}$— and MilliQ water. The calcium chloride was added to prevent premature dissolution of the poly(acrylic acid) (PAA) sacrificial layer. This solution was then annealed by incubating the solution at 90° C. for five minutes, followed by cooling the solution from 90° C. to 20° C. at 1° C. per minute to allow crosslinks to hybridize. Immediately before photopolymerization, acrylamide (Bio-Rad Catalog #161-0100), Irgacure 2100 (Ciba), and, if applicable, methacryloxyethyl thiocarbamoyl rhodamine B (Polysciences, Inc., catalog #23591) were added to the solution. In cases where the gels were stained with SYBR Green I nucleic acid stain (Invitrogen catalog #S7563), the rhodamine B monomer was omitted. The solution was then mixed via pipet and degassed under vacuum for 5 minutes to minimize the effect of 02 on radical chain polymerization. The final concentrations of all pregel components are as follows: 1.154 mM of strands A and R, 1×TAE/Mg$^{2+}$ buffer, 11.1 mM calcium chloride, 1.41 M acrylamide, 3 vol % of Irgacure 2100, and, if applicable, 2.74 mM methacrylated rhodamine B.

The BIS-crosslinked gel solutions were prepared by mixing MilliQ water, TAE/Mg$^{2+}$/Ca$^{2+}$ buffer, 40% (w/v) 19:1 Am:BIS (BioRad Laboratories, Inc., catalog #1610144), 50% (v/v) Irgacure 2100 in 1-butanol, and, if applicable, 50 mM fluorescein-O-methacrylate (Sigma, catalog #568864) into a test tube. The final concentrations of TAE/Mg$^{2+}$ buffer, and calcium chloride are the same as in the poly(Am-co-DNA) pregel solution. The final concentrations of the other species are as follows: 5% (w/v) of 19:1 Am:BIS, 1.5% (v/v) Irgacure 2100, and, if applicable, 2.74 mM fluorescein-O-methacrylate. The BIS and acrylamide pregel solution was then mixed and degassed following the same protocol of the DNA pregel solution.

Photolithography Chamber Preparation.

The photolithography chambers were prepared according to a previously published protocol. The bottom glass slide served as a substrate onto which the hydrogel samples adhered after photopatterning, while the top slide served as a chromium (Cr) photomask to selectively expose regions of the pregel solution to ultraviolet (UV) light and initiate radical chain polymerization. The top slide of the photolithography chamber was prepared by spin coating SC 1827 (Microposit 51800 Series) on a clean glass slide at 3500 rpm for 3 minutes, followed by baking at 115° C. for 60 seconds. The coated slides were irradiated with a 317 mJ/cm$^2$ dose of 365 nm UV light through film masks designed using AutoCAD and printed by Fineline Imaging. After UV exposure, the glass slides were developed with a 1:10 (w/w) solution of Microposit 351 Developer (Shipley) and DI water, and were dried with N$_2$ gas. Next, a 200 nm layer of Cr was deposited on the glass slide by physical vapor deposition (PVD), after which the slides were consecutively rinsed with acetone and isopropyl alcohol, and were dried under N$_2$ gas to remove the unexposed regions of 1827 positive photoresist. Once prepared, the Cr mask was spin-coated with CYTOP (Type M, Bellex International Corp.) at 4000 rpm and baked at 90° C. for 2 hours to ensure evaporation of the organic solvent. The CYTOP-coated chromium mask prevented the DNA gel from sticking to the mask and allowed for minimal edge roughness.

The bottom slides of the photolithography chamber (Catalog #16004-424, VWR) were prepared by sonicating them in 10% (w/w) NaOH for 30 minutes, rinsing them with MilliQ water, and drying under N$_2$ gas. The bottom slide was then treated with 02 plasma for 5 minutes to fully oxidize the glass surface. Next, a single layer of polyimide tape (~60 μm thick) was placed along the width of the glass slide to act as a spacer. For thinner hydrogels, aluminum foil (~14 μm thick) was used as a spacer. A roughly 200 nm thick layer of 5% (w/w) PAA crosslinked with calcium was then deposited onto the substrate according to a previously reported protocol. Additional washing (3 min in DI water) and baking steps (5 min at 150° C.) were added to the protocol to remove calcium salt deposits present on the substrate after crosslinking the PAA in a solution of CaCl$_2$. The final photolithography chamber was assembled by clipping the top Cr mask and bottom PAA-covered substrate together with binder clips (Office Depot). The chrome layer of the mask faced inward and came into direct contact with the pregel solution.

Photopatterning of Poly(am-Co-DNA) Monolayer and Poly(am-Co-BIS)/Poly(am-Co-DNA) Bilayers.

To photopattern DNA hydrogel monolayers, the DNA pregel solution was injected via pipet into the photolithography chamber. The chamber was then exposed to 365 nm UV light (Neutronix Quintel aligner) for a total light dose of 240 mJ/cm$^2$ as determined by multiplying the measured UV intensity (Vari-Wave II, 365 nm sensor; Quintel) by the exposure time. The chamber was then gently disassembled and 1 mL of 1M NaCl was aliquoted onto the substrate to dissolve the PAA sacrificial layer and yield freestanding samples. The monolayers were then placed into a PDMS-coated polystyrene dish to which approximately 2 mL of TAE/Mg$^{2+}$ was added.

To prepare the first hydrogel layer of a bilayer structure, the previous photopatterning protocol was followed using Am-co-BIS-co-fluorescein pregel solution except that after UV exposure the substrate was washed with approximately 200 µL of TAE/Mg$^{2+}$/Ca$^{2+}$ to remove unreacted pregel solution from the patterned structures. The UV dose for all BIS-crosslinked hydrogel structures is approximately 280 mJ/cm$^2$. The first gel layer was then allowed to dry at room temperature for approximately 20 minutes. The second layer of the hydrogel bilayer structures was fabricated using Am-co-DNA-co-rhodamine pregel solution. Prior to photopatterning, another layer of polyimide tape was placed on the substrate and the second Cr mask was then aligned with the first gel layer using a mask aligner. After satisfactory alignment was achieved, the Am-co-DNA-co-rhodamine solution was injected via pipet into the photolithography chamber and exposed to UV light for a total dose of 240 mJ/cm$^2$. At this point, when the bilayer bar structures were fabricated, the chamber was gently disassembled and approximately 1 mL of 1M NaCl was aliquoted onto the substrate to dissolve the sacrificial layer and yield freestanding bilayer bar structures (FIG. 16). When the petal or crab bilayer structures were fabricated, the above process of washing the patterned structures, aligning the masks, injecting pregel solution, and exposing to UV light is repeated until the final hydrogel domain is patterned, at which point the photolithography chamber is disassembled and 1M NaCl was added to yield free-floating hydrogel structures.

Quantifying the DNA-Driven Expansion and Shape Change of Poly(am-Co-DNA) Hydrogels.

To measure the rate of expansion and final uniaxial swelling rate of poly(Am-co-DNA) hydrogels driven by DNA polymerization, Am-co-DNA pregel solution was prepared as previously described, without methacryloxyethyl thiocarbamoyl rhodamine B, and gels were patterned into either 60 µm or 14 µm thick, 1×1 mm square shapes using appropriate photomasks. After fabrication, the DNA gels were stained overnight in a solution of 2× SYBR Green (Invitrogen catalog #S7563) and TAE/Mg$^{2+}$ buffer. The SYBR staining solution was then removed and the samples were washed several times with TAE/Mg$^{2+}$ buffer. After the last washes, 2 mL of fresh TAE/Mg$^{2+}$ was added to the Petri dish.

All DNA hairpin monomers were supplied by IDT in their lyophilized form, and were resuspended to a final concentration of 2 mM in TAE/Mg$^{2+}$ buffer. All swelling and actuation experiments contained a final hairpin concentration (polymerizing hairpin monomer plus terminator hairpin monomer) of 20 µM. Prior to adding the hairpin solution to the DNA gel samples, the hairpin monomers were snap-cooled in order to remove any aggregates or polymers that may have formed by heating oligonucleotide solutions at 95° C. for at least five minutes, followed by cooling on ice for 2 minutes. Next, the hairpin solution was gently added via syringe so as not to disturb the gel samples. Swelling was recorded via time-lapse fluorescence imaging using a gel imager (Syngene EF2 G:Box) equipped with a blue light transilluminator (Clare Chemical, emission max ~450 nm) and a UV032 filter (Syngene, bandpass 572-630 nm). Images were captured in 20 minute intervals until a steady-state was reached or the gels were no longer visible. The uniaxial swelling ratio of the samples was measured manually in either MATLAB or ImageJ. Fluorescent micrographs in FIG. 2D were false colored for clarity. MATLAB code available upon request.

The volumetric swelling ratios of the BIS and DNA gels were measured by immersing 12 bilayers in DNA-free buffer and imaging bilayers using Nikon AZ100 multi-zoom epifluorescence microscope and Zeiss AxioObserver Yokogawa CSU-X1 spinning disc confocal microscope. Some of the bilayers lain on their sides, which allowed us to image them top-down and others side-on (see the figure below). We measured the contour lengths, widths and thicknesses of the BIS and DNA layers of all the bilayers before and after adding DNA hairpins (20 µM solution composed of 98% polymerizing monomers and 2% terminating monomers) and averaged the values. The average volumetric swelling ratio was calculated by dividing the volume of the gels after and before adding DNA hairpins.

Images of bilayer structures, flowers and crab structures were captured using a Nikon AZ100 multi-zoom epifluorescence microscope equipped with a Nikon DS-Fi1 camera. Fluorescent images of poly(Am-co-DNA-co-rhodamine) gel samples were captured using a Nikon B-2E/C filter cube (excitation 465-495 nm, bandpass emission filter 515-555 nm), whereas images for poly(Am-co-BIS-co-fluorescein) samples were captured using a Nikon G-2E/C filter cube (excitation filter 528-553 nm, bandpass emission filter 590-650 nm). Domains with different crosslink sequences patterned in different sequence steps were false colored in the fluorescent micrographs in FIG. 4, and isolated devices are presented on a black background for clarity. MATLAB code available upon request.

SEM Imaging of Poly(Am-co-DNA) Hydrogels.

Two 5 mm×5 mm hydrogel samples, each 600 µm thick, were fabricated by photopolymerization within a PDMS micromold. The pregel solutions were prepared as previously described without methacryloxyethyl thiocarbamoyl rhodamine B. Prior to photopolymerization the PDMS mold was treated with air plasma for five minutes using a surface corona treater (Electro-Technic Products, model BD-20). The pregel solution was then aliquoted into sample wells of the PDMS mold and exposed to 365 nm UV light (Neutronix Quintel aligner) at an intensity of 7.55 mW/cm$^2$ and dose of 680 mJ/cm$^2$ to ensure complete curing of the pregel solution. The samples were then gently excised from the mold and placed into separate Petri dishes containing 2 mL of fresh TAE/Mg$^{2+}$ buffer. The gels were allowed to swell overnight to equilibrium via solvent uptake. To one DNA gel sample was added two 500 µL hairpin solutions, each containing 117.6 µM of the regular hairpin monomer and 2.4 µM of the respective terminator hairpin (e.g., 117.6 µM H1 and 2.4 µM H1$_T$) for a final concentration of 19.6 µM and 0.4 µM of the polymerizing hairpin monomer and terminator monomer, respectively. One milliliter of TAE/Mg$^{+2}$ was added to the other sample as a control. The two samples were left out at room temperature for two weeks, at which point the swelling solution was removed and the gels were frozen in liquid nitrogen for five minutes. The gel samples were then lyophilized for 24 hours to fully remove the swelling solution (Labconco, Freezone Benchtop Freeze Dry System, Catalog #7382021).

Additional Sequences

System 5 Strands

| DNA STRAND | SEQUENCE | SEQ ID NO: |
|---|---|---|
| S5_10BP-C | /5Acryd/CTCTATCTATCCATCACCCTCA CCTTAC | 42 |
| S5-C' | /5Acryd/GGTGTAAGGTGAGGGTGATGGT AA | 43 |
| S5_10BP-H1 | TTACCATCACCCTCACCTTACTTGTAGATT GGTAAGGTGAGGGTGATGGATAGATAGAG | 44 |
| S5_10BP-H2 | CAATCTACAAGTAAGGTGAGGGTGATGGCT CTATCTATCCATCACCCTCACCTTACACC | 45 |
| S5_8BP-H1 | TTACCATCACCCTCACCTTACTTGTAGATG TAAGGTGAGGGTGATGGATAGATAG | 46 |
| S5_8BP-H2 | ATCTACAAGTAAGGTGAGGGTGATGGCTAT CTATCCATCACCCTCACCTTACACC | 47 |
| S5_6BP-H1 | TTACCATCACCCTCACCTTACTTGTAGGTA AGGTGAGGGTGATGGATAGAT | 48 |
| S5_6BP-H2 | CTACAAGTAAGGTGAGGGTGATGGATCTAT CCATCACCCTCACCTTACACC | 49 |

PEGDA-Based Hydrogels:
Chemicals and DNA

Polyethylene glycol diacrylate Mn 10,000 (PEGDA10k) was obtained from Sigma-Aldrich (Cat. No. 729094). The fluorophore RhodamineB-methacrylate was purchased from PolySciences, Inc. (Cat. No. 25404-100) and used to visualize the hydrogels. The UV-sensitive initiator Irgacure 2100 (BASF) was used to polymerize hydrogels. All DNA strands were purchased with standard desalting purification from Integrated DNA Technologies, Inc. Acrydite-modified strands were solubilized using 1×TAE buffer (Life Technologies, Cat. No. 24710-030) supplemented with 12.5 mM magnesium acetate tetrahydrate (Sigma-Aldrich, Cat. No. M5661). All unmodified DNA strands were solubilized using MilliQ purified water. DNA sequences were adapted from previous literature[1,2] or designed using NUPACK[3] as previously described.

Preparation of DNA Complexes

DNA crosslink complexes were annealed in 1×TAE buffer supplemented with 12.5 mM magnesium acetate tetrahydrate (TAEM) from 90 to 20° C. in an Eppendorf PCR at 1° C./minute at a concentration of 3 mM per strand. Hairpin forming strands were heated to 95° C. for 15 minutes at a concentration of 200 or 600 µM followed by flash cooling on ice for 3 minutes.

Polymerization of poly(PEGDA10k-co-DNA) Hydrogels

PEGDA10k powder was mixed with MilliQ purified water and 10×TAEM. After the PEGDA10k was fully dissolved, acrydite-modified DNA (3 mM), RhodamineB-methacrylate (29.9 mM), and Irgacure 2100 (75% v/v in butanol) were mixed into the solution. The final concentrations were 10% w/v PEGDA10k, 2.74 mM RhodamineB, and 3% v/v Irgacure 2100. The final concentration of DNA was 1.154 mM unless noted otherwise. After mixing with a pipette, the pre-gel solution was sonicated for 10 minutes and degassed for 15 minutes. The pre-gel solution was then UV polymerized using a mask aligner as previously described.[1] The polymerized hydrogel shape and size, as per the mask design, was an equilateral triangle with 1 mm side lengths.

Swelling DNA-Integrated Hydrogels

Hydrogel swelling experiments were conducted with one hydrogel per well in 96-well plates (Fisher Scientific). Hydrogels were swelled in TAEM supplemented with 0.001% v/v Tween20 (TAEM-T20) to prevent hydrogel sticking to the well's surface. Hairpins were added such that at least 604 of the 1004 total in each well was TAEM-T20 and the remaining solution was hairpin stock solution. Images were captured every 30 minutes using a humidified Syngene G:Box EF2 gel imager equipped with a blue light transilluminator (Clare Chemical, Em. max ~450 nm) and UV032 filter (Syngene, bandpass 572-630 nm) or on an Olympus IX73 fluorescence microscope.

Analysis of Hydrogel Swelling

The uniaxial swelling ratio of the hydrogels was measured using custom-written MATLAB code. The edge of the hydrogel was determined using standard intensity-based thresholding and mask image analysis. First, the intensity values of the image were globally adjusted using imadjust to saturate the bottom and top 1% of all pixel values. A gaussian low-pass filter was applied to this adjusted image to reduce or remove background noise and generate the filtered image (FiltImg).

A two-step process was used to determine the threshold used to find the hydrogel's edges. A general mask was generated from the filtered image using:

$$\text{Genmask} = \text{FiltImg} \geq 1.35 * \text{mean(FiltImg)} \quad (1)$$

The general mask (GenMask) is a logical matrix where values of one indicate the bulk hydrogel plus some extra background pixels. The threshold value was then calculated using equation 4.

$$PixOne \text{ matrix} = FiltImg \text{ pixels where } GenMask \text{ pixels are 1} \quad (2)$$

$$PixZero \text{ matrix} = FiltImg \text{ pixels where } GenMask \text{ pixels are 0} \quad (3)$$

$$\text{Thresh} = \frac{\text{mean}(PixOne)}{\text{mean}(PixZero) * \alpha} \quad (4)$$

The parameter alpha varied from image to image in order to provide good agreement between the calculated boundary and the estimated boundary of the hydrogel. The matrix PixZero generally represents the background pixels of the image. The mask with values of one indicating at least the pixels belonging to hydrogel object was calculating using the threshold Thresh:

$$\text{HydMask} = \text{FiltImg} \geq \text{Thresh} * \text{mean(FiltImg)} \quad (5)$$

Objects were removed (values set to 0) from HydMask if their total area was less than 700 pixels. The area of the hydrogels were at least 800 pixels in size. The boundary of the hydrogel was determined using MATLAB's bwboundaries function using a connectivity of 8.

The vertices of the hydrogel were determined from the extrema of the hydrogel object. The extrema and centroids of the objects in HydMask were determined using MATLAB's function regionprops. If background objects (e.g., the side of the well) were found in HydMask, the object with a centroid closest to the center of the image was chosen to be the hydrogel object. k-means clustering was used to determine the location of the vertices from 8 locations provided by the extrema of the hydrogel object. The algorithm was set to detect 4 clusters and the 3 clusters that were the farthest apart were the vertices of the hydrogel. The average distance between these three clusters was used as the measure of the side length of the hydrogel. The uniaxial swelling ratio was calculated using this side length for each image in a time-series (L) relative to the side length prior to adding hairpins ($L_0$).

$$\frac{\Delta L}{L_0} = \frac{L - L_0}{L_0} \quad (6)$$

To investigate the tunability of hydrogel expansion directed by DNA hairpin incorporation by the hybridization chain reaction (FIG. 27a), the inventors started with Mn 10,000 polyethylene glycol diacrylate (PEGDA10k) at 10% w/v and 1.154 mM double-stranded DNA (dsDNA) duplexes with System 1 sequences, named poly(PEGDA10k-co-S1dsDNA1.154), polymerized into a triangular shape. In this hydrogel, the DNA duplexes are a subset of the total crosslinks because PEGDA10k is capable of crosslinking with itself due to the presence of two acrydite moieties on each PEG chain. The presence of both expandable and non-expandable crosslinks is expected to decrease the overall degree of expansion while preventing the hydrogel from undergoing a gel-sol transition. The inventors first confirmed that poly(PEGDA10k-co-S1dsDNA1.154) hydrogels are capable of DNA-triggered expansion by incubating the hydrogels with a solution containing DNA hairpins that polymerized into the DNA crosslinks (FIG. 27a). Indeed, hydrogels expanded in response to DNA hairpins and maintained their triangular shape after expansion (FIG. 27b).

Using a constant base polymer network (e.g., PEGDA10k), there are three major DNA-based parameters that can be tuned to control the rate and extent of DNA-induced hydrogel swelling (FIG. 27c). First, the concentration of the two DNA components, the anchored initiator DNA and the polymerizing hairpins, can be tuned. Increasing hairpin concentration should increase the rate and extent of swelling as more hairpins can be incorporated faster and overall. Increasing anchored DNA concentration should have a similar effect due to having more initiation sites. However, too high of an initiator concentration would lead to a lower number of hairpins incorporated per DNA crosslink once all the hairpins are incorporated, thus leading to a lower degree of crosslink expansion and possibly lower overall hydrogel swelling.

Second, the design of the hairpins, notably the length of the toeholds that initiate hairpin incorporation, can significantly affect the kinetic and thermodynamic properties of the DNA-based polymerization reaction. Increasing the length of the initiating toeholds should increase the rate of hairpin incorporation by increasing the rate constant for DNA strand-displacement. However, increasing the initiating toeholds also increases the size of the loop domain in the hairpins which can lead to undesired hairpin-hairpin polymerization reactions even in the absence of initiators.

The inventors first investigated the effect of DNA crosslink concentration on the rate and degree of DNA hairpin induced hydrogel swelling. The inventors prepared PEGDA10k hydrogels containing 0.25, 0.75, or 1.154 mM double-stranded DNA sequence set A crosslinks and incubated the hydrogels with hairpins containing set A sequences at 20 µM each (FIG. 28a). Increasing the concentration of dsDNA anchored to the hydrogel from 0.25 mM to 1.154 mM increased the uniaxial swelling ratio from 0.25 to 0.83 at 60 hours. The initial rate of swelling, however, appeared to be unaffected by dsDNA anchor concentration when using 20 µM per hairpin to induce swelling. Increasing the hairpin concentration to 60 µM per hairpin increased the initial rate of swelling for 1.154 and 0.75 mM dsDNA anchors compared to 20 µM per hairpin but led to a slight decrease in the degree of swelling (FIG. 28b).

The inventors next investigated whether longer initiating toeholds would enable faster and more swelling of the hydrogels upon hairpin addition. The inventors designed a new set of sequences, termed System 5, with a longer primary initiating toehold on one of the crosslink strands (FIG. 29). The inventors first compared the swelling behavior of PEGDA10k hydrogels crosslinked with this new set of sequences, or poly(PEGDA10k-co-S5dsDNA1.154), with hydrogels crosslinked the System 1 sequences, or poly(PEGDA10k-co-S1dsDNA1.154). Upon incubation with 20 µM of 6 bp long primary toehold hairpins, the inventors found that the hydrogels containing System 5 sequences swelled at a slower rate; reaching a uniaxial swelling ratio of about 0.7 in 70 hours compared to a ratio of 0.8 for hydrogels containing crosslinks with System 1 sequences. This difference is potentially due to the differences in sequences between the two sets as the ratio of the types of bases within a toehold (A, T, C, and G's) can affect the kinetics of toehold-mediated strand-displacement. Toeholds with a lower G/C content have a less negative delta G of hybridization, leading a slower rate of strand-displacement. Indeed, for the 6 bp primary toehold hairpins in System 5, there is only one G/C pair in both initiating toeholds together, while System 1 contains 3 G/C pairs.

The inventors next designed hairpins containing System 5 sequences with 8 bp or 10 bp long primary initiating toeholds (FIG. 30a). The inventors added 20 µM hairpins containing 6, 8, or 10 bp primary initiating toeholds to PEGDA10k hydrogels polymerized with System 5 crosslinks. Interestingly, hydrogels incubated with 8 bp hairpins swelled at a higher rate and to a higher extent by 70 hours than both the 6 bp and 10 bp hairpins (FIG. 30b). While hairpins with 10 bp primary toeholds would be expected to produce the fastest response based upon DNA strand-displacement reaction theory, the relatively large size of the loop (10 bases) in the hairpin structure could allow undesired hairpin-hairpin polymerization reactions, leading to a decrease in the effective hairpin concentration. Unlike the swelling response of poly(PEGDA10k-co-S1dsDNA1.154) hydrogels incubated with 6 bp primary toehold hairpins (FIG. 28), poly(PEGDA10k-co-S5dsDNA1.154) hydrogels showed a dependence upon the concentration of 8 bp primary toehold hairpins incubated with the hydrogels (FIG. 30c). Both the rate and the extent of swelling of poly (PEGDA10k-co-S5dsDNA1.154) hydrogels increased when the concentration of 8 bp primary toehold hairpins was increased from 20 µM per hairpin to 60 µM per hairpin. Poly(PEGDA10k-co-S5dsDNA1.154) hydrogels reached a uniaxial swelling ratio greater than 1 within 24 hours of incubation with 60 µM per hairpin.

Effect of Salt Concentration/Buffer on DNA-Induced Hydrogel Expansion

Synthesis of poly(acrylamide-co-S1dsDNA1.154) hydrogel particles

DNA crosslinks (System 1 sequences) were mixed to a final concentration of 1.154 mM with water, 10×TAEM, acrylamide, rhodamine methacrylate, and Irgacure 2100 (75% v/v in butanol). The final concentrations of acrylamide, rhodamine methacrylate, and Irgacure 2100 were 1.41 M, 2.74 mM, and 3% (v/v), respectively. After mixing, the pre-polymer solutions were degassed under vacuum for 5 minutes. Pre-polymer droplets were prepared using a water-in-oil method (FIG. 28a). Mineral oil USP (CVS Pharmacy)

"wells" were prepared on a cratered parafilm surface and pre-polymer droplets were added using a pipette set to 0.25 µL. Droplets were exposed to 365 nm light using a Benchtop 3UV Transilluminator (UVP) for 1 minute (~4 mW/cm$^2$) to polymerize and crosslink the particles. Particles were purified from the oil using centrifugation into TAEM and were stored at 4° C. until use, usually within 1 week.

Synthesis of poly(PEGDA10k-co-S1dsDNA1.154) hydrogel particles

DNA crosslinks (System 1 sequences) were mixed to a final concentration of 1.154 mM with water, 10×TAEM, PEGDA10k, rhodamine methacrylate, and Irgacure 2100 (75% v/v in butanol). The final concentrations of PEGDA10k, rhodamine methacrylate, and Irgacure 2100 were 10% (w/v), 2.74 mM, and 3% (v/v), respectively. After sonicating for 5 minutes, the pre-polymer solutions were degassed under vacuum for 5 minutes. Pre-polymer droplets were prepared using a water-in-oil method (FIG. 28a). Mineral oil USP (CVS Pharmacy) "wells" were prepared on a cratered parafilm surface and pre-polymer droplets were added using a pipette set to 0.25 4. Droplets were exposed to 365 nm light using a Benchtop 3UV Transilluminator (UVP) for 1 minute (~4 mW/cm$^2$) to polymerize and crosslink the particles. Particles were purified from the oil using centrifugation into TAEM and were stored at 4° C. until use, usually within 1 week.

Particle Area Measurement and Analysis

Images of the fluorescent particles were considered to be accurate 2D projections of the particle size near the center xy-plane. To decrease the sensitivity and bias involved in measuring the diameter, especially of an irregular or non-circular projection, the area of the 2D projection was chosen as the representative variable of particle size and calculated as a function of time for each particle.

The area of the 2D projection of each particle in the fluorescence micrographs was calculated using custom written MATLAB scripts developed using standard edge-detection algorithms. The algorithm used thresholding to determine the boundaries of the particles. This threshold value was calculated using the following method:

1. Normalize the image to the highest and lowest intensity.

$$normImage = \frac{Image - min(Image)}{max(Image) - min(Image)} \quad (1)$$

Use MATLAB's built-in global threshold calculator graythresh.

$$globalThresh = graythresh(normImage) \quad (2)$$

Convert the normalized global threshold into an absolute global threshold and perform image-specific adjustments.

$$Thresh = globalThresh * (max(Image) - min(Image)) + min(Image) \quad (4)$$

$$intThreshOrig = Thresh \text{ of } 1st \text{ image in time series} \quad (5)$$

$$\beta = \frac{mean(Image) * \alpha}{intThreshOrig} \quad (6)$$

$$1.1 \leq \alpha \leq 3 \quad (7)$$

$$particlePixels = Image > \beta * Thresh \quad (8)$$

where α corresponds to a manual input that was adjusted until a close match between the visible particle boundaries and the calculated boundaries was found. By converting the normalized global threshold (which can be used to threshold the normalized image) into the absolute global threshold, the values chosen for a are more standard between image sets and our measurements are more robust against irregularly bright pixels. particlePixels is a logical image mask where values corresponding to 1 indicate pixels that are within the particle's boundary. For particles that did not have significant intensity changes over the course of the experiment (i.e., particles that did not swell to a significant extent), a did not need to be adjusted between images in a time series. For some particles that did swell, and thus did have significant intensity changes, a was manually adjusted about every 5 images. After determining the pixels corresponding to the particle, the particle's area and boundary were extracted using the functions regionprops and bwboundaries.

The area as determined by regionprops was converted into square micrometers using the image's pixel size (4.44 µm/pixel) and the relative change in area as a function of time was calculated using:

$$\Delta area(t) = \frac{area(\tau) - area(t=0)}{area(t=0)} \cdot 100\% \quad (9)$$

Area measurements for each particle were normalized to the initial time point. The curves showing the change in size as a function of time are taken from measurements made every 30 minutes, averaged over multiple particles. The curves were smoothed with a window size of 3.

Swelling Hydrogels Using Anchored Single-Stranded Nucleic Acid ("Tags") and the Hybridization Chain Reaction:

Nucleic Acid Tag (or Anchored Single-Stranded Nucleic Acid):

A single-stranded nucleic acid strand, for example the "C" strand as per the sequence tables and in the table above, that is anchored to the hydrogel matrix and is capable of initiating the hairpin polymerization reaction. In terms of tag structure, this single-stranded nucleic acid strand contains a dock sequence A and a stem sequence (e.g., the "C" strand referenced in the tables). Programmable gels of the present invention may also include tags. For example, a gel may include a first polymer comprising a tag; a first polymerizing hairpin, a second polymerizing hairpin; and a terminating hairpin. The addition of a first polymerizing hairpin, a second polymerizing hairpin and a terminating hairpin to a polymer comprising a tag produces a programmable gel. Gels of the present invention are programmable because the concentration ratio of starting materials are predetermined. In the instant case, the first polymerizing hairpin, the second polymerizing hairpin, and the terminating hairpins are adjusted prior to addition of these elements to a gel. This predetermine concentration ratio controls the timing and/or degree of swelling (or contraction as shown below) of a programmable gel. A suitable tag is single stranded nucleic acid such as an RNA or a DNA. Programmable gels made with tags typically have first polymerizing hairpins comprising a first stem sequence and a second stem sequence, a first dock B sequence, a second anchor A sequence that is complementary to the first anchor A sequence and a second dock A sequence that is complementary to the first dock A sequence. A second polymerizing hairpin may comprise the first stem sequence, the second stem sequence, a second dock B sequence that is complementary to the first dock B sequence, the first dock A sequence; and the first anchor B sequence. The terminating hairpin may comprises the first stem sequence, the second stem sequence, the second dock A sequence, the second anchor A sequence and a terminating sequence.

Figure 63:
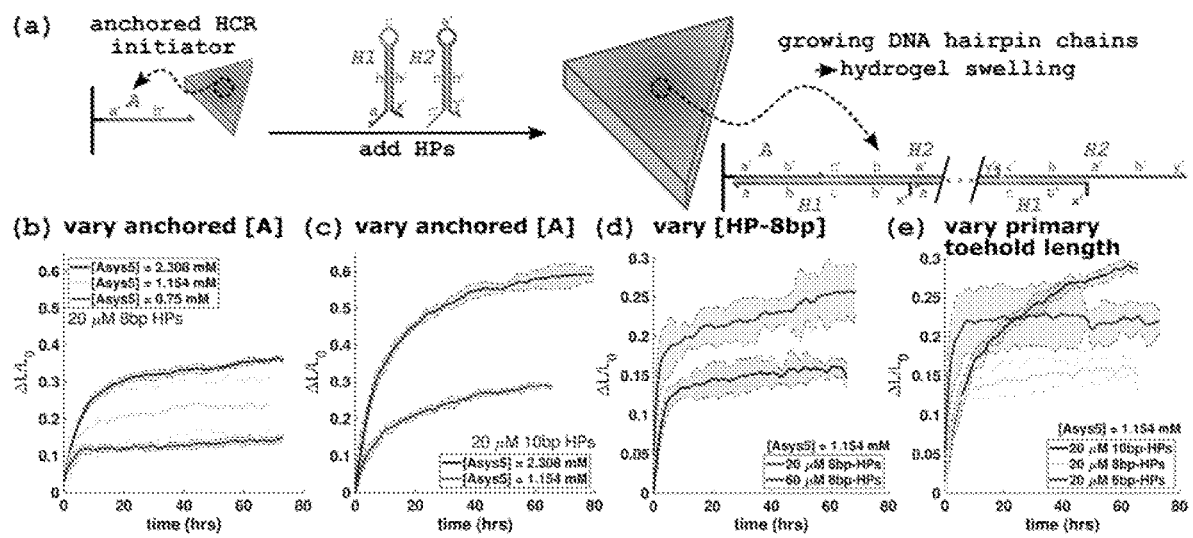

As shown in FIG. 63, expanding hydrogels with anchored single-stranded HCR initiators. (Single-stranded DNA that is capable of initiating the hybridization chain reaction is anchored to hydrogels during hydrogel polymerization. Expansion is initiated by the addition of polymerizing hairpins.

Reversible Gels or Gel Contraction:

Examples of nucleic acid sequences involved in gel contraction or present in reversible gels are provide below.
Additional Sequences:

| DNA STRAND | SEQUENCE | SEQ ID NO: |
|---|---|---|
| System 1: Reversible Hairpins and Reversal Strands | | |
| S1_H1R_36 | CCACGCTGTGGCACCTG CACGCACCCACGTGCAG GTGCCACAGCGAACTTA ATGATTGTGTATAGT | 50 |
| S1_H2R_36 | AGTTAAGAGAATGATTG GGTGCGTGCAGGTGCCA CAGCGTAAGTTCGCTGT GGCACCTGCACGTTG | 51 |
| S1_H1R_36_2TSPC | CCACGCTGTGGCACCTG CACGCACCCATTCGTGC AGGTGCCACAGCGAACT TAATGATTGTGTATAGT | 52 |
| S1_H2R_36_2TSPC | AGTTAAGAGAATGATTG GGTGCGTGCAGGTGCCA CAGCGTTTAAGTTCGCT GTGGCACCTGCACGTTG | 53 |
| S1_H1R_36_5TSPC | CCACGCTGTGGCACCTG CACGCACCCATTTTTCG TGCAGGTGCCACAGCGA ACTTAATGATTGTGTAT AGT | 54 |
| S1_H2R_36_5TSPC | AGTTAAGAGAATGATTG GGTGCGTGCAGGTGCCA CAGCGTTTTTTAAGTTC GCTGTGGCACCTGCACG TTG | 55 |
| S1_REVH1_A6B | ACTATACACAATCATTA AGTTCGCTGTGGCACCT GCACG | 56 |
| S1_REVH2_C6B | CGCTGTGGCACCTGCAC GCACCCAATCATTCTCT TAACT | 57 |
| System 2: Reversible Hairpins and Reversal Strands | | |
| S2_Q1R_36_5NSPC | AAAGCCTACCACTCCGT TGCGGAACCTCTAAGCG CAACGGAGTGGTAGGCA GACAGGTAAGGTAAGAT AGG | 88 |
| S2_Q2R_36_5NSPC | GGGTAGTGTGATGTGAG GTTCCGCAACGGAGTGG TAGGCCTAAGCTGTCTG CCTACCACTCCGTTGCG AAT | 59 |
| S2_REVQ1_A6B | CCTATCTTACCTTACCT GTCTGCCTACCACTCCG TTGCG | 60 |
| S2_REVQ2_C6B | GCCTACCACTCCGTTGC GGAACCTCACATCACAC TACCC | 61 |
| System 5: Reversible Hairpins and Reversal Strands | | |
| S5_H1R_AC8BP | TTACCATCACCCTCACC TTACTTGTAGATGTAAG GTGAGGGTGATGGATAG ATAGGGTAGGTGAATGG GA | 62 |
| S5_H2R_AC8BP | TATGAGTGAGTTAGGAT CTACAAGTAAGGTGAGG GTGATGGCTATCTATCC ATCACCCTCACCTTACA CC | 63 |
| S5_H1R_5TSPC_AC8BP | TTACCATCACCCTCACC TTACTTGTAGATTTTTT GTAAGGTGAGGGTGATG GATAGATAGGGTAGGTG AATGGGA | 64 |
| S5_H2R_5TSPC_AC8BP | TATGAGTGAGTTAGGAT CTACAAGTAAGGTGAGG GTGATGGTTTTCTATC TATCCATCACCCTCACC TTACACC | 65 |

The methods the inventors describe for reversible swelling requires at least two orthogonal types of crosslinks within the hydrogel. One type of crosslink is expandable by the hairpins that can later be reversed, such as crosslink nucleic acid sequences as an example. The second type of crosslink must be incapable of interacting with the hairpins or reversal strands sometimes referred to as a third crosslinker (e.g., physical/covalent crosslinks (PEGDA, bis-acrylamide), a second set of DNA crosslinks of a different sequence, ionic crosslinks).

The inventors have created methods of reversible swelling by adding reversal strands to an expanded gel thereby reducing the size of the gel or contracting the gel. For example, a gel may comprise a first polymer including a first crosslink nucleic acid sequence and a second polymer comprising a second crosslink nucleic acid sequence. The first polymer and the second polymer are crosslinked by the first and second crosslink nucleic acid sequences and a third crosslinker. The gel may also include a first polymerizing hairpin, a second polymerizing hairpin; and a terminating hairpin. The addition of these element to the gel produces a programmable gel that undergoes expansion. The gel may further comprise a first reversal strand and a second reversal strand. The addition of the reversal strands to the programmable, expanded gel breaks polymer cross links and results in shrinkage or contraction of the gel. The concentration ratio of the first polymerizing hairpin, the second polymerizing hairpin, the terminating hairpins, the first reversal strand, and the second reversal strand is determined prior to addition to a gel to control the timing and/or degree of swelling or contraction of a programmable gel. Suitable third crosslinker used in the present invention include a physical, ionic, chemical, or nucleic acid crosslinker. In addition, it is preferably that the first and second polymerizing hairpins, terminating hairpins, and first and second reversal strands are incapable of interacting with the third crosslinker. In addition it is suitable for the first reversal strand to interact with the first polymerizing hairpin and the second reversal strand to interact with the second polymerizing hairpin. FIG. 64 illustrates swelling and contraction of a hydrogel containing DNA crosslinks. DNA crosslinks are expanded by polymerizing hairpins ($H1_p$, $H2_p$), inducing hydrogel swelling. The addition of reversal strands RevH1 and RevH2 disrupts the polymerized hairpin chain and breaks the chain and DNA crosslink. Hairpins then diffuse out of the gel, causing hydrogel contraction and the re-hybridization of the DNA crosslinks. The addition of fresh hairpins re-initializes the expansion of the DNA crosslinks and hydrogel expansion.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A programmable gel comprising:
 a first polymer comprising a first crosslink nucleic acid sequence;
 a second polymer comprising a second crosslink nucleic acid sequence;
 a first polymerizing hairpin capable of binding to the first crosslink nucleic acid sequence;
 a second polymerizing hairpin capable of binding to the second crosslink nucleic acid sequence; and
 a terminating hairpin capable of terminating polymerization.

2. A programmable gel of claim 1 wherein the first crosslink nucleic acid sequence comprises a first stem sequence, a first anchor B sequence, and a first anchor A sequence.

3. The programmable gel of claim 1 wherein the second crosslink nucleic acid sequence comprises a second stem sequence that is complementary to the first stem sequence and the first dock A sequence.

4. The programmable gel of claim 1 wherein the first polymerizing hairpin comprises the first stem sequence and the second stem sequence, a first dock B sequence, a second anchor A sequence that is complementary to the first anchor A sequence and a second dock A sequence that is complementary to the first dock A sequence.

5. The programmable gel of claim 1 wherein the second polymerizing hairpin comprises the first stem sequence, the second stem sequence, a second dock B sequence that is complementary to the first dock B sequence, the first dock A sequence; and the first anchor B sequence.

6. The programmable gel of claim 1 wherein the terminating hairpin comprises the first stem sequence, the second stem sequence, the second dock A sequence, the second anchor A sequence and a terminating sequence.

7. The programmable gel of claim 2 wherein the first stem sequence comprises from 8 to 50 nucleic acid bases.

8. The programmable gel of claim 3 wherein the first dock A sequence comprises up to 10 nucleic acid bases.

9. The programmable gel of claim 4 wherein the first dock B sequence comprises up to 10 nucleic acid bases.

10. The programmable gel of claim 2 wherein the first anchor A sequence comprises up to 10 nucleic acid bases.

11. The programmable gel of claim 2 wherein the anchor B sequence comprises up to 10 nucleic acid bases.

12. A method of making a programmable gel comprising:
 providing a gel comprising a first polymer comprising a first crosslink nucleic acid sequence; a second polymer comprising a second crosslink nucleic acid sequence wherein the first polymer and the second polymer are crosslinked by the first and second crosslink nucleic acid sequences; and
 adding a first polymerizing hairpin, a second polymerizing hairpin; and a terminating hairpin to the gel to produce a programmable gel wherein the first and second hairpins attach to each other resulting in gel swelling;
 wherein a concentration ratio of the first polymerizing hairpin, the second polymerizing hairpin, and terminating hairpins are adjusted prior to addition to gel to control the timing and/or degree of swelling of the programmable gel.

13. A programmable gel of claim 12 wherein the first crosslink nucleic acid sequence comprises a first stem sequence, a first anchor B sequence, and a first anchor A sequence.

14. The programmable gel of claim 12 wherein the second crosslink nucleic acid sequence comprises a second stem sequence that is complementary to the first stem sequence and a first dock A sequence.

15. The programmable gel of claim 12 wherein the first polymerizing hairpin comprises the first stem sequence and a second stem sequence, a first dock B sequence, a second anchor A sequence that is complementary to the first anchor A sequence and a second dock A sequence that is complementary to the first dock A sequence.

16. The programmable gel of claim 12 wherein the second polymerizing hairpin comprises the first stem sequence, the second stem sequence, a second dock B sequence that is complementary to the first dock B sequence, the first dock A sequence; and the first anchor B sequence.

17. The programmable gel of claim 12 wherein the terminating hairpin comprises the first stem sequence, the second stem sequence, the second dock A sequence, the second anchor A sequence and a terminating sequence.

18. An expandable gel comprising:
 a first polymer comprising a first crosslink nucleic acid sequence;
 a second polymer comprising a second crosslink nucleic acid sequence;
 a first polymerizing hairpin capable of binding to the first cross link nucleic acid sequence; and
 a second polymerizing hairpin capable of binding to the first crosslink nucleic acid sequence.

19. A method of making an expandable gel comprising:
 providing a gel comprising a first polymer comprising a first crosslink nucleic acid sequence; a second polymer comprising a second crosslink nucleic acid sequence that are crosslinked by the first and second crosslink nucleic acid sequences;
 adding a first polymerizing hairpin and a second polymerizing hairpin; and
 forming a expanded gel.

20. A photo patterning process to pattern gels into precisely-defined architectures comprising:
 providing a surface comprising a sacrificial layer;
 applying a collection of monomers, a photo-initiator, and a collection of crosslink nucleic acid sequences capable of binding to the monomers;
 placing a mask on top of the programmable gel wherein the mask is impenetrable by light and comprises one or more shapes wherein light is able to penetrate through the shapes on the mask;

applying light to the mask so that light penetrates the shapes on the mask;

polymerizing the monomers;

binding the cross link nucleic acids to the monomers;

forming a collection of polymers comprising attached nucleic acid sequences wherein the nucleic acid sequences crosslink the polymers and the collection of polymers comprises the one or more shapes;

removing the mask;

adding a ratio of polymerizing hairpins and terminating hairpins; and creating a gel having one or more precisely-defined architectures.

21. The photopatterning process of claim 20 comprising the step of removing the collection of polymers from the surface prior to adding the ratio of polymerizing hairpins and terminating hairpins.

22. A method of making a programmable gel comprising:

providing a gel comprising a first polymer comprising a tag;

adding a first polymerizing hairpin, a second polymerizing hairpin, and a terminating hairpin to the gel; and producing a programmable gel that is expanding;

wherein a concentration ratio of the first polymerizing hairpin, the second polymerizing hairpin, and terminating hairpins are adjusted prior to addition to gel to control the timing and/or degree of swelling of the programmable gel.

23. The method of claim 22 wherein the tag is single stranded nucleic acid.

24. The method of claim 23 wherein the tag is DNA.

25. The method of claim 23 wherein the tag has a tag dock B sequence and a tag anchor A sequence.

26. The programmable gel of claim 25 wherein the first polymerizing hairpin comprises a first stem sequence and a second stem sequence, a first dock B sequence, a second anchor A sequence that is complementary to the first anchor A sequence and a second dock A sequence that is complementary to a first dock A sequence.

27. The programmable gel of claim 26 wherein the first dock B sequence binds to the tag dock B sequence and where the second anchor A sequence binds to the tag anchor A sequence.

28. The programmable gel of claim 27 wherein the second polymerizing hairpin comprises the first stem sequence, the second stem sequence, a second dock B sequence that is complementary to the first dock B sequence, the first dock A sequence; and a first anchor B sequence.

29. The programmable gel of claim 28 wherein the terminating hairpin comprises the first stem sequence, the second stem sequence, the second dock A sequence, the second anchor A sequence and a terminating sequence.

30. A method of making a programmable gel that expands and contracts comprising:

providing a gel comprising a first polymer comprising a first crosslink nucleic acid sequence and a second polymer comprising a second crosslink nucleic acid sequence;

crosslinking the first polymer and the second polymer by the first and second crosslink nucleic acid sequences and a third crosslinker;

adding a first polymerizing hairpin, a second polymerizing hairpin; and a terminating hairpin to the gel;

producing a programmable gel that expands;

adding a first reversal strand, a second reversal strand; and contracting the gel compared to a reference gel that does not have a first and second reversal strand added.

31. The method of claim 30 wherein a third polymerizing hairpin and fourth polymerizing hairpin are added to the contracted gel and expands the contracted gel forming an expanded contracted gel.

32. The method of claim 31 wherein a third reversal strand and a fourth reversal strand are added to the expanded contracted gel contracting the expanded contracted gel.

33. The method of claim 30 wherein a concentration ratio of the first polymerizing hairpin, the second polymerizing hairpin, the terminating hairpins, the first reversal strand, and the second reversal strand is adjusted prior to addition to gel to control the timing and/or degree of swelling and/or contraction of the gel.

34. The method of claim 30 wherein the first and the second reversal strands is a nucleic acid.

35. The method of claim 34 wherein the nucleic acid is DNA.

36. The method of claim 30 wherein the third crosslink comprises a physical, ionic, chemical, or nucleic acid crosslink.

37. The method of claim 30 wherein the first and second polymerizing hairpins, terminating hairpins, and first and second reversal strands are incapable of interacting with the third crosslinker.

38. The method of claim 30 wherein the first reversal strand interacts with the first polymerizing hairpin and the second reversal strand interacts with the second polymerizing hairpin.

39. A method of gel contraction comprising:

providing a gel comprising a first polymer comprising a first crosslink nucleic acid sequence and a second polymer comprising a second crosslink nucleic acid sequence wherein the first polymer and the second polymer are crosslinked by the first and second crosslink nucleic acid sequences and a third crosslinker; a first polymerizing hairpin, a second polymerizing hairpin; and a terminating hairpin; and adding a first and a second reversal strand;

contracting the gel when compared to a reference gel that does not have added a first reversal strand and a second reversal strand.

* * * * *